(12) United States Patent
Short et al.

(10) Patent No.: US 12,311,032 B2
(45) Date of Patent: *May 27, 2025

(54) ANTI-Ror2 ANTIBODIES, ANTIBODY FRAGMENTS, THEIR IMMUNOCONJUGATES AND USES THEREOF

(71) Applicant: BioAtla, Inc., San Diego, CA (US)

(72) Inventors: Jay M. Short, Jackson, WY (US); Hwai Wen Chang, San Marcos, CA (US); Gerhard Frey, San Diego, CA (US)

(73) Assignee: BioAlta, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/457,861

(22) Filed: Aug. 29, 2023

(65) Prior Publication Data
US 2024/0092901 A1    Mar. 21, 2024

Related U.S. Application Data

(63) Continuation of application No. 17/533,852, filed on Nov. 23, 2021, now Pat. No. 11,879,011, which is a
(Continued)

(51) Int. Cl.
*A61K 39/395*    (2006.01)
*A61K 38/07*    (2006.01)
(Continued)

(52) U.S. Cl.
CPC .......... *A61K 47/6849* (2017.08); *A61K 38/07* (2013.01); *A61K 39/3955* (2013.01);
(Continued)

(58) Field of Classification Search
CPC ... A61K 39/3955; A61K 39/395; C07K 16/28
See application file for complete search history.

(56) References Cited

U.S. PATENT DOCUMENTS

| 3,896,111 A | 7/1975 | Kupchan et al. |
| 4,137,230 A | 1/1979 | Hashimoto et al. |
| (Continued) | | |

FOREIGN PATENT DOCUMENTS

| AU | 2013306390 A1 | 2/2015 |
| BR | PI0707864-1 A | 5/2011 |
| (Continued) | | |

OTHER PUBLICATIONS

Knappik et al., J. Mol. Biol., 2000, vol. 296(1):57-86.*
(Continued)

*Primary Examiner* — Xiaozhen Xie
(74) *Attorney, Agent, or Firm* — Mendelsohn Dunleavy PC; Kevin J. Dunleavy

(57) ABSTRACT

An antibody or antigen-binding antibody fragment having a heavy chain variable region and/or a light chain variable region that specifically binds to Ror2 antigen, as well as immunoconjugates containing the heavy chain variable region and/or the light chain variable region that bind to Ror2 antigen, are provided. Pharmaceutical compositions and kits comprising the polypeptide or antibodies and antibody fragments containing the polypeptide are also provided.

24 Claims, 21 Drawing Sheets
Specification includes a Sequence Listing.

Related U.S. Application Data continuation of application No. 16/088,769, filed as application No. PCT/US2017/032357 on May 12, 2017, now Pat. No. 11,254,742.

(60) Provisional application No. 62/447,218, filed on Jan. 17, 2017, provisional application No. 62/335,719, filed on May 13, 2016.

(51) Int. Cl.
*A61K 47/68* (2017.01)
*A61P 35/00* (2006.01)
*C07K 16/28* (2006.01)
*A61K 39/00* (2006.01)

(52) U.S. Cl.
CPC .... *A61K 47/6803* (2017.08); *A61K 47/68031* (2023.08); *A61K 47/6811* (2017.08); *A61P 35/00* (2018.01); *C07K 16/28* (2013.01); *C07K 16/2803* (2013.01); *A61K 2039/505* (2013.01); *C07K 2317/24* (2013.01); *C07K 2317/33* (2013.01)

(56) References Cited

U.S. PATENT DOCUMENTS

| | | |
|---|---|---|
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,676,980 A | 6/1987 | Segal et al. |
| 4,683,195 A | 7/1987 | Mullis et al. |
| 4,704,362 A | 11/1987 | Itakura et al. |
| 4,737,456 A | 4/1988 | Weng et al. |
| 4,777,127 A | 10/1988 | Suni et al. |
| 4,797,368 A | 1/1989 | Carter et al. |
| 4,816,567 A | 3/1989 | Cabilly et al. |
| 4,946,778 A | 8/1990 | Ladner et al. |
| 5,139,941 A | 8/1992 | Muzyczka et al. |
| 5,143,854 A | 9/1992 | Pirrung et al. |
| 5,208,020 A | 5/1993 | Chari et al. |
| 5,219,740 A | 6/1993 | Miller et al. |
| 5,362,852 A | 11/1994 | Geoghegan |
| 5,416,064 A | 5/1995 | Chari et al. |
| 5,434,049 A | 7/1995 | Okano |
| 5,500,362 A | 3/1996 | Robinson et al. |
| 5,556,752 A | 9/1996 | Lockhart et al. |
| 5,571,894 A | 11/1996 | Wels et al. |
| 5,587,458 A | 12/1996 | King et al. |
| 5,624,821 A | 4/1997 | Winter et al. |
| 5,632,957 A | 5/1997 | Heller et al. |
| 5,635,483 A | 6/1997 | Pettit et al. |
| 5,641,870 A | 6/1997 | Rinderknecht et al. |
| 5,648,260 A | 7/1997 | Winter et al. |
| 5,663,149 A | 9/1997 | Pettit et al. |
| 5,700,637 A | 12/1997 | Southern |
| 5,712,374 A | 1/1998 | Kunstmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,744,305 A | 4/1998 | Fodor et al. |
| 5,767,237 A | 6/1998 | Sakakibara et al. |
| 5,767,285 A | 6/1998 | Hamann et al. |
| 5,770,456 A | 6/1998 | Holmes |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,800,992 A | 9/1998 | Fodor et al. |
| 5,807,522 A | 9/1998 | Brown et al. |
| 5,821,337 A | 10/1998 | Carter et al. |
| 5,830,645 A | 11/1998 | Pinkel et al. |
| 5,858,358 A | 1/1999 | June et al. |
| 5,866,174 A | 2/1999 | Harada et al. |
| 5,869,046 A | 2/1999 | Presta et al. |
| 5,877,296 A | 3/1999 | Hamann et al. |
| 5,959,098 A | 9/1999 | Goldberg et al. |
| 5,965,452 A | 10/1999 | Kovacs |
| 5,994,136 A | 11/1999 | Naldini et al. |
| 6,013,440 A | 1/2000 | Lipshutz et al. |
| 6,013,516 A | 1/2000 | Verma et al. |
| 6,022,963 A | 2/2000 | McGall et al. |
| 6,045,996 A | 4/2000 | Cronin et al. |
| 6,048,695 A | 4/2000 | Bradley et al. |
| 6,054,270 A | 4/2000 | Southern |
| 6,124,431 A | 9/2000 | Sakakibara et al. |
| 6,171,586 B1 | 1/2001 | Lam et al. |
| 6,194,551 B1 | 2/2001 | Idusogie et al. |
| 6,214,345 B1 | 4/2001 | Firestone et al. |
| 6,248,516 B1 | 6/2001 | Winter et al. |
| 6,258,606 B1 | 7/2001 | Kovacs |
| 6,261,776 B1 | 7/2001 | Pirrung et al. |
| 6,267,958 B1 | 7/2001 | Andya et al. |
| 6,277,489 B1 | 8/2001 | Abbott et al. |
| 6,277,628 B1 | 8/2001 | Johann et al. |
| 6,352,694 B1 | 3/2002 | June et al. |
| 6,441,163 B1 | 8/2002 | Chari et al. |
| 6,534,055 B1 | 3/2003 | June et al. |
| 6,602,684 B1 | 8/2003 | Umana et al. |
| 6,630,579 B2 | 10/2003 | Chari et al. |
| 6,692,964 B1 | 2/2004 | June et al. |
| 6,737,056 B1 | 5/2004 | Presta |
| 6,797,514 B2 | 9/2004 | Berenson et al. |
| 6,867,041 B2 | 3/2005 | Berenson et al. |
| 6,884,799 B2 | 4/2005 | Kamal et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 6,908,744 B1 | 6/2005 | DeChiara et al. |
| 6,913,748 B2 | 7/2005 | Widdison |
| 6,985,321 B2 | 1/2006 | Winter |
| 7,048,311 B2 | 5/2006 | Thurston et al. |
| RE39,151 E | 6/2006 | Chari et al. |
| 7,067,318 B2 | 6/2006 | June et al. |
| 7,067,511 B2 | 6/2006 | Thurston et al. |
| 7,087,409 B2 | 8/2006 | Barbas, III et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,265,105 B2 | 9/2007 | Thurston et al. |
| 7,276,497 B2 | 10/2007 | Chari et al. |
| 7,332,581 B2 | 2/2008 | Presta |
| 7,371,826 B2 | 5/2008 | Presta |
| 7,375,078 B2 | 5/2008 | Feng |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,527,791 B2 | 5/2009 | Adams et al. |
| 7,528,126 B2 | 5/2009 | Howard et al. |
| 7,557,099 B2 | 7/2009 | Howard et al. |
| 7,659,241 B2 | 2/2010 | Senter et al. |
| 8,217,149 B2 | 7/2012 | Irving et al. |
| 8,709,755 B2 | 4/2014 | Short et al. |
| 8,853,369 B2 | 10/2014 | Pei et al. |

(56) References Cited

U.S. PATENT DOCUMENTS

| | | | |
|---|---|---|---|
| 9,388,246 B2 | 7/2016 | Gauthier et al. | |
| 9,447,194 B2 | 9/2016 | Jensen | |
| 9,683,985 B2 | 6/2017 | Kodandapani et al. | |
| 9,902,948 B2 | 2/2018 | Horn | |
| 11,111,288 B2 | 9/2021 | Short et al. | |
| 11,584,927 B2 | 2/2023 | Short | |
| 2001/0008765 A1 | 7/2001 | Shinoki et al. | |
| 2001/0012537 A1 | 8/2001 | Anderson et al. | |
| 2001/0014448 A1 | 8/2001 | Chappa et al. | |
| 2001/0014449 A1 | 8/2001 | Nerenberg et al. | |
| 2001/0016322 A1 | 8/2001 | Caren et al. | |
| 2001/0018642 A1 | 8/2001 | Balaban et al. | |
| 2001/0019827 A1 | 9/2001 | Dawson et al. | |
| 2002/0004587 A1 | 1/2002 | Miller et al. | |
| 2002/0164328 A1 | 11/2002 | Shinkawa et al. | |
| 2003/0096743 A1 | 5/2003 | Senter et al. | |
| 2003/0115614 A1 | 6/2003 | Kanda | |
| 2003/0130189 A1 | 7/2003 | Senter et al. | |
| 2003/0157108 A1 | 8/2003 | Presta | |
| 2004/0093621 A1 | 5/2004 | Shitara et al. | |
| 2004/0109865 A1 | 6/2004 | Niwa et al. | |
| 2004/0110282 A1 | 6/2004 | Kanda et al. | |
| 2004/0110704 A1 | 6/2004 | Yamane et al. | |
| 2004/0132140 A1 | 7/2004 | Satoh et al. | |
| 2005/0014934 A1 | 1/2005 | Hinton et al. | |
| 2005/0123546 A1 | 6/2005 | Umana et al. | |
| 2005/0260186 A1 | 11/2005 | Bookbinder et al. | |
| 2005/0260711 A1 | 11/2005 | Datta et al. | |
| 2005/0276812 A1 | 12/2005 | Ebens, Jr. et al. | |
| 2006/0025576 A1 | 2/2006 | Miller et al. | |
| 2006/0104968 A1 | 5/2006 | Bookbinder et al. | |
| 2006/0121005 A1 | 6/2006 | Berenson et al. | |
| 2007/0111260 A1 | 5/2007 | Gao et al. | |
| 2009/0036431 A1 | 2/2009 | Gauzy et al. | |
| 2009/0047287 A1 | 2/2009 | Billiard et al. | |
| 2009/0130718 A1 | 5/2009 | Short | |
| 2009/0136950 A1 | 5/2009 | DuBridge et al. | |
| 2009/0304710 A1 | 12/2009 | Park et al. | |
| 2010/0034837 A1 | 2/2010 | Beria et al. | |
| 2010/0047257 A1 | 2/2010 | Blanc et al. | |
| 2010/0255004 A1 | 10/2010 | DePinho et al. | |
| 2011/0076287 A1 | 3/2011 | Cohen et al. | |
| 2011/0256157 A1 | 10/2011 | Howard et al. | |
| 2012/0171120 A1 | 7/2012 | Dennis et al. | |
| 2013/0045206 A1 | 2/2013 | Poul et al. | |
| 2013/0203609 A1 | 8/2013 | Horn | |
| 2013/0266579 A1 | 10/2013 | Wei et al. | |
| 2013/0280220 A1 | 10/2013 | Ahmed et al. | |
| 2014/0170159 A9 | 6/2014 | Wei et al. | |
| 2014/0255363 A1 | 9/2014 | Metelitsa et al. | |
| 2014/0271617 A1 | 9/2014 | Igawa et al. | |
| 2014/0322234 A1 | 10/2014 | Nusse et al. | |
| 2014/0322275 A1 | 10/2014 | Brogdon et al. | |
| 2014/0378660 A1 | 12/2014 | Short et al. | |
| 2015/0038684 A1 | 2/2015 | Jensen | |
| 2015/0071923 A1 | 3/2015 | Wei et al. | |
| 2015/0218287 A1 | 8/2015 | Johnson et al. | |
| 2016/0207989 A1 | 7/2016 | Short | |
| 2017/0002061 A1 | 1/2017 | Ellmark et al. | |
| 2017/0260261 A1 | 9/2017 | Short | |
| 2018/0340021 A1 | 11/2018 | Short | |
| 2019/0010219 A1 | 1/2019 | Short | |
| 2019/0010220 A1 | 1/2019 | Short et al. | |

FOREIGN PATENT DOCUMENTS

| | | | |
|---|---|---|---|
| EP | 404097 A2 | 12/1990 | |
| EP | 0425235 A2 | 5/1991 | |
| JP | 2012-533307 A | 12/2012 | |
| JP | 2013-527129 A | 6/2013 | |
| JP | 2013-541940 A | 11/2013 | |
| JP | 2015510761 A | 4/2015 | |
| JP | 7051715 B2 | 4/2022 | |
| KR | 10-2008-0095269 A | 10/2008 | |
| WO | WO8101145 A1 | 4/1981 | |
| WO | 9007936 A1 | 7/1990 | |
| WO | 9102805 A2 | 3/1991 | |
| WO | WO9301161 A1 | 1/1993 | |
| WO | 9303769 A1 | 3/1993 | |
| WO | 9310218 A1 | 5/1993 | |
| WO | WO9308829 A | 5/1993 | |
| WO | 9311230 A1 | 6/1993 | |
| WO | WO9316185 A2 | 8/1993 | |
| WO | 9319191 A1 | 9/1993 | |
| WO | WO9321232 A1 | 10/1993 | |
| WO | 9322429 A1 | 11/1993 | |
| WO | 9325234 A1 | 12/1993 | |
| WO | 9325698 A1 | 12/1993 | |
| WO | 9403622 A1 | 2/1994 | |
| WO | WO9411026 A2 | 5/1994 | |
| WO | 9412649 A2 | 6/1994 | |
| WO | 9428938 A1 | 12/1994 | |
| WO | WO9429351 A2 | 12/1994 | |
| WO | 9500655 A1 | 1/1995 | |
| WO | 9511984 A2 | 5/1995 | |
| WO | 9617958 A1 | 6/1996 | |
| WO | WO9730087 A1 | 8/1997 | |
| WO | 9746313 A1 | 12/1997 | |
| WO | WO9858964 A1 | 12/1998 | |
| WO | 9909217 A1 | 2/1999 | |
| WO | WO9922764 A1 | 5/1999 | |
| WO | 9936569 A1 | 7/1999 | |
| WO | 9951773 A1 | 10/1999 | |
| WO | WO9951642 A1 | 10/1999 | |
| WO | WO0061739 A1 | 10/2000 | |
| WO | WO0129246 A1 | 4/2001 | |
| WO | WO0231140 A1 | 4/2002 | |
| WO | WO02088172 A1 | 11/2002 | |
| WO | WO03001878 A2 | 2/2003 | |
| WO | WO03026577 A2 | 4/2003 | |
| WO | WO03043583 A2 | 5/2003 | |
| WO | WO03084570 A1 | 10/2003 | |
| WO | WO03085107 A1 | 10/2003 | |
| WO | WO03085119 A1 | 10/2003 | |
| WO | WO2004008147 A2 | 1/2004 | |
| WO | WO2004032828 A2 | 4/2004 | |
| WO | WO2004056312 A2 | 7/2004 | |
| WO | WO2005035586 A1 | 4/2005 | |
| WO | WO2005035778 A1 | 4/2005 | |
| WO | WO2005053742 A2 | 6/2005 | |
| WO | WO2005100402 A1 | 10/2005 | |
| WO | 2006023957 A1 | 3/2006 | |
| WO | WO2006029879 A2 | 3/2006 | |
| WO | WO2006044908 A2 | 4/2006 | |
| WO | WO2007008848 A2 | 1/2007 | |
| WO | WO2008008603 A1 | 1/2007 | |
| WO | WO2008077546 A1 | 7/2008 | |
| WO | WO2009016516 A2 | 2/2009 | |
| WO | WO2009062690 A1 | 5/2009 | |
| WO | WO2009063965 A1 | 5/2009 | |
| WO | WO2009089004 A1 | 7/2009 | |
| WO | WO2009099741 A1 | 8/2009 | |
| WO | WO2010009124 A2 | 1/2010 | |
| WO | 2010025177 A1 | 3/2010 | |
| WO | 2010104821 A1 | 9/2010 | |
| WO | 2011009058 A2 | 1/2011 | |
| WO | WO2011014457 A1 | 2/2011 | |
| WO | WO2011056983 A1 | 5/2011 | |
| WO | 2011109726 A2 | 9/2011 | |
| WO | WO2011130598 A1 | 10/2011 | |
| WO | 2011157905 A1 | 12/2011 | |
| WO | 2012031744 A1 | 3/2012 | |
| WO | 2012033953 A1 | 3/2012 | |
| WO | 2012099973 A2 | 7/2012 | |
| WO | 2012156747 A1 | 11/2012 | |
| WO | 2013103637 A1 | 7/2013 | |
| WO | 2013123061 A | 8/2013 | |
| WO | 2013126729 A1 | 8/2013 | |
| WO | 2013126733 A1 | 8/2013 | |
| WO | 2013134743 A1 | 9/2013 | |
| WO | 2013152059 A1 | 10/2013 | |
| WO | 2013170168 A1 | 11/2013 | |
| WO | 2014011993 A2 | 1/2014 | |
| WO | 2014039523 A1 | 3/2014 | |

(56) References Cited

FOREIGN PATENT DOCUMENTS

| WO | 2014127261 A1 | 8/2014 |
|---|---|---|
| WO | 2015028444 A1 | 3/2015 |
| WO | 2016138071 A1 | 1/2016 |
| WO | 2016036916 A1 | 3/2016 |
| WO | 2017180842 A1 | 10/2017 |
| WO | 2018044619 A1 | 3/2018 |
| WO | 2018136570 A1 | 7/2018 |

OTHER PUBLICATIONS

Rabia et al., Biochem. Eng. J., 2018, vol. 137:365-374.*
Buckel et al., Cancer Res., Apr. 1, 2015, vol. 75(7):1376-1387.*
Notice of Deficiencies for corresponding Israeli application No. 308504; dated Jun. 23, 2024 (5 pages).
Examination Report for corresponding Singaporean application No. 11201808882Q; dated Jul. 6, 2024 (6 pages).
Zhang, Kathy, et al. "Comprehensive optimization of a single-chain variable domain antibody fragment as a targeting ligand for a cytotoxic nanoparticle." MAbs. 7.1 (2015): 42-52.
Debebe, Zufan, et al. "Ror2 as a Therapeutic Target in Cancer." Pharmacology & Therapeutics 150 (2015): 143-148.
Notice of Rejection for corresponding Japanese application No. 2018-559715; dated Nov. 9, 2021 (8 pages).
Knappik Achim, et al. "Fully synthetic human combinatorial antibody libraries (HuCAL) based on modular consensus frameworks and CDRs randomized with trinucleotides." Journal of Molecular Biology 296.1 (2000): 57-86.
Rabia, Lilia A., et al. "Understanding and overcoming trade-offs between antibody affinity, specificity, stability and solubility." Biochemical Engineering Journal 137 (2018): 365-374.
Rudikoff, Stuart, et al. "Single amino acid substitution altering antigen-binding specificity." Proceedings of the National Academy of Sciences 79.6 (1982): 1979-1983.
Notification of Reason for Refusal for corresponding Korean application No. 10-2018-7032869; dated Nov. 26, 2021 (17 pages) Machine Translation.
First Office Action for corresponding Chinese application No. 20178002947.6; dated Dec. 1, 2021 (17 pages) Machine Translation.
Edris, Badreddin, et al. "ROR2 is a novel prognostic biomarker and a potential therapeutic target in leiomyosarcoma and gastrointestinal stromal tumour." The Journal of Pathology 227.2 (2012): 223-233.
Zhang, Jie, et al. "Wnt5a signaling pathway and its role in cell motility." Chinese Bulletin of Life Sciences 25.3 (2013): 289-294 (Machine Translation).
Official Action for corresponding Israeli application No. 262404; dated Dec. 7, 2021 (4 pages).
Haso, Waleed, et al. "CD22-targeted chimeric antigen receptor (CAR) T cells containing the 4-1BB costimulatory domain demonstrate enhanced persistence and superior efficacy against B-cell precursor acute lymphoblastic leukemia (ALL) compared to those containing CD28." Abstract, Blood 122.21 (2013): 1431-1431.
Bedzyk, William D., et al. "Immunological and structural characterization of a high affinity anti-fluorescein single-chain antibody." Journal of biological chemistry 265.30 (1990): 18615-18620.
Caldwell, Charles R., and Carol E. Whitman. "Temperature-induced protein conformational changes in barley root plasma membrane-enriched microsomes I. Effect of temperature on membrane protein and lipid mobility." Plant physiology 84.3 (1987): 918-923.
Cartellieri, Marc, et al. "Chimeric antigen receptor-engineered T cells for immunotherapy of cancer." BioMed Research International 2010 (2010): 1-13.
Chaudhary, Vijay K., et al. "A recombinant single-chain immunotoxin composed of anti-Tac variable regions and a truncated diphtheria toxin." Proceedings of the National Academy of Sciences 87.23 (1990): 9491-9494.
Di Russo, Natali V., et al. "pH-Dependent Conformational Changes in Proteins and Their Effect on Experimental pK as: The Case of Nitrophorin 4." PLoS Comput Biol 8.11 (2012): e1002761.
Estrella, Veronica, et al. "Acidity generated by the tumor microenvironment drives local invasion." Cancer research 73.5 (2013): 1524-1535.
Faes, Seraina, et al. "Acidic pH reduces VEGF-mediated endothelial cell responses by downregulation of VEGFR-2; relevance for anti-angiogenic therapies." Oncotarget 7.52 (2016): 86026.
Gandhi, Sejal. "Effect of PH and Temperature on Conformational 79anges of a Humanized Monoclonal Antibody." Open Access Master's Theses. Paper 249 (2002) 1-79.
Grada, Zakaria, et al. "TanCAR: a novel bispecific chimeric antigen receptor for cancer immunotherapy." Molecular Therapy—Nucleic Acids 2.7 (2013): e105.
Han, Jianfeng, et al. "CAR-Engineered NK Cells Targeting Wild-Type EGFR and EGFRvIII Enhance Killing of Glioblastoma and Patient-Derived Glioblastoma Stem Cells." Scientific Reports 5 (2015): 11483. (13 pages).
Hudecek, Michael, et al. "The non-signaling extracellular spacer domain of chimeric antigen receptors is decisive for in vivo anti-tumor activity." Cancer immunology research (2014): canimm-0127.
Inaguma, Y., et al. "Construction and molecular characterization of a T-cell receptor-like antibody and CAR-T cells specific for minor histocompatibility antigen HA-1H." Gene Therapy 21.6 (2014): 575-584.
Jäckel, C., et al. "Protein design by directed evolution." Annu. Rev. Biophys. 37 (2008): 153-173.
Jena, B. et al. (2010). "Redirecting T-cell specificity by introducing a tumor-specific chimeric antigen receptor." Blood, The Journal of the American Society of Hematology 116.7 (2010): 1035-1044.
Jensen, Michael C., and Stanley R. Riddell. "Design and implementation of adoptive therapy with chimeric antigen receptor-modified T cells." Immunological reviews 257.1 (2014): 127-144.
Justus, C., et al. "Acidic tumor microenvironment and pH-sensing G protein-coupled receptors." Frontiers in physiology 4 (2013): 354.
Kong, Seogkyoung, et al. "Suppression of human glioma xenografts with second-generation IL13R-specific chimeric antigen receptor-modified T cells." Clinical Cancer Research 18.21 (2012): 5949-5960.
Kunii, Naoki, et al. "Enhanced function of redirected human T cells expressing linker for activation of T cells that is resistant to ubiquitylation." Human gene therapy 24.1 (2013): 27-37.
Liao, M., et al. "Site-directed antibodies against the stem region reveal low pH-induced conformational changes of the Semliki Forest virus fusion protein." Journal of virology 80.19 (2006): 9599-9607.
Ma, Jennifer SY, et al. "Versatile strategy for controlling the specificity and activity of engineered T cells." Proceedings of the National Academy of Sciences (2016): 201524193.
Maetzig, Tobias, et al. "Gammaretroviral Vectors: Biology, Technology and Application." Viruses 3.6 (2011): 677-713.
Miao, H., et al. "EGFRvIII-Specific Chimeric Antigen Receptor T Cells Migrate to and Kill Tumor." PLOS One 9.4 Article e94281 (2014), pp. 1-9.
Pirooznia, Nazanin, et al. "The construction of chimeric T-Cell receptor with spacer base of modeling study of VHH and MUC1 interaction." Journal of BioMed Research 2011 (2011): 1-11.
Raso, Vic, et al. "Antibodies capable of releasing diphtheria toxin in response to the low pH found in endosomes." Journal of Biological Chemistry 272.44 (1997): 27618-27622.
Reverberi, Roberto et al. "Factors Affecting the Antigen-antibody Reaction." Blood Transfusion 5.4 (2007): 227-240.
Rothe, Achim, et al. "A phase 1 study of the bispecific anti-CD30/CD16A antibody construct AFM13 in patients with relapsed or refractory Hodgkin lymphoma." Blood 125.26 (2015): 4024-4031.
Sadelain, Michel, Renier Brentjens, and Isabelle Rivière. "The basic principles of chimeric antigen receptor design." Cancer discovery 3.4 (2013): 388-398.
Xiong, Cheng-Yi, et al. "Development of tumor targeting anti-MUC-1 multimer: effects of di-scFv unpaired cysteine location on PEGylation and tumor binding." Protein Engineering Design and Selection 19.8 (2006): 359-367.

(56) References Cited

OTHER PUBLICATIONS

He, Xi et al., "pH-sensitive drug-delivery systems for tumor targeting." Therapeutic Delivery 4.12 (2013): 1499-1510.
Igawa, T et al., "pH-dependent antigen-binding antibodies as a novel therapeutic modality." Biochimica et Biophysica Acta (BBA)—Proteins and Proteomics 1844.11 (2014): 1943-1950.
Bridgeman, John S., et al. "The Optimal Antigen Response of Chimeric Antigen Receptors Harboring The Cd3 ζ Transmembrane Domain Is Dependent upon Incorporation of the Receptor into the Endogenous TCR/CD3 Complex." The Journal of Immunology 184.12 (2010): 6938-6949.
Bumbaca, Daniela et al. "Highly specific off-target binding identified and eliminated during the humanization of an antibody against FGF receptor 4" mAbs 3.4 (2011): 376-386.
Devanaboyina, Siva Charan et al. "The effect of pH dependence of antibody-antigen interactions on subcellular trafficking dynamics" mAbs 5.6 (2013): 851-859.
Daugherty, Patrick S et al. "Quantitative analysis of the effect of the mutation frequency on the affinity mutation of single chain Fv antibodies" Proceedings of the National Academy of Sciences 97.5 (2000): 2029-2034.
Ducancel, Frédéric et al. "Molecular engineering of antibodies for therapeutic and diagnostic purposes" mAbs 4.4 (2012): 445-457.
Haso, Waleed et al. "Anti-CD22-chimeric antigen receptors targeting B-cell precursor acute lymphoblastic leukemia." Blood 121.7 (2013): 1165-1174.
Hudecek, Michael, et al. "Receptor affinity and extracellular domain modifications affect tumor recognition by ROR1-specific chimeric antigen receptor T cells." Clinical Cancer Research 19.12 (2013): 3153-3164.
Ho, Mitchell et al. "In Vitro Antibody Evolution Targeting Germline Hot Spots to Increase Activity of an Anti-CD22 Immunotoxin" The Journal of Biological Chemistry 280.1 (2005): 607-617.
Igawa, Tomoyuki, et al. "Antibody recycling by engineered pH-dependent antigen binding improves the duration of antigen neutralization." Nature Biotechnology 28.11 (2010): 1203-1207.
Technical Examination Report for Brazilian application No. BR112017003835-8; dated Feb. 6, 2024 (8 pages) Machine Translation.
Office Action for Canadian application No. 2,996,514; dated Feb. 7, 2024 (3 pages).
Communication pursuant to Article 94(3) EPC for European application No. 16839728.9; dated Mar. 12, 2024 (5 pages).
Hearing Notice for Indian application No. 201817038956; dated Apr. 15, 2024 (2 pages).
First Office Action for Chinese application No. 201980058347.2; dated Oct. 10, 2023 (20 pages).
Notice of Reasons for Rejection for Japanese application No. 2021-512647; dated Jun. 27, 2023 (16 pages) Machine Translation.
Examination Report for corresponding Australian application No. 2017263568; dated Jul. 4, 2023 (3 pages).
Decision of Rejection for corresponding Japanese application No. 2022-055649; dated Aug. 8, 2023 (6 pages).
Office Action for Taiwanese application No. 108132177; dated Aug. 11, 2023 (23 pages) Machine Translation.
Communication pursuant to Article 94(3) EPC for corresponding European application No. 22164162.4; dated Jul. 21, 2023 (5 pages).
Examination Report for Canadian application No. 2,959,141; dated Aug. 24, 2023 (5 pages).
Notice of Reasons for Rejection for Japanese application No. 2021-082062; dated Aug. 29, 2023 (7 pages) Machine Translation.
Igawa, Tomoyuki, et al. "Engineering the variable region of therapeutic IgG antibodies." MAbs. vol. 3. No. 3. Taylor & Francis (2011): 243-252.
Jellusova, Julia, and Lars Nitschke. "Regulation of B cell functions by the sialic acid-binding receptors siglec-G and CD22." Frontiers in Immunology 2.96 (2012): (14 pages).
Song, Chang W., et al. "Influence of tumor pH on therapeutic response." Cancer Drug Resistance. Humana Press, (2006): 21-42.

Vincent, Karen J., et al. "Current strategies in antibody engineering: Fc engineering and pH-dependent antigen binding, bispecific antibodies and antibody drug conjugates." Biotechnology Journal 7.12 (2012): 1444-1450.
Gerweck, Leo E., et al. "Cellular pH Gradient in Tumor versus Normal Tissue: Potential Exploitation for the Treatment of Cancer." Cancer Research 56.6 (1996): 1194-1198.
Shirmanova, Marina V., et al. "Intracellular pH imaging in cancer cells in vitro and tumors in vivo using the new genetically encoded sensor SypHer2." Biochimica et Biophysica Acta 1850.9 (2015): 1905-1911.
Ramos, Carlos A., et al. "CAR-T Cell Therapy for Lymphoma." Annual Review of Medicine 67 (2016): 165-183.
Aujla, Amandeep, et al. "Inotuzumab ozogamicin in clinical development for acute lymphoblastic leukemia and non-Hodgkin lymphoma." Biomarker Research 7.9 (2019): 1-10.
Long, Adrienne H., et al. "Lessons learned from a highly-active CD22-specific chimeric antigen receptor." Oncoimmunology 2.4 paper e23621 (2013): 1-3.
Haso, Waleed, et al. "A New High Activity Anti-CD22 Chimeric Antigen Receptor (CAR) Targeting B Cell Leukemia." Abstract, Blood 120.21 (2012): 2611-2611.
Pop, Laurentiu M., et al. "A reevaluation of CD22 expression in human lung cancer." Cancer Research 74.1 (2014): 263-271.
Tannock, Ian F., et al. "Acid pH in tumors and its potential for therapeutic exploitation." Cancer Research 49.16 (1989): 4373-4384.
Zhang, Li, et al. "Pluripotent stem cell-derived CAR-macrophage cells with antigen-dependent anti-cancer cell functions." Journal of Hematology & Oncology 13.153 (2020): 1-5.
Chen, Ching, et al. "Generation and analysis of random point mutations in an antibody CDR2 sequence: many mutated antibodies lose their ability to bind antigen." The Journal of Experimental Medicine 176.3 (1992): 855-866.
Sela-Culang, Inbal, et al. "The structural basis of antibody-antigen recognition." Frontiers in Immunology vol. 4 Article 302 (2013): 1-13.
Vajdos, Felix F., et al. "Comprehensive functional maps of the antigen-binding site of an anti-ErbB2 antibody obtained with shotgun scanning mutagenesis." Journal of Molecular Biology 320.2 (2002): 415-428.
Petrova, Tatiana V., et al. "VEGFR-3 expression is restricted to blood and lymphatic vessels in solid tumors." Cancer Cell 13.6 (2008): 554-556.
Wang, W., et al. "Specificity redirection by CAR with human VEGFR-1 affinity endows T lymphocytes with tumor-killing ability and anti-angiogenic potency." Gene Therapy 20.10 (2013): 970-978.
Zhao, Yangbing, et al. "A herceptin-based chimeric antigen receptor with modified signaling domains leads to enhanced survival of transduced T lymphocytes and antitumor activity." The Journal of Immunology 183.9 (2009): 5563-5574.
Second Office Action for corresponding Chinese applicaiton No. 201780029427.6; dated May 12, 2022 (15 pages) Machine Translation.
Cho, Jang Hwan, et al. "Engineering Axl specific CAR and SynNotch receptor for cancer therapy." Scientific Reports 8.1 (2018): 1-8.
Nerreter, T., et al. "ROR2 is a novel target for CAR T cells in breast cancer." Oncology Research And Treatment 40.3 (2017): p. 130 (abstract).
Wei, Jing, et al. "A novel AXL chimeric antigen receptor endows T cells with anti-tumor effects against triple negative breast cancers." Cellular Immunology 331 (2018): 49-58.
Examination Report for corresponding Mexican application No. MX/a/2018/013306; dated Mar. 25, 2022 (14 pages) Machine Translation.
Third Written Opinion for Singaporean application No. 11201808882Q; dated Jul. 5, 2022 (8 pages).
Notice of Final Rejection for Korean application No. 10-2018-7032869; dated Jul. 27, 2022 (12 pages); Machine Translation.
Examination Report for Indian application No. 201817038956; dated Oct. 3, 2022 (7 pages).

(56) References Cited

OTHER PUBLICATIONS

Rejection Decision for Chinese application No. 201780029427.6; dated Nov. 2, 2022 (12 pages) Machine Translation.
Examination Report for Taiwanese application No. 106115891; dated Sep. 21, 2022 (9 pages).
Examination Report for Taiwanese application No. 110142601; dated Sep. 21, 2022 (9 pages).
Extended European Search Report for European application No. 22181149.0; dated Dec. 5, 2022 (9 pages).
Final Rejection for Korean application No. KR 10-2018-7032869; dated Dec. 23, 2022 (15 pages).
Non-Final Office Action for U.S. Appl. No. 15/504,470; dated Mar. 23, 2023 (78 pages).
Office Action for Israeli application No. 262404; dated Mar. 7, 2023 (6 pages) Machine Translation.
Office Action for Taiwanese application No. 106115891; dated Dec. 23, 2022 (9 pages) Machine Translation.
Office Action for Taiwanese application No. 110142601; dated Dec. 23, 2022 (9 pages) Machine Translation.
Andrea, Alain E., et al. "Advances in CAR-T cell Genetic Engineering Strategies to Overcome Hurdles in Solid Tumors Treatment." Frontiers in Immunology 13.309 (2022): 1-39.
Atkinson, T. Prescott, et al. "Splice variant in TCRζ links T cell receptor signaling to a G-protein-related signaling pathway." Biochemical and Biophysical Research Communications 310.3 (2003): 761-766.
Bonvin, Pauline, et al. "De novo isolation of antibodies with pH-dependent binding properties." mAbs 7.2 (2015): 294-302.
Chataigner, Lucas M. P., et al.. "Structural Perspectives on Extracellular Recognition and Conformational Changes of Several Type-I Transmembrane Receptors." Frontiers in Molecular Biosciences 7.129 (2020): 1-10.
Guo, Yabin, et al. "Sleeping Beauty transposon integrates into non-TA dinucleotides." Mobile DNA 9.8 (2018): 1-7.
HernÁndez-Caselles, Trinidad, et al. "A study of CD33 (SIGLEC-3) antigen expression and function on activated human T and NK cells: two isoforms of CD33 are generated by alternative splicing." Journal of Leukocyte Biology 79.1 (2006): 46-58.
Johnston, Robert J., et al. "VISTA is an acidic pH-selective ligand for PSGL-1." Nature 574.7779 (2019): 565-570.
Kato, Yasumasa, et al. "Acidic extracellular microenvironment and cancer." Cancer Cell International 13.89 (2013): 1-8.
Lee, Peter S., et al. "Improved therapeutic index of an acidic pH-selective antibody."mAbs 14.1 (2022): 1-14.
Pilon-Thomas, Shari, et al. "Neutralization of tumor acidity improves antitumor responses to immunotherapy." Cancer Research 76.6 (2016): 1381-1390.
Rodriguez-Garcia, Alba, et al. "CAR-T Cells Hit the Tumor Microenvironment: Strategies to Overcome Tumor Escape." Frontiers in Immunology 11.1109 (2020):1-17.
Notice of Reasons for Rejection for corresponding Japanese application No. 2022-055649; dated Mar. 28, 2023 (10 pages).
Request for Submission of Opinion for Korean application No. 10-2018-7006771; dated May 10, 2023 (12 pages) Machine Translation.
Office Action for corresponding Canadian application No. 3,023,979; dated May 5, 2023 (10 pages).
Kam, Nadine Wong Shi, et al. "Carbon nanotubes as multifunctional biological transporters and near-infrared agents for selective cancer cell destruction." Proceedings of the National Academy of Sciences of the United States of America 102.33 (2005): 11600-11605.
Morrison, Sherie L., et al. "Chimeric human antibody molecules: mouse antigen-binding domains with human constant region domains." Proceedings of the National Academy of Sciences 81.21 (1984): 6851-6855.
Hellström, Ingegerd, Vera Brankovan, and K. E. Hellström. "Strong antitumor activities of IgG3 antibodies to a human melanoma-associated ganglioside." Proceedings of the National Academy of Sciences 82.5 (1985): 1499-1502.
Hellström, Ingegerd, Paul L. Beaumier, and Karl Erik Hellström. "Antitumor effects of L6, an IgG2a antibody that reacts with most human carcinomas." Proceedings of the National Academy of Sciences 83.18 (1986): 7059-7063.
Chothia, Cyrus, and Arthur M. Lesk. "Canonical structures for the hypervariable regions of immunoglobulins." Journal of molecular biology 196.4 (1987): 901-917.
Brüggemann, M., et al. "Comparison of the effector functions of human immunoglobulins using a matched set of chimeric antibodies." The Journal of experimental medicine 166.5 (1987): 1351-1361.
Presta, Leonard G., et al. "Humanization of an anti-vascular endothelial growth factor monoclonal antibody for the therapy of solid tumors and other disorders." Cancer research 57.20 (1997): 4593-4599.
Queen, Cary, et al. "A humanized antibody that binds to the interleukin 2 receptor." Proceedings of the National Academy of Sciences 86.24 (1989): 10029-10033.
Carter, Paul, et al. "Humanization of an anti-p185HER2 antibody for human cancer therapy." Proceedings of the National Academy of Sciences 89.10 (1992): 4285-4289.
Hinman, Lois M., et al. "Preparation and characterization of monoclonal antibody conjugates of the calicheamicins: a novel and potent family of antitumor antibiotics." Cancer research 53.14 (1993): 3336-3342.
Rodrigues, Maria L., et al. "Synthesis and β-lactamase-mediated activation of a cephalosporin-taxol prodrug." Chemistry & biology 2.4 (1995): 223-227.
Rosok, Mae Joanne, et al. "A combinatorial library strategy for the rapid humanization of anticarcinoma BR96 Fab." Journal of Biological Chemistry 271.37 (1996): 22611-22618.
Liu, Changnian, et al. "Eradication of large colon tumor xenografts by targeted delivery of maytansinoids." Proceedings of the National Academy of Sciences 93.16 (1996): 8618-8623.
Baca, Manuel, et al. "Antibody humanization using monovalent phage display." Journal of Biological Chemistry 272.16 (1997): 10678-10684.
Clynes, Raphael, et al. "Fc receptors are required in passive and active immunity to melanoma." Proceedings of the National Academy of Sciences 95.2 (1998): 652-656.
Lode, Holger N., et al. "Targeted Therapy with a Novel Enediyene Antibiotic Calicheamicin 248 11 Effectively Suppresses Growth and Dissemination of Liver Metastases in a Syngeneic Model of Murine Neuroblastoma." Cancer research 58.14 (1998): 2925-2928.
Pettit, Robin K., George R. Pettit, and Kevin C. Hazen. "Specific activities of dolastatin 10 and peptide derivatives against Cryptococcus neoformans." Antimicrobial agents and chemotherapy 42.11 (1998): 2961-2965.
Chen, Yvonne, et al. "Selection and analysis of an optimized anti-VEGF antibody: crystal structure of an affinity-matured Fab in complex with antigen." Journal of molecular biology 293.4 (1999): 865-881.
Nagy, Attila, Artur Plonowski, and Andrew V. Schally. "Stability of cytotoxic luteinizing hormone-releasing hormone conjugate (AN-152) containing doxorubicin 14-O-hemiglutarate in mouse and human serum in vitro: implications for the design of preclinical studies." Proceedings of the National Academy of Sciences 97.2 (2000): 829-834.
Klimka, A., et al. "Human anti-CD30 recombinant antibodies by guided phage antibody selection using cell panning." British journal of cancer 83.2 (2000): 252.
Hay, Michael P., et al. "A 2-nitroimidazole carbamate prodrug of 5-amino-1-(chloromethyl)-3-[(5, 6, 7-trimethoxyindol-2-yl) carbonyl]-1, 2-dihydro-3H-benz [e] indole (amino-seco-CBI-TMI) for use with ADEPT and GDEPT." Bioorganic & medicinal chemistry letters 9.15 (1999): 2237-2242.
Saleh, Mansoor N., et al. "Phase I Trial of the Anti-Lewis Y Drug Immunoconjugate BR96-Doxorubicin in Patients With Lewis Y-Expressing Epithelial Tumors." Journal of Clinical Oncology 18.11 (2000): 2282-2292.
Idusogie, Esohe E., et al. "Mapping of the C1q binding site on rituxan, a chimeric antibody with a human IgG1 Fc." The Journal of Immunology 164.8 (2000): 4178-4184.

(56) References Cited

OTHER PUBLICATIONS

Woyke, Tanja, et al. "In vitro activities and postantifungal effects of the potent dolastatin 10 derivative auristatin PHE." Antimicrobial agents and chemotherapy 45.12 (2001): 3580-3584. 25.
Shields, Robert L., et al. "High resolution mapping of the binding site on human IgG1 for FcyRI, FcyRII, FcyRIII, and FcRn and design of IgG1 variants with improved binding to the FcyR." Journal of Biological Chemistry 276.9 (2001): 6591-6604.
Yu, Tin-Wein, et al. "The biosynthetic gene cluster of the maytansinoid antitumor agent ansamitocin from Actinosynnema pretiosum." Proceedings of the National Academy of Sciences 99.12 (2002): 7968-7973.
Gillies, Robert J., et al. "MRI of the tumor microenvironment." Journal of Magnetic Resonance Imaging 16.4 (2002): 430-450.
Hudson, Peter J., and Christelle Souriau. "Engineered antibodies." Nature medicine 9.1 (2003): 129-134.
Cragg, Mark S., et al. "Complement-mediated lysis by anti-CD20 mAb correlates with segregation into lipid rafts." Blood 101.3 (2003): 1045-1052.
Doronina, Svetlana O., et al. "Development of potent monoclonal antibody auristatin conjugates for cancer therapy." Nature biotechnology 21.7 (2003): 778-784.
Francisco, Joseph A., et al. "cAC10-vcMMAE, an anti-CD30-monomethyl auristatin E conjugate with potent and selective antitumor activity." Blood 102.4 (2003): 1458-1465.
Osbourn, Jane, Maria Groves, and Tristan Vaughan. "From rodent reagents to human therapeutics using antibody guided selection." Methods 36.1 (2005): 61-68.
Kashmiri, Syed VS, et al. "SDR grafting—a new approach to antibody humanization." Methods 36.1 (2005): 25-34.
Cragg, Mark S., and Martin J. Glennie. "Antibody specificity controls in vivo effector mechanisms of anti-CD20 reagents." Blood 103.7 (2004): 2738-2743.
Dall'Acqua, William F., et al. "Antibody humanization by framework shuffling." Methods 36.1 (2005): 43-60.
Petkova, Stefka B., et al. "Enhanced half-life of genetically engineered human IgG1 antibodies in a humanized FcRn mouse model: potential application in humorally mediated autoimmune disease." International immunology 18.12 (2006): 1759-1769.
Kratz, Felix, et al. "Prodrugs of anthracyclines in cancer chemotherapy." Current medicinal chemistry 13.5 (2006): 477-523.
Flatman, Stephen, et al. "Process analytics for purification of monoclonal antibodies." Journal of Chromatography B 848.1 (2007): 79-87.
Almagro, Juan C., and Johan Fransson. "Humanization of antibodies." Front Biosci 13.1 (2008): 1619-1633.
Minami, Yasuhiro, et al. "Ror-family receptor tyrosine kinases in noncanonical Wnt signaling: Their implications in developmental morphogenesis and human diseases." Developmental Dynamics 239.1 (2010): 1-15.
Ford, Caroline E., et al. "The dual role of the novel Wnt receptor tyrosine kinase, ROR2, in human carcinogenesis." International journal of cancer 133.4 (2013): 779-787.
Chang, C. et al., "Novel conditionally active biologic anti-Axl antibody-drug conjugate demonstrates anti-tumor efficacy and improved safety profile". AACR Annual Meeting. April 16-20. 2016; New Orleans. USA—Presentation Abstract 3836.
Extended European Search Report for Application No. EP 17796915—PCT/US2017/032357; dated Apr. 10, 2019.
Communication Pursuant to Article 94(3) EPC for corresponding European U.S. Appl. No. 17/796,915; dated Nov. 19, 2019 (5 pages).
Invitation to Respond to Written Opinion for corresponding Singaporean application No. 11201808882Q; dated Mar. 4, 2020 (10 pages).
Henry, C. et al., "Targeting the ROR1 and ROR2 receptors in epithelial ovarian cancer inhibits cell migration and invasion" Oncotarget, Oct. 20, 2015, vol. 6, No. 37, pp. 40310-40326.
Second Written Opinion for corresponding Singaporean application No. 11201808882Q; Feb. 23, dated 2021 (7 pages).
Communication pursuant to Article 94(3) EPC for corresponding European application No. 17796915.1; dated Feb. 26, 2021 (8 pages).
Examination Report for corresponding Taiwanese application No. 106115891; dated May 13, 2021 (15 pages); Machine Translation.
Notice of Reasons for Refusal for corresponding Japanese application No. 2018-559715; dated May 24, 2021 (10 pages) Machine Translation.
Office Action for corresponding Canadian application No. 3,023,979; dated May 21, 2024 (5 pages).
Non-Final Office Action for U.S. Appl. No. 17/389,337; dated Jun. 21, 2024 (26 pages).
Burks, Elizabeth, et al. "In vitro scanning saturation mutagenesis of an antibody binding pocket." Proceedings of the National Academy of Sciences, USA. vol. 94 (1997): 412-417.
Office Action for Chinese application No. 201980058347.2; dated Aug. 3, 2024 (7 pages).
Office Action for Korean application No. 10-2023-7043017; dated Aug. 5, 2024 (7 pages).
Office Action for Brazilian application No. 11 2018 003535 1; dated Oct. 15, 2024 (16 pages).
Communication Pursuant to Article 94(3) issued in European application No. 2218149.0; dated Oct. 31, 2024 (6 pages).
Office Action issued in corresponding Japanese Application No. 2023-196066; dated Dec. 3, 2024 (11 pages).
Office Action issued in corresponding Korean Application No. 10-2024-7032268; dated Dec. 16, 2024 (12 pages).
Office Action for Chinese patent application No. 201980058347.2; dated Aug. 3, 2024 (7 pages).
Office Action for Korean patent application No. 10-2023-7043017; dated Aug. 5, 2024 (7 pages).
Office Action for Brazilian patent application No. 11 2018 003535 1; dated Oct. 15, 2024 (16 pages).
Office Action based on Korean Patent Application No. 10-2024-7007173; dated Jan. 14, 2025 (8 pages) Machine Translation.

* cited by examiner

There are 4 antibodies tested under each condition (i.e., 11 bars in each set of bars). The 11 bars under each condition from left to right represent respectively clones BAP048.6-2-11-Chimera-CAB, (#3949), BAP048.7-humC02D09-CAB )#3947), BAP048.7-humA03C05-CAB (#3950), and BAP048.7-humA03F01-CAB (#3948).

SEQUENCE LISTING

```
Sequence total quantity: 117
SEQ ID NO: 1              moltype = AA  length = 10
FEATURE                   Location/Qualifiers
REGION                    1..10
                          note = Synthetic sequence
VARIANT                   4
                          note = Xaa can be amino acid E or F
VARIANT                   7
                          note = Xaa can be amino acid Y or D
VARIANT                   8
                          note = Xaa can be amino acid T or C
VARIANT                   9
                          note = Xaa can be amino acid M or D or E or Y
source                    1..10
                          mol_type = protein
                          organism = synthetic construct
SEQUENCE: 1
GYTXTEXXXH                                                                10

SEQ ID NO: 2              moltype = AA  length = 17
FEATURE                   Location/Qualifiers
REGION                    1..17
                          note = Synthetic sequence
VARIANT                   1
                          note = Xaa can be amino acid G or S
VARIANT                   2
                          note = Xaa can be amino acid I or E
VARIANT                   3
                          note = Xaa can be amino acid N or C or L or V
VARIANT                   4
                          note = Xaa can be amino acid T or D or E
source                    1..17
                          mol_type = protein
                          organism = synthetic construct
SEQUENCE: 2
XXXXNNGGTG YNQKFKG                                                        17

SEQ ID NO: 3              moltype = AA  length = 16
FEATURE                   Location/Qualifiers
REGION                    1..16
                          note = Synthetic sequence 220
VARIANT                   1
                          note = Xaa can be amino acid A or I or M or S or T
VARIANT                   2
                          note = Xaa can be amino acid R or Q or H
VARIANT                   3
                          note = Xaa can be amino acid G or E
VARIANT                   5
                          note = Xaa can be amino acid L or F
VARIANT                   7
                          note = Xaa can be amino acid S or G
VARIANT                   9
                          note = Xaa can be amino acid G or D
VARIANT                   10
                          note = Xaa can be amino acid N or E
VARIANT                   14
                          note = Xaa can be amino acid D or L
VARIANT                   15
                          note = Xaa can be amino acid Y or C or T
VARIANT                   16
                          note = Xaa can be amino acid W or L
source                    1..16
                          mol_type = protein
                          organism = synthetic construct
SEQUENCE: 3
XXXSXYXYXX SYFXXX                                                         16

SEQ ID NO: 4              moltype = AA  length = 11
FEATURE                   Location/Qualifiers
REGION                    1..11
                          note = Synthetic sequence
VARIANT                   8
                          note = Xaa can be amino acid Y or E or R or T
source                    1..11
                          mol_type = protein
                          organism = synthetic construct
SEQUENCE: 4
GYSITTGXYW N                                                              11
```

```
SEQ ID NO: 5              moltype = AA  length = 16
FEATURE                   Location/Qualifiers
REGION                    1..16
                          note = Synthetic sequence
VARIANT                   8
                          note = Xaa can be amino acid K or S
source                    1..16
                          mol_type = protein
                          organism = synthetic construct
SEQUENCE: 5
YITYDGSXNY NPSLKN                                                           16

SEQ ID NO: 6              moltype = AA  length = 13
FEATURE                   Location/Qualifiers
REGION                    1..13
                          note = Synthetic sequence
VARIANT                   3
                          note = Xaa can be amino acid R or G or H or W or Y
VARIANT                   4
                          note = Xaa can be amino acid F or C or N or Q
VARIANT                   5
                          note = Xaa can be amino acid E or S
VARIANT                   6
                          note = Xaa can be amino acid G or E or F or H or M or Q or S
VARIANT                   8
                          note = Xaa can be amino acid W or A or I or P or Q or T or V
VARIANT                   9
                          note = Xaa can be amino acid Y or G or N or Q
VARIANT                   10
                          note = Xaa can be amino acid G or S or T
VARIANT                   13
                          note = Xaa can be amino acid Y or I
source                    1..13
                          mol_type = protein
                          organism = synthetic construct
SEQUENCE: 6
CSXXXXVXXX LDX                                                              13

SEQ ID NO: 7              moltype = AA  length = 10
FEATURE                   Location/Qualifiers
REGION                    1..10
                          note = Synthetic sequence
VARIANT                   6
                          note = Xaa can be amino acid V or E
VARIANT                   7
                          note = Xaa can be amino acid S or D
VARIANT                   8
                          note = Xaa can be amino acid Y or C or D
VARIANT                   10
                          note = Xaa can be amino acid H or G or L
source                    1..10
                          mol_type = protein
                          organism = synthetic construct
SEQUENCE: 7
SATSSXXXMX                                                                  10

SEQ ID NO: 8              moltype = AA  length = 7
FEATURE                   Location/Qualifiers
REGION                    1..7
                          note = Synthetic sequence
VARIANT                   1
                          note = Xaa can be amino acid G or C or H or P
source                    1..7
                          mol_type = protein
                          organism = synthetic construct
SEQUENCE: 8
XTSNLAS                                                                      7

SEQ ID NO: 9              moltype = AA  length = 10
FEATURE                   Location/Qualifiers
REGION                    1..10
                          note = Synthetic sequence
VARIANT                   2
                          note = Xaa can be amino acid Q or E
VARIANT                   3
                          note = Xaa can be amino acid R or H
VARIANT                   5
                          note = Xaa can be amino acid S or D or G or I or Q or V
```

```
VARIANT                 9
                        note = Xaa can be amino acid T or D
VARIANT                 10
                        note = Xaa can be amino acid F or D or E
source                  1..10
                        mol_type = protein
                        organism = synthetic construct
SEQUENCE: 9
QXXSYPFXX                                                                10

SEQ ID NO: 10           moltype = AA  length = 15
FEATURE                 Location/Qualifiers
REGION                  1..15
                        note = Synthetic sequence
VARIANT                 13
                        note = Xaa can be amino acid F or S or T
source                  1..15
                        mol_type = protein
                        organism = synthetic construct
SEQUENCE: 10
RASESVDRYG NSXIH                                                         15

SEQ ID NO: 11           moltype = AA  length = 7
FEATURE                 Location/Qualifiers
REGION                  1..7
                        note = Synthetic sequence
VARIANT                 1
                        note = Xaa can be amino acid R or C or D or E or W
VARIANT                 4
                        note = Xaa can be amino acid N or D
source                  1..7
                        mol_type = protein
                        organism = synthetic construct
SEQUENCE: 11
XTYXLES                                                                  7

SEQ ID NO: 12           moltype = AA  length = 10
FEATURE                 Location/Qualifiers
REGION                  1..10
                        note = Synthetic sequence
VARIANT                 3
                        note = Xaa can be amino acid T or D or I or P
VARIANT                 5
                        note = Xaa can be amino acid E or V
VARIANT                 8
                        note = Xaa can be amino acid W or T
VARIANT                 10
                        note = Xaa can be amino acid F or S
source                  1..10
                        mol_type = protein
                        organism = synthetic construct
SEQUENCE: 12
QQXNXDPXTX                                                               10

SEQ ID NO: 13           moltype = AA  length = 106
FEATURE                 Location/Qualifiers
REGION                  1..106
                        note = Synthetic sequence
source                  1..106
                        mol_type = protein
                        organism = synthetic construct
SEQUENCE: 13
QIVLTQSPAI MSASPGEKVT ITCSATSSVS YMHWFQQKPG TSPKLWIYGT SNLASGVPAR   60
FSGSGSGTSY SLTISRMEAE DAATYYCQQR SSYPFTFGQG TKVEIK                 106

SEQ ID NO: 14           moltype = AA  length = 106
FEATURE                 Location/Qualifiers
REGION                  1..106
                        note = Synthetic sequence
source                  1..106
                        mol_type = protein
                        organism = synthetic construct
SEQUENCE: 14
QIVLTQSPAI MSASPGEKVT ITCSATSSES YMHWFQQKPG TSPKLWIYHT SNLASGVPAR   60
FSGSGSGTSY SLTISRMEAE DAATYYCQQR SSYPFTFGQG TKVEIK                 106

SEQ ID NO: 15           moltype = AA  length = 106
FEATURE                 Location/Qualifiers
REGION                  1..106
```

```
                         note = Synthetic sequences
source                   1..106
                         mol_type = protein
                         organism = synthetic construct
SEQUENCE: 15
AIQLTQSPSS LSASVGDRVT ITCSATSSVS YMHWYQQKPG QAPRLLIYGT SNLASGVPDR    60
FSGSGSGTDF TLKISRVEAE DVGVYYCQQR SSYPFTFGQG TKVEIK                  106

SEQ ID NO: 16            moltype = AA  length = 106
FEATURE                  Location/Qualifiers
REGION                   1..106
                         note = Synthetic sequence
source                   1..106
                         mol_type = protein
                         organism = synthetic construct
SEQUENCE: 16
AIQLTQSPSS LSASVGDRVT ITCSATSSVS YMHWYLQKPG QSPQLLIYGT SNLASGVPDR    60
FSGSGSGTDF TLKISRVEAE DVGVYYCQQR SSYPFTFGQG TKVEIK                  106

SEQ ID NO: 17            moltype = AA  length = 111
FEATURE                  Location/Qualifiers
REGION                   1..111
                         note = Synthetic sequence
source                   1..111
                         mol_type = protein
                         organism = synthetic construct
SEQUENCE: 17
DIVLTQSPDS LAVSLGQRAT ISCRASESVD RYGNSFIHWY LQKPGQPPKL LIYRTYNLES    60
GIPARFSGTG SRTDFTLTIN PVEADDVATY YCQQTNEDPW TFGQGTKVEI K            111

SEQ ID NO: 18            moltype = AA  length = 122
FEATURE                  Location/Qualifiers
REGION                   1..122
                         note = Synthetic sequence
source                   1..122
                         mol_type = protein
                         organism = synthetic construct
SEQUENCE: 18
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCARGS LYSYGNSYFD YWGQGTLVTV   120
SS                                                                 122

SEQ ID NO: 19            moltype = AA  length = 122
FEATURE                  Location/Qualifiers
REGION                   1..122
                         note = Synthetic sequence
source                   1..122
                         mol_type = protein
                         organism = synthetic construct
SEQUENCE: 19
EVQLQQSGPE LVKPGASVKI SCKTSGYTET EDTDHWMKQS HRKSLEWIGG ENDNNGGTGY    60
NQKFKGKATL TVDKSSSTAY MELRSLTSED SAVYFCAHGS LYSYGNSYFD YWGQGTLVTV   120
SS                                                                 122

SEQ ID NO: 20            moltype = AA  length = 122
FEATURE                  Location/Qualifiers
REGION                   1..122
                         note = Synthetic sequence
source                   1..122
                         mol_type = protein
                         organism = synthetic construct
SEQUENCE: 20
QVQLVQSGAE VKKPGASVKV SCKASGYTFT EYTMHWVRQA RGQRLEWIGG INTNNGGTGY    60
NQKFKGRVTI SADKSISTAY LQWSSLKASD TAMYYCAHGS LYSYGNSYFD YWGQGTLVTV   120
SS                                                                 122

SEQ ID NO: 21            moltype = AA  length = 122
FEATURE                  Location/Qualifiers
REGION                   1..122
                         note = Synthetic sequence
source                   1..122
                         mol_type = protein
                         organism = synthetic construct
SEQUENCE: 21
EVQLVQSGAE VKKPGESLRI SCKGSGYTFT EYTMHWVRQA PGQGLEWMGG INTNNGGTGY    60
NQKFKGRVTI SADKSISTAY LQWSSLKASD TAMYYCAHGS LYSYGNSYFD YWGQGTLVTV   120
SS                                                                 122

SEQ ID NO: 22            moltype = AA  length = 122
```

```
FEATURE             Location/Qualifiers
REGION              1..122
                    note = Synthetic sequence
source              1..122
                    mol_type = protein
                    organism = synthetic construct
SEQUENCE: 22
EVQLVQSGAE VKKPGESLRI SCKGSGYTFT EYTMHWIRQS PSRGLEWLGG INTNNGGTGY    60
NQKFKGRVTI SADKSISTAY LQWSSLKASD TAMYYCAHGS LYSYGNSYFD YWGQGTLVTV   120
SS                                                                  122

SEQ ID NO: 23       moltype = AA  length = 119
FEATURE             Location/Qualifiers
REGION              1..119
                    note = Synthetic sequence
source              1..119
                    mol_type = protein
                    organism = synthetic construct
SEQUENCE: 23
DVQLQESGPG LVKPSQSLSL TCSVTGYSIT TGYYWNWIRQ FPGNKLEWMA YITYDGSKNY    60
NPSLKNRISI TRDTSKNKFF LKLNSVTSED TATYYCSRFE GVWYGLDYWG QGTLVTVSS    119

SEQ ID NO: 24       moltype = AA  length = 119
FEATURE             Location/Qualifiers
REGION              1..119
                    note = Synthetic sequence
source              1..119
                    mol_type = protein
                    organism = synthetic construct
SEQUENCE: 24
DVQLQESGPG LVKPSQSLSL TCSVTGYSIT TGYYWNWIRQ FPGNKLEWMA YITYDGSKNY    60
NPSLKNRISI TRDTSKNKFF LKLNSVTSED TATYYCSHFE GVWGGLDYWG QGTLVTVSS    119

SEQ ID NO: 25       moltype = AA  length = 119
FEATURE             Location/Qualifiers
REGION              1..119
                    note = Synthetic sequence
source              1..119
                    mol_type = protein
                    organism = synthetic construct
SEQUENCE: 25
QVQLQESGPG LVKPSQTLSL TCTVSGYSIT TGYYWNWVRQ ARGQRLEWIG YITYDGSKNY    60
NPSLKNRVTI SVDTSKNQFS LKLSSVTAAD TAVYYCSHFE GVWYGLDYWG QGTLVTVSS    119

SEQ ID NO: 26       moltype = AA  length = 119
FEATURE             Location/Qualifiers
REGION              1..119
                    note = Synthetic sequence
source              1..119
                    mol_type = protein
                    organism = synthetic construct
SEQUENCE: 26
QVQLQESGPG LVKPSQTLSL TCTVSGYSIT TGEYWNWVRQ ARGQRLEWIG YITYDGSKNY    60
NPSLKNRVTI SVDTSKNQFS LKLSSVTAAD TAVYYCSRFE GVWYGLDYWG QGTLVTVSS    119

SEQ ID NO: 27       moltype = AA  length = 111
FEATURE             Location/Qualifiers
REGION              1..111
                    note = Synthetic sequence
source              1..111
                    mol_type = protein
                    organism = synthetic construct
SEQUENCE: 27
AIQLTQSPSS LSASVGDRVT ITCRASESVD RYGNSFIHWY QQKPGKAPKL LIYRTYNLES    60
GIPARFSGSG SGTEFTLTIS SLQSEDFAVY YCQQTNEDPW TFGQGTKVEI K            111

SEQ ID NO: 28       moltype = AA  length = 119
FEATURE             Location/Qualifiers
REGION              1..119
                    note = Synthetic sequence
source              1..119
                    mol_type = protein
                    organism = synthetic construct
SEQUENCE: 28
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVWYGLDYWG QGTLVTVSS    119

SEQ ID NO: 29       moltype = AA  length = 119
FEATURE             Location/Qualifiers
```

```
REGION                    1..119
                          note = Synthetic sequence
source                    1..119
                          mol_type = protein
                          organism = synthetic construct
SEQUENCE: 29
DVQLQESGPG LVKPSQSLSL TCSVTGYSIT TGRYWNWIRQ FPGNKLEWMA YITYDGSKNY      60
NPSLKNRISI TRDTSKNKFF LKLNSVTSED TATYYCSRFE GVWYGLDYWG QGTLVTVSS      119

SEQ ID NO: 30             moltype = AA  length = 119
FEATURE                   Location/Qualifiers
REGION                    1..119
                          note = Synthetic sequence
source                    1..119
                          mol_type = protein
                          organism = synthetic construct
SEQUENCE: 30
DVQLQESGPG LVKPSQSLSL TCSVTGYSIT TGTYWNWIRQ FPGNKLEWMA YITYDGSKNY      60
NPSLKNRISI TRDTSKNKFF LKLNSVTSED TATYYCSRFE GVWYGLDYWG QGTLVTVSS      119

SEQ ID NO: 31             moltype = AA  length = 119
FEATURE                   Location/Qualifiers
REGION                    1..119
                          note = Synthetic sequence
source                    1..119
                          mol_type = protein
                          organism = synthetic construct
SEQUENCE: 31
DVQLQESGPG LVKPSQSLSL TCSVTGYSIT TGYYWNWIRQ FPGNKLEWMA YITYDGSSNY      60
NPSLKNRISI TRDTSKNKFF LKLNSVTSED TATYYCSRFE GVWYGLDYWG QGTLVTVSS      119

SEQ ID NO: 32             moltype = AA  length = 119
FEATURE                   Location/Qualifiers
REGION                    1..119
                          note = Synthetic sequence
source                    1..119
                          mol_type = protein
                          organism = synthetic construct
SEQUENCE: 32
DVQLQESGPG LVKPSQSLSL TCSVTGYSIT TGEYWNWIRQ FPGNKLEWMA YITYDGSKNY      60
NPSLKNRISI TRDTSKNKFF LKLNSVTSED TATYYCSGFE GVWYGLDYWG QGTLVTVSS      119

SEQ ID NO: 33             moltype = AA  length = 119
FEATURE                   Location/Qualifiers
REGION                    1..119
                          note = Synthetic sequence
source                    1..119
                          mol_type = protein
                          organism = synthetic construct
SEQUENCE: 33
DVQLQESGPG LVKPSQSLSL TCSVTGYSIT TGEYWNWIRQ FPGNKLEWMA YITYDGSKNY      60
NPSLKNRISI TRDTSKNKFF LKLNSVTSED TATYYCSHFE GVWYGLDYWG QGTLVTVSS      119

SEQ ID NO: 34             moltype = AA  length = 119
FEATURE                   Location/Qualifiers
REGION                    1..119
                          note = Synthetic sequence
source                    1..119
                          mol_type = protein
                          organism = synthetic construct
SEQUENCE: 34
DVQLQESGPG LVKPSQSLSL TCSVTGYSIT TGEYWNWIRQ FPGNKLEWMA YITYDGSKNY      60
NPSLKNRISI TRDTSKNKFF LKLNSVTSED TATYYCSWFE GVWYGLDYWG QGTLVTVSS      119

SEQ ID NO: 35             moltype = AA  length = 119
FEATURE                   Location/Qualifiers
REGION                    1..119
                          note = Synthetic sequence
source                    1..119
                          mol_type = protein
                          organism = synthetic construct
SEQUENCE: 35
DVQLQESGPG LVKPSQSLSL TCSVTGYSIT TGEYWNWIRQ FPGNKLEWMA YITYDGSKNY      60
NPSLKNRISI TRDTSKNKFF LKLNSVTSED TATYYCSYFE GVWYGLDYWG QGTLVTVSS      119

SEQ ID NO: 36             moltype = AA  length = 119
FEATURE                   Location/Qualifiers
REGION                    1..119
                          note = Synthetic sequence
```

```
source                          1..119
                                mol_type = protein
                                organism = synthetic construct
SEQUENCE: 36
DVQLQESGPG LVKPSQSLSL TCSVTGYSIT TGEYWNWIRQ FPGNKLEWMA YITYDGSKNY      60
NPSLKNRISI TRDTSKNKFF LKLNSVTSED TATYYCSRCE GVWYGLDYWG QGTLVTVSS      119

SEQ ID NO: 37                   moltype = AA   length = 119
FEATURE                         Location/Qualifiers
REGION                          1..119
                                note = Synthetic sequence
source                          1..119
                                mol_type = protein
                                organism = synthetic construct
SEQUENCE: 37
DVQLQESGPG LVKPSQSLSL TCSVTGYSIT TGEYWNWIRQ FPGNKLEWMA YITYDGSKNY      60
NPSLKNRISI TRDTSKNKFF LKLNSVTSED TATYYCSRNE GVWYGLDYWG QGTLVTVSS      119

SEQ ID NO: 38                   moltype = AA   length = 119
FEATURE                         Location/Qualifiers
REGION                          1..119
                                note = Synthetic sequence
source                          1..119
                                mol_type = protein
                                organism = synthetic construct
SEQUENCE: 38
DVQLQESGPG LVKPSQSLSL TCSVTGYSIT TGEYWNWIRQ FPGNKLEWMA YITYDGSKNY      60
NPSLKNRISI TRDTSKNKFF LKLNSVTSED TATYYCSRQE GVWYGLDYWG QGTLVTVSS      119

SEQ ID NO: 39                   moltype = AA   length = 119
FEATURE                         Location/Qualifiers
REGION                          1..119
                                note = Synthetic sequence
source                          1..119
                                mol_type = protein
                                organism = synthetic construct
SEQUENCE: 39
DVQLQESGPG LVKPSQSLSL TCSVTGYSIT TGEYWNWIRQ FPGNKLEWMA YITYDGSKNY      60
NPSLKNRISI TRDTSKNKFF LKLNSVTSED TATYYCSRFS GVWYGLDYWG QGTLVTVSS      119

SEQ ID NO: 40                   moltype = AA   length = 119
FEATURE                         Location/Qualifiers
REGION                          1..119
                                note = Synthetic sequence
source                          1..119
                                mol_type = protein
                                organism = synthetic construct
SEQUENCE: 40
DVQLQESGPG LVKPSQSLSL TCSVTGYSIT TGEYWNWIRQ FPGNKLEWMA YITYDGSKNY      60
NPSLKNRISI TRDTSKNKFF LKLNSVTSED TATYYCSRFE EVWYGLDYWG QGTLVTVSS      119

SEQ ID NO: 41                   moltype = AA   length = 119
FEATURE                         Location/Qualifiers
REGION                          1..119
                                note = Synthetic sequence
source                          1..119
                                mol_type = protein
                                organism = synthetic construct
SEQUENCE: 41
DVQLQESGPG LVKPSQSLSL TCSVTGYSIT TGEYWNWIRQ FPGNKLEWMA YITYDGSKNY      60
NPSLKNRISI TRDTSKNKFF LKLNSVTSED TATYYCSRFE FVWYGLDYWG QGTLVTVSS      119

SEQ ID NO: 42                   moltype = AA   length = 119
FEATURE                         Location/Qualifiers
REGION                          1..119
                                note = Synthetic sequence
source                          1..119
                                mol_type = protein
                                organism = synthetic construct
SEQUENCE: 42
DVQLQESGPG LVKPSQSLSL TCSVTGYSIT TGEYWNWIRQ FPGNKLEWMA YITYDGSKNY      60
NPSLKNRISI TRDTSKNKFF LKLNSVTSED TATYYCSRFE HVWYGLDYWG QGTLVTVSS      119

SEQ ID NO: 43                   moltype = AA   length = 119
FEATURE                         Location/Qualifiers
REGION                          1..119
                                note = Synthetic sequence
source                          1..119
                                mol_type = protein
```

```
                        organism = synthetic construct
SEQUENCE: 43
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE MVWYGLDYWG QGTLVTVSS    119

SEQ ID NO: 44           moltype = AA   length = 119
FEATURE                 Location/Qualifiers
REGION                  1..119
                        note = Synthetic sequence
source                  1..119
                        mol_type = protein
                        organism = synthetic construct
SEQUENCE: 44
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE QVWYGLDYWG QGTLVTVSS    119

SEQ ID NO: 45           moltype = AA   length = 119
FEATURE                 Location/Qualifiers
REGION                  1..119
                        note = Synthetic sequence
source                  1..119
                        mol_type = protein
                        organism = synthetic construct
SEQUENCE: 45
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE SVWYGLDYWG QGTLVTVSS    119

SEQ ID NO: 46           moltype = AA   length = 119
FEATURE                 Location/Qualifiers
REGION                  1..119
                        note = Synthetic sequence
source                  1..119
                        mol_type = protein
                        organism = synthetic construct
SEQUENCE: 46
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVAYGLDYWG QGTLVTVSS    119

SEQ ID NO: 47           moltype = AA   length = 119
FEATURE                 Location/Qualifiers
REGION                  1..119
                        note = Synthetic sequence
source                  1..119
                        mol_type = protein
                        organism = synthetic construct
SEQUENCE: 47
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVIYGLDYWG QGTLVTVSS    119

SEQ ID NO: 48           moltype = AA   length = 119
FEATURE                 Location/Qualifiers
REGION                  1..119
                        note = Synthetic sequence
source                  1..119
                        mol_type = protein
                        organism = synthetic construct
SEQUENCE: 48
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVPYGLDYWG QGTLVTVSS    119

SEQ ID NO: 49           moltype = AA   length = 119
FEATURE                 Location/Qualifiers
REGION                  1..119
                        note = Synthetic sequence
source                  1..119
                        mol_type = protein
                        organism = synthetic construct
SEQUENCE: 49
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVQYGLDYWG QGTLVTVSS    119

SEQ ID NO: 50           moltype = AA   length = 119
FEATURE                 Location/Qualifiers
REGION                  1..119
                        note = Synthetic sequence
source                  1..119
                        mol_type = protein
                        organism = synthetic construct
SEQUENCE: 50
```

```
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVTYGLDYWG QGTLVTVSS    119

SEQ ID NO: 51            moltype = AA  length = 119
FEATURE                  Location/Qualifiers
REGION                   1..119
                         note = Synthetic sequence
source                   1..119
                         mol_type = protein
                         organism = synthetic construct
SEQUENCE: 51
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVVYGLDYWG QGTLVTVSS    119

SEQ ID NO: 52            moltype = AA  length = 119
FEATURE                  Location/Qualifiers
REGION                   1..119
                         note = Synthetic sequence
source                   1..119
                         mol_type = protein
                         organism = synthetic construct
SEQUENCE: 52
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVWGGLDYWG QGTLVTVSS    119

SEQ ID NO: 53            moltype = AA  length = 119
FEATURE                  Location/Qualifiers
REGION                   1..119
                         note = Synthetic sequence
source                   1..119
                         mol_type = protein
                         organism = synthetic construct
SEQUENCE: 53
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVWNGLDYWG QGTLVTVSS    119

SEQ ID NO: 54            moltype = AA  length = 119
FEATURE                  Location/Qualifiers
REGION                   1..119
                         note = Synthetic sequence
source                   1..119
                         mol_type = protein
                         organism = synthetic construct
SEQUENCE: 54
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVWQGLDYWG QGTLVTVSS    119

SEQ ID NO: 55            moltype = AA  length = 119
FEATURE                  Location/Qualifiers
REGION                   1..119
                         note = Synthetic sequence
source                   1..119
                         mol_type = protein
                         organism = synthetic construct
SEQUENCE: 55
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVWYSLDYWG QGTLVTVSS    119

SEQ ID NO: 56            moltype = AA  length = 119
FEATURE                  Location/Qualifiers
REGION                   1..119
                         note = Synthetic sequence
source                   1..119
                         mol_type = protein
                         organism = synthetic construct
SEQUENCE: 56
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVWYTLDYWG QGTLVTVSS    119

SEQ ID NO: 57            moltype = AA  length = 119
FEATURE                  Location/Qualifiers
REGION                   1..119
                         note = Synthetic sequence
source                   1..119
                         mol_type = protein
                         organism = synthetic construct
SEQUENCE: 57
DVQLQESGPG LVKPSQSLSL TCSVTGYSIT TGEYWNWIRQ FPGNKLEWMA YITYDGSKNY    60
NPSLKNRISI TRDTSKNKFF LKLNSVTSED TATYYCSRFE GVWYGLDIWG QGTLVTVSS    119
```

```
SEQ ID NO: 58            moltype = AA  length = 122
FEATURE                  Location/Qualifiers
REGION                   1..122
                         note = Synthetic sequence
source                   1..122
                         mol_type = protein
                         organism = synthetic construct
SEQUENCE: 58
EVQLQQSGPE LVKPGASVKI SCKTSGYTET EYTMHWMKQS HRKSLEWIGG INTNNGGTGY   60
NQKFKGKATL TVDKSSSTAY MELRSLTSED SAVYFCARGS LYSYGNSYFD YWGQGTLVTV  120
SS                                                                122

SEQ ID NO: 59            moltype = AA  length = 122
FEATURE                  Location/Qualifiers
REGION                   1..122
                         note = Synthetic sequence
source                   1..122
                         mol_type = protein
                         organism = synthetic construct
SEQUENCE: 59
EVQLQQSGPE LVKPGASVKI SCKTSGYTFT EDTMHWMKQS HRKSLEWIGG INTNNGGTGY   60
NQKFKGKATL TVDKSSSTAY MELRSLTSED SAVYFCARGS LYSYGNSYFD YWGQGTLVTV  120
SS                                                                122

SEQ ID NO: 60            moltype = AA  length = 122
FEATURE                  Location/Qualifiers
REGION                   1..122
                         note = Synthetic sequence
source                   1..122
                         mol_type = protein
                         organism = synthetic construct
SEQUENCE: 60
EVQLQQSGPE LVKPGASVKI SCKTSGYTFT EYCMHWMKQS HRKSLEWIGG INTNNGGTGY   60
NQKFKGKATL TVDKSSSTAY MELRSLTSED SAVYFCARGS LYSYGNSYFD YWGQGTLVTV  120
SS                                                                122

SEQ ID NO: 61            moltype = AA  length = 122
FEATURE                  Location/Qualifiers
REGION                   1..122
                         note = Synthetic sequence
source                   1..122
                         mol_type = protein
                         organism = synthetic construct
SEQUENCE: 61
EVQLQQSGPE LVKPGASVKI SCKTSGYTFT EYTDHWMKQS HRKSLEWIGG INTNNGGTGY   60
NQKFKGKATL TVDKSSSTAY MELRSLTSED SAVYFCARGS LYSYGNSYFD YWGQGTLVTV  120
SS                                                                122

SEQ ID NO: 62            moltype = AA  length = 122
FEATURE                  Location/Qualifiers
REGION                   1..122
                         note = Synthetic sequence
source                   1..122
                         mol_type = protein
                         organism = synthetic construct
SEQUENCE: 62
EVQLQQSGPE LVKPGASVKI SCKTSGYTFT EYTEHWMKQS HRKSLEWIGG INTNNGGTGY   60
NQKFKGKATL TVDKSSSTAY MELRSLTSED SAVYFCARGS LYSYGNSYFD YWGQGTLVTV  120
SS                                                                122

SEQ ID NO: 63            moltype = AA  length = 122
FEATURE                  Location/Qualifiers
REGION                   1..122
                         note = Synthetic sequence
source                   1..122
                         mol_type = protein
                         organism = synthetic construct
SEQUENCE: 63
EVQLQQSGPE LVKPGASVKI SCKTSGYTFT EYTYHWMKQS HRKSLEWIGG INTNNGGTGY   60
NQKFKGKATL TVDKSSSTAY MELRSLTSED SAVYFCARGS LYSYGNSYFD YWGQGTLVTV  120
SS                                                                122

SEQ ID NO: 64            moltype = AA  length = 122
FEATURE                  Location/Qualifiers
REGION                   1..122
                         note = Synthetic sequence
source                   1..122
                         mol_type = protein
```

```
                        organism = synthetic construct
SEQUENCE: 64
EVQLQQSGPE LVKPGASVKI SCKTSGYTFT EYTMHWMKQS HRKSLEWIGS INTNNGGTGY    60
NQKFKGKATL TVDKSSSTAY MELRSLTSED SAVYFCARGS LYSYGNSYFD YWGQGTLVTV   120
SS                                                                 122

SEQ ID NO: 65           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 65
EVQLQQSGPE LVKPGASVKI SCKTSGYTFT EYTMHWMKQS HRKSLEWIGG ENTNNGGTGY    60
NQKFKGKATL TVDKSSSTAY MELRSLTSED SAVYFCARGS LYSYGNSYFD YWGQGTLVTV   120
SS                                                                 122

SEQ ID NO: 66           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 66
EVQLQQSGPE LVKPGASVKI SCKTSGYTFT EYTMHWMKQS HRKSLEWIGG ICTNNGGTGY    60
NQKFKGKATL TVDKSSSTAY MELRSLTSED SAVYFCARGS LYSYGNSYFD YWGQGTLVTV   120
SS                                                                 122

SEQ ID NO: 67           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 67
EVQLQQSGPE LVKPGASVKI SCKTSGYTFT EYTMHWMKQS HRKSLEWIGG ILTNNGGTGY    60
NQKFKGKATL TVDKSSSTAY MELRSLTSED SAVYFCARGS LYSYGNSYFD YWGQGTLVTV   120
SS                                                                 122

SEQ ID NO: 68           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 68
EVQLQQSGPE LVKPGASVKI SCKTSGYTFT EYTMHWMKQS HRKSLEWIGG IVTNNGGTGY    60
NQKFKGKATL TVDKSSSTAY MELRSLTSED SAVYFCARGS LYSYGNSYFD YWGQGTLVTV   120
SS                                                                 122

SEQ ID NO: 69           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 69
EVQLQQSGPE LVKPGASVKI SCKTSGYTFT EYTMHWMKQS HRKSLEWIGG INDNNGGTGY    60
NQKFKGKATL TVDKSSSTAY MELRSLTSED SAVYFCARGS LYSYGNSYFD YWGQGTLVTV   120
SS                                                                 122

SEQ ID NO: 70           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 70
EVQLQQSGPE LVKPGASVKI SCKTSGYTFT EYTMHWMKQS HRKSLEWIGG INENNGGTGY    60
NQKFKGKATL TVDKSSSTAY MELRSLTSED SAVYFCARGS LYSYGNSYFD YWGQGTLVTV   120
SS                                                                 122

SEQ ID NO: 71           moltype = AA  length = 122
```

```
FEATURE                 Location/Qualifiers
REGION                  1..122
                        note = Synthetic sequence
source                  1..122
                        mol_type = protein
                        organism = synthetic construct
SEQUENCE: 71
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCIRGS LYSYGNSYFD YWGQGTLVTV   120
SS                                                                  122

SEQ ID NO: 72           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 72
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCMRGS LYSYGNSYFD YWGQGTLVTV   120
SS                                                                  122

SEQ ID NO: 73           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 73
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCSRGS LYSYGNSYFD YWGQGTLVTV   120
SS                                                                  122

SEQ ID NO: 74           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 74
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCTRGS LYSYGNSYFD YWGQGTLVTV   120
SS                                                                  122

SEQ ID NO: 75           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 75
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCAHGS LYSYGNSYFD YWGQGTLVTV   120
SS                                                                  122

SEQ ID NO: 76           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 76
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCAQGS LYSYGNSYFD YWGQGTLVTV   120
SS                                                                  122

SEQ ID NO: 77           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 77
```

```
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCARES LYSYGNSYFD YWGQGTLVTV   120
SS                                                                 122

SEQ ID NO: 78           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 78
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCARGS FYSYGNSYFD YWGQGTLVTV   120
SS                                                                 122

SEQ ID NO: 79           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 79
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCARGS LYGYGNSYFD YWGQGTLVTV   120
SS                                                                 122

SEQ ID NO: 80           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 80
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCARGS LYSYDNSYFD YWGQGTLVTV   120
SS                                                                 122

SEQ ID NO: 81           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 81
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCARGS LYSYGESYFD YWGQGTLVTV   120
SS                                                                 122

SEQ ID NO: 82           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 82
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCARGS LYSYGNSYFL YWGQGTLVTV   120
SS                                                                 122

SEQ ID NO: 83           moltype = AA  length = 122
FEATURE                 Location/Qualifiers
REGION                  1..122
                        note = Synthetic sequence
source                  1..122
                        mol_type = protein
                        organism = synthetic construct
SEQUENCE: 83
EVQLQQSGPE LVKPGASVKI SCKTSGYTFT EYTMHWMKQS HRKSLEWIGG INTNNGGTGY    60
NQKFKGKATL TVDKSSSTAY MELRSLTSED SAVYFCARGS LYSYGNSYFD CWGQGTLVTV   120
SS                                                                 122

SEQ ID NO: 84           moltype = AA  length = 122
FEATURE                 Location/Qualifiers
REGION                  1..122
```

```
                        note = Synthetic sequence
source                  1..122
                        mol_type = protein
                        organism = synthetic construct
SEQUENCE: 84
EVQLQQSGPE LVKPGASVKI SCKTSGYTFT EYTMHWMKQS HRKSLEWIGG INTNNGGTGY   60
NQKFKGKATL TVDKSSSTAY MELRSLTSED SAVYFCARGS LYSYGNSYFD TWGQGTLVTV  120
SS                                                                 122

SEQ ID NO: 85           moltype = AA   length = 122
FEATURE                 Location/Qualifiers
REGION                  1..122
                        note = Synthetic sequence
source                  1..122
                        mol_type = protein
                        organism = synthetic construct
SEQUENCE: 85
EVQLQQSGPE LVKPGASVKI SCKTSGYTFT EYTMHWMKQS HRKSLEWIGG INTNNGGTGY   60
NQKFKGKATL TVDKSSSTAY MELRSLTSED SAVYFCARGS LYSYGNSYFD YLGQGTLVTV  120
SS                                                                 122

SEQ ID NO: 86           moltype = AA   length = 111
FEATURE                 Location/Qualifiers
REGION                  1..111
                        note = Synthetic sequence
source                  1..111
                        mol_type = protein
                        organism = synthetic construct
SEQUENCE: 86
DIVLTQSPDS LAVSLGQRAT ISCRASESVD RYGNSSIHWY LQKPGQPPKL LIYRTYNLES   60
GIPARFSGTG SRTDFTLTIN PVEADDVATY YCQQTNEDPW TFGQGTKVEI K           111

SEQ ID NO: 87           moltype = AA   length = 111
FEATURE                 Location/Qualifiers
REGION                  1..111
                        note = Synthetic sequence
source                  1..111
                        mol_type = protein
                        organism = synthetic construct
SEQUENCE: 87
DIVLTQSPDS LAVSLGQRAT ISCRASESVD RYGNSTIHWY LQKPGQPPKL LIYRTYNLES   60
GIPARFSGTG SRTDFTLTIN PVEADDVATY YCQQTNEDPW TFGQGTKVEI K           111

SEQ ID NO: 88           moltype = AA   length = 111
FEATURE                 Location/Qualifiers
REGION                  1..111
                        note = Synthetic sequence
source                  1..111
                        mol_type = protein
                        organism = synthetic construct
SEQUENCE: 88
DIVLTQSPDS LAVSLGQRAT ISCRASESVD RYGNSFIHWY LQKPGQPPKL LIYCTYNLES   60
GIPARFSGTG SRTDFTLTIN PVEADDVATY YCQQTNEDPW TFGQGTKVEI K           111

SEQ ID NO: 89           moltype = AA   length = 111
FEATURE                 Location/Qualifiers
REGION                  1..111
                        note = Synthetic sequence
source                  1..111
                        mol_type = protein
                        organism = synthetic construct
SEQUENCE: 89
DIVLTQSPDS LAVSLGQRAT ISCRASESVD RYGNSFIHWY LQKPGQPPKL LIYDTYNLES   60
GIPARFSGTG SRTDFTLTIN PVEADDVATY YCQQTNEDPW TFGQGTKVEI K           111

SEQ ID NO: 90           moltype = AA   length = 111
FEATURE                 Location/Qualifiers
REGION                  1..111
                        note = Synthetic sequence
source                  1..111
                        mol_type = protein
                        organism = synthetic construct
SEQUENCE: 90
DIVLTQSPDS LAVSLGQRAT ISCRASESVD RYGNSFIHWY LQKPGQPPKL LIYETYNLES   60
GIPARFSGTG SRTDFTLTIN PVEADDVATY YCQQTNEDPW TFGQGTKVEI K           111

SEQ ID NO: 91           moltype = AA   length = 111
FEATURE                 Location/Qualifiers
REGION                  1..111
```

```
                        note = Synthetic sequence
source                  1..111
                        mol_type = protein
                        organism = synthetic construct
SEQUENCE: 91
DIVLTQSPDS LAVSLGQRAT ISCRASESVD RYGNSFIHWY LQKPGQPPKL LIYWTYNLES    60
GIPARFSGTG SRTDFTLTIN PVEADDVATY YCQQTNEDPW TFGQGTKVEI K            111

SEQ ID NO: 92           moltype = AA  length = 111
FEATURE                 Location/Qualifiers
REGION                  1..111
                        note = Synthetic sequence
source                  1..111
                        mol_type = protein
                        organism = synthetic construct
SEQUENCE: 92
DIVLTQSPDS LAVSLGQRAT ISCRASESVD RYGNSFIHWY LQKPGQPPKL LIYRTYDLES    60
GIPARFSGTG SRTDFTLTIN PVEADDVATY YCQQTNEDPW TFGQGTKVEI K            111

SEQ ID NO: 93           moltype = AA  length = 111
FEATURE                 Location/Qualifiers
REGION                  1..111
                        note = Synthetic sequence
source                  1..111
                        mol_type = protein
                        organism = synthetic construct
SEQUENCE: 93
DIVLTQSPDS LAVSLGQRAT ISCRASESVD RYGNSFIHWY LQKPGQPPKL LIYRTYNLES    60
GIPARFSGTG SRTDFTLTIN PVEADDVATY YCQQDNEDPW TFGQGTKVEI K            111

SEQ ID NO: 94           moltype = AA  length = 111
FEATURE                 Location/Qualifiers
REGION                  1..111
                        note = Synthetic sequence
source                  1..111
                        mol_type = protein
                        organism = synthetic construct
SEQUENCE: 94
DIVLTQSPDS LAVSLGQRAT ISCRASESVD RYGNSFIHWY LQKPGQPPKL LIYRTYNLES    60
GIPARFSGTG SRTDFTLTIN PVEADDVATY YCQQINEDPW TFGQGTKVEI K            111

SEQ ID NO: 95           moltype = AA  length = 111
FEATURE                 Location/Qualifiers
REGION                  1..111
                        note = Synthetic sequence
source                  1..111
                        mol_type = protein
                        organism = synthetic construct
SEQUENCE: 95
DIVLTQSPDS LAVSLGQRAT ISCRASESVD RYGNSFIHWY LQKPGQPPKL LIYRTYNLES    60
GIPARFSGTG SRTDFTLTIN PVEADDVATY YCQQPNEDPW TFGQGTKVEI K            111

SEQ ID NO: 96           moltype = AA  length = 111
FEATURE                 Location/Qualifiers
REGION                  1..111
                        note = Synthetic sequence
source                  1..111
                        mol_type = protein
                        organism = synthetic construct
SEQUENCE: 96
DIVLTQSPDS LAVSLGQRAT ISCRASESVD RYGNSFIHWY LQKPGQPPKL LIYRTYNLES    60
GIPARFSGTG SRTDFTLTIN PVEADDVATY YCQQTNVDPW TFGQGTKVEI K            111

SEQ ID NO: 97           moltype = AA  length = 111
FEATURE                 Location/Qualifiers
REGION                  1..111
                        note = Synthetic sequence
source                  1..111
                        mol_type = protein
                        organism = synthetic construct
SEQUENCE: 97
DIVLTQSPDS LAVSLGQRAT ISCRASESVD RYGNSFIHWY LQKPGQPPKL LIYRTYNLES    60
GIPARFSGTG SRTDFTLTIN PVEADDVATY YCQQTNEDPT TFGQGTKVEI K            111

SEQ ID NO: 98           moltype = AA  length = 111
FEATURE                 Location/Qualifiers
REGION                  1..111
                        note = Synthetic sequence
source                  1..111
```

```
                            mol_type = protein
                            organism = synthetic construct
SEQUENCE: 98
DIVLTQSPDS LAVSLGQRAT ISCRASESVD RYGNSFIHWY LQKPGQPPKL LIYRTYNLES      60
GIPARFSGTG SRTDFTLTIN PVEADDVATY YCQQTNEDPW TSGQGTKVEI K              111

SEQ ID NO: 99               moltype = AA   length = 106
FEATURE                     Location/Qualifiers
REGION                      1..106
                            note = Synthetic sequence
source                      1..106
                            mol_type = protein
                            organism = synthetic construct
SEQUENCE: 99
QIVLTQSPAI MSASPGEKVT ITCSATSSES YMHWFQQKPG TSPKLWIYGT SNLASGVPAR      60
FSGSGSGTSY SLTISRMEAE DAATYYCQQR SSYPFTFGQG TKVEIK                    106

SEQ ID NO: 100              moltype = AA   length = 106
FEATURE                     Location/Qualifiers
REGION                      1..106
                            note = Synthetic sequence
source                      1..106
                            mol_type = protein
                            organism = synthetic construct
SEQUENCE: 100
QIVLTQSPAI MSASPGEKVT ITCSATSSVD YMHWFQQKPG TSPKLWIYGT SNLASGVPAR      60
FSGSGSGTSY SLTISRMEAE DAATYYCQQR SSYPFTFGQG TKVEIK                    106

SEQ ID NO: 101              moltype = AA   length = 106
FEATURE                     Location/Qualifiers
REGION                      1..106
                            note = Synthetic sequence
source                      1..106
                            mol_type = protein
                            organism = synthetic construct
SEQUENCE: 101
QIVLTQSPAI MSASPGEKVT ITCSATSSVS CMHWFQQKPG TSPKLWIYGT SNLASGVPAR      60
FSGSGSGTSY SLTISRMEAE DAATYYCQQR SSYPFTFGQG TKVEIK                    106

SEQ ID NO: 102              moltype = AA   length = 106
FEATURE                     Location/Qualifiers
REGION                      1..106
                            note = Synthetic sequence
source                      1..106
                            mol_type = protein
                            organism = synthetic construct
SEQUENCE: 102
QIVLTQSPAI MSASPGEKVT ITCSATSSVS DMHWFQQKPG TSPKLWIYGT SNLASGVPAR      60
FSGSGSGTSY SLTISRMEAE DAATYYCQQR SSYPFTFGQG TKVEIK                    106

SEQ ID NO: 103              moltype = AA   length = 106
FEATURE                     Location/Qualifiers
REGION                      1..106
                            note = Synthetic sequence
source                      1..106
                            mol_type = protein
                            organism = synthetic construct
SEQUENCE: 103
QIVLTQSPAI MSASPGEKVT ITCSATSSVS YMGWFQQKPG TSPKLWIYGT SNLASGVPAR      60
FSGSGSGTSY SLTISRMEAE DAATYYCQQR SSYPFTFGQG TKVEIK                    106

SEQ ID NO: 104              moltype = AA   length = 106
FEATURE                     Location/Qualifiers
REGION                      1..106
                            note = Synthetic sequence
source                      1..106
                            mol_type = protein
                            organism = synthetic construct
SEQUENCE: 104
QIVLTQSPAI MSASPGEKVT ITCSATSSVS YMLWFQQKPG TSPKLWIYGT SNLASGVPAR      60
FSGSGSGTSY SLTISRMEAE DAATYYCQQR SSYPFTFGQG TKVEIK                    106

SEQ ID NO: 105              moltype = AA   length = 106
FEATURE                     Location/Qualifiers
REGION                      1..106
                            note = Synthetic sequence
source                      1..106
                            mol_type = protein
                            organism = synthetic construct
```

```
SEQUENCE: 105
QIVLTQSPAI MSASPGEKVT ITCSATSSVS YMHWFQQKPG TSPKLWIYCT SNLASGVPAR     60
FSGSGSGTSY SLTISRMEAE DAATYYCQQR SSYPFTFGQG TKVEIK                   106

SEQ ID NO: 106          moltype = AA  length = 106
FEATURE                 Location/Qualifiers
REGION                  1..106
                        note = Synthetic sequence
source                  1..106
                        mol_type = protein
                        organism = synthetic construct
SEQUENCE: 106
QIVLTQSPAI MSASPGEKVT ITCSATSSVS YMHWFQQKPG TSPKLWIYHT SNLASGVPAR     60
FSGSGSGTSY SLTISRMEAE DAATYYCQQR SSYPFTFGQG TKVEIK                   106

SEQ ID NO: 107          moltype = AA  length = 106
FEATURE                 Location/Qualifiers
REGION                  1..106
                        note = Synthetic sequence
source                  1..106
                        mol_type = protein
                        organism = synthetic construct
SEQUENCE: 107
QIVLTQSPAI MSASPGEKVT ITCSATSSVS YMHWFQQKPG TSPKLWIYPT SNLASGVPAR     60
FSGSGSGTSY SLTISRMEAE DAATYYCQQR SSYPFTFGQG TKVEIK                   106

SEQ ID NO: 108          moltype = AA  length = 106
FEATURE                 Location/Qualifiers
REGION                  1..106
                        note = Synthetic sequence
source                  1..106
                        mol_type = protein
                        organism = synthetic construct
SEQUENCE: 108
QIVLTQSPAI MSASPGEKVT ITCSATSSVS YMHWFQQKPG TSPKLWIYGT SNLASGVPAR     60
FSGSGSGTSY SLTISRMEAE DAATYYCQER SSYPFTFGQG TKVEIK                   106

SEQ ID NO: 109          moltype = AA  length = 106
FEATURE                 Location/Qualifiers
REGION                  1..106
                        note = Synthetic sequence
source                  1..106
                        mol_type = protein
                        organism = synthetic construct
SEQUENCE: 109
QIVLTQSPAI MSASPGEKVT ITCSATSSVS YMHWFQQKPG TSPKLWIYGT SNLASGVPAR     60
FSGSGSGTSY SLTISRMEAE DAATYYCQQH SSYPFTFGQG TKVEIK                   106

SEQ ID NO: 110          moltype = AA  length = 106
FEATURE                 Location/Qualifiers
REGION                  1..106
                        note = Synthetic sequence
source                  1..106
                        mol_type = protein
                        organism = synthetic construct
SEQUENCE: 110
QIVLTQSPAI MSASPGEKVT ITCSATSSVS YMHWFQQKPG TSPKLWIYGT SNLASGVPAR     60
FSGSGSGTSY SLTISRMEAE DAATYYCQQR SDYPFTFGQG TKVEIK                   106

SEQ ID NO: 111          moltype = AA  length = 106
FEATURE                 Location/Qualifiers
REGION                  1..106
                        note = Synthetic sequence
source                  1..106
                        mol_type = protein
                        organism = synthetic construct
SEQUENCE: 111
QIVLTQSPAI MSASPGEKVT ITCSATSSVS YMHWFQQKPG TSPKLWIYGT SNLASGVPAR     60
FSGSGSGTSY SLTISRMEAE DAATYYCQQR SGYPFTFGQG TKVEIK                   106

SEQ ID NO: 112          moltype = AA  length = 106
FEATURE                 Location/Qualifiers
REGION                  1..106
                        note = Synthetic sequence
source                  1..106
                        mol_type = protein
                        organism = synthetic construct
SEQUENCE: 112
QIVLTQSPAI MSASPGEKVT ITCSATSSVS YMHWFQQKPG TSPKLWIYGT SNLASGVPAR     60
```

```
FSGSGSGTSY SLTISRMEAE DAATYYCQQR SIYPFTFGQG TKVEIK              106

SEQ ID NO: 113          moltype = AA  length = 106
FEATURE                 Location/Qualifiers
REGION                  1..106
                        note = Synthetic sequence
source                  1..106
                        mol_type = protein
                        organism = synthetic construct
SEQUENCE: 113
QIVLTQSPAI MSASPGEKVT ITCSATSSVS YMHWFQQKPG TSPKLWIYGT SNLASGVPAR  60
FSGSGSGTSY SLTISRMEAE DAATYYCQQR SQYPFTFGQG TKVEIK              106

SEQ ID NO: 114          moltype = AA  length = 106
FEATURE                 Location/Qualifiers
REGION                  1..106
                        note = Synthetic sequence
source                  1..106
                        mol_type = protein
                        organism = synthetic construct
SEQUENCE: 114
QIVLTQSPAI MSASPGEKVT ITCSATSSVS YMHWFQQKPG TSPKLWIYGT SNLASGVPAR  60
FSGSGSGTSY SLTISRMEAE DAATYYCQQR SVYPFTFGQG TKVEIK              106

SEQ ID NO: 115          moltype = AA  length = 106
FEATURE                 Location/Qualifiers
REGION                  1..106
                        note = Synthetic sequence
source                  1..106
                        mol_type = protein
                        organism = synthetic construct
SEQUENCE: 115
QIVLTQSPAI MSASPGEKVT ITCSATSSVS YMHWFQQKPG TSPKLWIYGT SNLASGVPAR  60
FSGSGSGTSY SLTISRMEAE DAATYYCQQR SSYPFDFGQG TKVEIK              106

SEQ ID NO: 116          moltype = AA  length = 106
FEATURE                 Location/Qualifiers
REGION                  1..106
                        note = Synthetic sequence
source                  1..106
                        mol_type = protein
                        organism = synthetic construct
SEQUENCE: 116
QIVLTQSPAI MSASPGEKVT ITCSATSSVS YMHWFQQKPG TSPKLWIYGT SNLASGVPAR  60
FSGSGSGTSY SLTISRMEAE DAATYYCQQR SSYPFTDGQG TKVEIK              106

SEQ ID NO: 117          moltype = AA  length = 106
FEATURE                 Location/Qualifiers
REGION                  1..106
                        note = Synthetic sequence
source                  1..106
                        mol_type = protein
                        organism = synthetic construct
SEQUENCE: 117
QIVLTQSPAI MSASPGEKVT ITCSATSSVS YMHWFQQKPG TSPKLWIYGT SNLASGVPAR  60
FSGSGSGTSY SLTISRMEAE DAATYYCQQR SSYPFTEGQG TKVEIK              106
```

ANTI-Ror2 ANTIBODIES, ANTIBODY FRAGMENTS, THEIR IMMUNOCONJUGATES AND USES THEREOF

CROSS REFERENCE TO RELATED APPLICATIONS

This application is a continuation of U.S. patent application Ser. No. 17/533,852, filed on Nov. 23, 2021, now U.S. Pat. No. 11,879,011, issued Jan. 23, 2021, which, in turn, is a continuation of U.S. patent application Ser. No. 16/088,769 filed on Sep. 26, 2018, now U.S. Pat. No. 11,254,742, issued Feb. 22, 2022, which, in turn, is a 371 continuation of International application No. PCT/US2017/032357, filed on May 12, 2017, which, in turn, claims the benefit of U.S. provisional application No. 62/447,218, filed on Jan. 17, 2017 and U.S. provisional application No. 62/335,719, filed on May 13, 2016, the entire disclosures of which are hereby incorporated by reference herein.

INCORPORATION OF SEQUENCE LISTING BY REFERENCE

The sequence listing in ST.26 XML format entitled BIAT1020USCON2.xml, created on Dec. 5, 2024, comprising 172 kilobytes, prepared according to 37 CFR 1.822 to 1.824 is incorporated herein by reference in its entirety.

FIELD OF THE DISCLOSURE

This disclosure relates anti-Ror2 antibodies, antibody fragments and immunoconjugates of such antibodies and antibody fragments and uses of the antibodies, antibody fragments and immunoconjugates in diagnostic and therapeutic methods.

BACKGROUND OF THE DISCLOSURE

Receptor tyrosine kinases (RTKs) are a family of cell surface receptors that regulate a range of normal cellular processes through ligand-controlled tyrosine kinase activity. Over the past 20 years, deregulation of RTKs has been shown to play a critical role in cancer development and progression. RTKs are now recognized as prognostic molecular biomarkers and as targets of oncology therapeutics.

Ror2, also called receptor tyrosine kinase-like orphan receptor 2, is a membrane-bound RTK that is activated by non-canonical Wnt signaling through its association with the Wnt5A glycoprotein during normal bone and cartilage development. Ror2 has only one transmembrane domain, which separates its extracellular and intracellular domains (FIG. 1). Ror2 is known to play crucial roles in the normal development of various organs and tissues. In mammals, Ror2- and Wnt5A-deficient mice exhibit similar abnormalities during developmental morphogenesis, reflecting their defects in convergent extension movements and planar cell polarity. Furthermore, mutations of the human Ror2 gene are responsible for the genetic skeletal disorders dominant brachydactyly type B and recessive Robinow syndrome. Ror2 has been found to mediate polarized cell migration and malfunction of Ror2 results in heritable skeletal disorders and tumor invasion (Minami et al., "Ror-family receptor tyrosine kinases in noncanonical Wnt signaling: their implications in developmental morphogenesis and human diseases," Dev Dyn., vol. 239, pp. 1-15, 2010).

Ror2 has also been reported to have pro-tumorigenic effects. US 2014/0322234 discloses that the expression and activity of Ror2 in various cancers is different from normal tissues. Thus, it is suggested that dysregulation of Ror2 plays a role in the pathogenesis of a variety of human cancers. US 2014/0322234 also contemplates that antibodies against Ror2 may be used in diagnosis of cancers and inhibition of cancer cell growth. For example, such antibodies may be conjugated to a cytotoxic agent that has a high degree of cytotoxicity for cancer cells expressing Ror2, such that the cytotoxic agent can effectively kill the cancer cells. The Ror2 gene may also be used in classification of cancers according to the Ror2 expression pattern in the cancers.

Ford et al. ("The dual role of the novel Wnt receptor tyrosine kinase, Ror2, in human carcinogenesis," International Journal of Cancer, vol. 133, pp. 779-787, 2013) further explores the mechanism of Ror2 in carcinogenesis. This reference discloses that Ror2 is involved in the development and progression of cancers. Specifically, Ror2 has been found to play a pivotal role in carcinogenesis of numerous cancers including colon cancer, hepatocellular carcinoma, metastatic melanoma and renal cell carcinoma. For example, Ror2 is over-expressed in osteosarcoma, melanoma, renal cell carcinoma, prostate carcinoma, squamous cell carcinomas of the head and neck and stromal tumors. Ror2 thus has the potential of being a drug target for cancer treatments by inhibition of the Wnt signaling pathway.

Further, Debebe et al., ("Ror2 as a therapeutic target in cancer," Pharmacol. Ther., vol. 50, pp. 143-148, 2015) discloses that Ror2 mediates both canonical and non-canonical signaling pathways. Ror2 is highly expressed in osteosarcoma and renal cell carcinomas, as well as in melanoma, colon cancer, squamous cell carcinoma of the head and neck, and breast cancer. In the majority of these cancer types, Ror2 expression is associated with more aggressive cancer states. Thus, this reference also suggests that Ror2 is a potential target for cancer treatment.

Though monoclonal antibodies against Ror2 are commercially available, anti-Ror2 antibodies suitable for cancer therapy have not been reported. The present invention provides anti-Ror2 antibodies or antibody fragments that are suitable for therapeutic and diagnostic use, especially for diagnosis and treatment of cancers. Some of the anti-Ror2 antibodies or antibody fragments have a higher binding affinity to Ror2 in a tumor in comparison with Ror2 present in normal tissue. These anti-Ror2 antibodies or antibody fragments of the present invention have at least comparable efficacy as well as a longer half-life, but reduced side-effects, in comparison with monoclonal anti-Ror2 antibodies known in the art. This may permit use of higher dosages of these anti-Ror2 antibodies or antibody fragments, thus providing a more effective therapeutic option without a corresponding significant increase in side effects.

SUMMARY OF THE DISCLOSURE

In one aspect, the present invention provides an isolated heavy chain variable region polypeptide that specifically binds to the Ror2 protein. The polypeptide includes three complementarity determining regions H1, H2, and H3 sequences, wherein:

the H1 sequence is GYTX$_1$TEX$_2$X$_3$X$_4$H (SEQ ID NO:1) or GYSITTGX$_{29}$YWN (SEQ ID NO:4);

the H2 sequence is X$_5$X$_6$X$_7$X$_8$NNGGTGYNQKFKG (SEQ ID NO:2) or YITYDGSX$_{30}$NYNPSLKN (SEQ ID NO:5); and the H3 sequence is $X_9X_{10}X_{11}SX_{12}YX_{13}$ $YX_{14}X_{15}$ $SYFX_{16}X_{17}X_{18}$ (SEQ ID NO:3) or $CSX_{31}X_{32}X_{33}$ $X_{34}VX_{35}X_{36}X_{37}LDX_{38}$ (SEQ ID NO:6);
wherein
$X_1$ is F or E,
$X_2$ is Y or D,
$X_3$ is T or C,
$X_4$ is M or D or E or Y,
$X_5$ is G or S,
$X_6$ is I or E,
$X_7$ is N or C or L or V,
$X_8$ is T or D or E,
$X_9$ is A or M or T,
$X_{10}$ is R or H,
$X_{11}$ is G or E,
$X_{12}$ is L or F,
$X_{13}$ is S or G,
$X_{14}$ is G or D,
$X_{15}$ is N or E,
$X_{16}$ is D or L,
$X_{17}$ is Y or C or T,
$X_{18}$ is W or L,
$X_{29}$ is Y or E or R or T,
$X_{30}$ is K or N,
$X_{31}$ is R or G or H or W or Y,
$X_{32}$ is F or C or N or Q,
$X_{33}$ is E or S,
$X_{34}$ is G or E or F or H or M or Q or S,
$X_{35}$ is W or A or I or P or Q or T or V,
$X_{36}$ is Y or G or N or Q,
$X_{37}$ is G or S or T, and
$X_{38}$ is Y or I.

In another aspect, this isolated heavy chain variable region polypeptide is combined with an isolated light chain variable region that includes three complementarity determining regions L1, L2, and L3 sequences, wherein:

the L1 sequence is $SATSSX_{19}X_{20}X_{21}MX_{22}$ (SEQ ID NO: 7)
or
$RASESVDRYGNSX_{39}IH$; (SEQ ID NO: 10)

the L2 sequence is $X_{23}TSNLAS$ (SEQ ID NO: 8)
or
$X_{40}TYX_{41}LES$; (SEQ ID NO: 11)
and the L3 sequence is $QX_{24}X_{25}SX_{26}YPFX_{27}X_{28}$ (SEQ ID NO: 9)
or
$QQX_{42}NX_{43}DPX_{44}TX_{45}$; (SEQ ID NO: 12)

wherein
$X_{19}$ is V or E,
$X_{20}$ is S or D,
$X_{21}$ is Y or C or D,
$X_{22}$ is H or G or L,
$X_{23}$ is G or C or H or P,
$X_{24}$ is Q or E,
$X_{25}$ is R or H,
$X_{26}$ is S or D or G or I or Q or V,
$X_{27}$ is T or D,
$X_{28}$ is F or D or E,
$X_{39}$ is F or S or T,
$X_{40}$ is R or C or D or E or W,
$X_{41}$ is N or D,
$X_{42}$ is T or I or P,
$X_{43}$ is E or V,
$X_{44}$ is W or T, and
$X_{45}$ is F or T.

In yet another aspect, the present invention provides an anti-Ror2 antibody or antibody fragment that includes the isolated heavy chain variable region polypeptide of the invention.

In yet another aspect, the present invention provides an immunoconjugate that includes the antibody or antibody fragment of the invention, optionally conjugated to an agent selected from a chemotherapeutic agent, a radioactive atom, a cytostatic agent and a cytotoxic agent.

In yet another aspect, the present invention provides a pharmaceutical composition that includes the polypeptide, the antibody or antibody fragment, or the immunoconjugate of the invention, together with a pharmaceutically acceptable carrier.

In yet another aspect, the present invention provides a kit for diagnosis or treatment including the polypeptide, the antibody or antibody fragment, or the immunoconjugate of the present invention.

BRIEF DESCRIPTION OF THE DRAWINGS

FIGS. 2A-2B show sequence alignments of exemplary heavy chain variable regions of anti-Ror2 antibodies of the present invention.

FIGS. 3A-3B show sequence alignments of exemplary light chain variable regions of anti-Ror2 antibodies of the present invention.

DEFINITIONS

Figure 1:
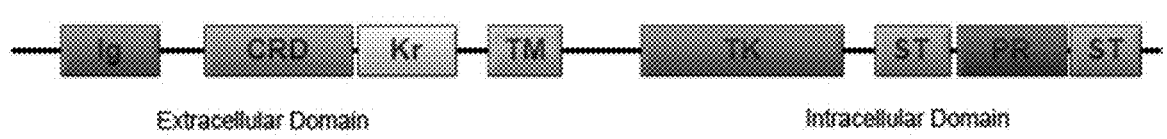
FIG. 1 is a schematic diagram of the structure of human Ror2 protein. The protein contains an Ig-like domain (Ig), a frizzled or cysteine-rich (CRD) domain, and a kringle (Kr) domain in the extracellular domain. The extracellular and intracellular domains are separated by a transmembrane (TM) domain. The intracellular domain contains a tyrosine kinase (TK) domain and a proline-rich domain (PR) flanked by serine/threonine (ST) rich domains.

In order to facilitate understanding of the examples provided herein, certain frequently occurring terms are defined herein.

In connection with a measured quantity, the term "about" as used herein refers to the normal variation in that measured quantity that would be expected by a skilled person making the measurement and exercising a level of care commensurate with the objective of the measurement and the precision of the measuring equipment used. Unless otherwise indicated, "about" refers to a variation of +/−10% of the value provided.

The term "affinity" as used herein refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "affinity matured" antibody as used herein refers to an antibody with one or more alterations in one or more hypervariable regions (HVRs), compared to a parent antibody which does not possess such alterations, such alterations resulting in an improvement in the affinity of the antibody for antigen.

The term "amino acid" as used herein refers to any organic compound that contains an amino group (—NH2) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), gluatamic acid (glu or E), glutamine (gin or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (tip or W), tyrosine (tyr or Y), and valine (val or V).

The term "antibody" as used herein refers to intact immunoglobulin molecules, as well as fragments of immunoglobulin molecules, such as Fab, Fab', (Fab')2, Fv, and SCA fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like. Chimeric, human-like, humanized or fully human antibodies are particularly useful for administration to human patients.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

An Fv fragment is defined as a genetically engineered fragment containing the variable region of a light chain and the variable region of a heavy chain expressed as two chains.

The term "antibody fragment" as used herein refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments.

The terms "anti-Ror2 antibody," "Ror2 antibody" and "an antibody that binds to Ror2" as used herein refer to an antibody that is capable of binding Ror2 with sufficient affinity such that the antibody is useful as a diagnostic and/or therapeutic agent in targeting ROr2. In one embodiment, the extent of binding of an anti-Ror2 antibody to an unrelated, non-Ror2 protein is less than about 10% of the binding of the antibody to Ror2 as measured, e.g., by a radioimmunoassay (RIA). In certain embodiments, an antibody that binds to Ror2 has a dissociation constant (Kd) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-3}$M, e.g., from $10^{-9}$M to $10^{-13}$ M). In certain embodiments, an anti-Ror2 antibody binds to an epitope of Ror2 that is conserved among Ror2 from different species.

The term "binding" as used herein refers to interaction of the variable region or an Fv of an antibody with an antigen with the interaction depending upon the presence of a particular structure (e.g., an antigenic determinant or epitope) on the antigen. For example, an antibody variable region or Fv recognizes and binds to a specific protein structure rather than to proteins generally. As used herein, the term "specifically binding" or "binding specifically" means that an antibody variable region or Fv binds to or associates with more frequently, more rapidly, with greater duration and/or with greater affinity with a particular antigen than with other proteins. For example, an antibody variable region or Fv specifically binds to its antigen with greater affinity, avidity, more readily, and/or with greater duration than it binds to other antigens. For another example, an antibody variable region or Fv binds to a cell surface protein (antigen) with materially greater affinity than it does to related proteins or other cell surface proteins or to antigens commonly recognized by polyreactive natural antibodies (i.e., by naturally occurring antibodies known to bind a variety of antigens naturally found in humans). However, "specifically binding" does not necessarily require exclusive binding or non-detectable binding of another antigen, this is meant by the term "selective binding". In one example, "specific binding" of an antibody variable region or Fv (or other binding region) binds to an antigen, means that the an antibody variable region or Fv binds to the antigen with an equilibrium constant (KD) of 100 nM or less, such as 50 nM or less, for example 20 nM or less, such as, 15 nM or less, or 10 nM or less, or 5 nM or less, 2 nM or less, or 1 nM or less.

The terms "cancer" and "cancerous" as used herein refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The terms "cell proliferative disorder" and "proliferative disorder" as used herein refer to disorders that are associated with some degree of abnormal cell proliferation. In one embodiment, the cell proliferative disorder is cancer.

The term "chemotherapeutic agent" as used herein refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem. Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), pegylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE®), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMF®); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics," which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "chimeric" antibody as used herein refers to an antibody in which a portion of the heavy and/or light chain is derived from a particular source or species, while the remainder of the heavy and/or light chain is derived from a different source or species.

The term "class" of an antibody as used herein refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called $\alpha$, $\delta$, $\epsilon$, $\gamma$, and $\mu$, respectively.

The term "conditionally active antibody" as used herein refers to an antibody which is more active under a condition in the tumor microenvironment compared to under a condition in the non-tumor microenvironment. The conditions in the tumor microenvironment include lower pH, higher concentrations of lactate and pyruvate, hypoxia, lower concentration of glucose, and slightly higher temperature in comparison with non-tumor microenvironment. For example, a conditionally active antibody is virtually inactive at normal body temperature, but is active at a higher temperature in a tumor microenvironment. In yet another aspect, the conditionally active antibody is less active in normal oxygenated blood, but more active under a less oxygenated environment exists in tumor. In yet another aspect, the conditionally active antibody is less active in normal physiological pH 7.2-7.8, but more active under an acidic pH 5.8-7.0, or 6.0-6.8 that exists in a tumor microenvironment. There are other conditions in the tumor microenvironment know to a person skilled in the field may also be used as the condition in the present invention under which the anti-Ror2 antibodies to have different binding affinity to Ror2.

The term "constitutive" as used herein, as for example applied to Ror2 activity, refers to continuous signaling activity of the receptor kinase that is not dependent on the presence of a ligand or other activating molecules. Depending on the nature of the receptor kinase, all of the activity may be constitutive or the activity of the receptor may be further activated by the binding of other molecules (e.g. ligands). Cellular events that lead to activation of receptor kinase are well known among those of ordinary skill in the art. For example, activation may include oligomerization, e.g., dimerization, trimerization, etc., into higher order receptor complexes. Complexes may comprise a single species of protein, i.e., a homomeric complex. Alternatively, complexes may comprise at least two different protein species, i.e., a heteromeric complex. Complex formation may be caused by, for example, overexpression of normal or mutant forms of receptor on the surface of a cell. Complex formation may also be caused by a specific mutation or mutations in a receptor.

The term "cytostatic agent" as used herein refers to a compound or composition which arrests growth of a cell either in vitro or in vivo. Thus, a cytostatic agent may be one which significantly reduces the percentage of cells in S phase. Further examples of cytostatic agents include agents that block cell cycle progression by inducing G0/G1 arrest or M-phase arrest. The humanized anti-Her2 antibody trastuzumab (HERCEPTIN®) is an example of a cytostatic agent that induces G0/G1 arrest. Classical M-phase blockers include the vincas (vincristine and vinblastine), taxanes, and topoisomerase II inhibitors such as doxorubicin, epirubicin, daunorubicin, etoposide, and bleomycin. Certain agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "cytotoxic agent" as used herein refers to a substance that inhibits or prevents a cellular function and/or causes cell death or destruction. Cytotoxic agents include, but are not limited to radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "diabodies" as used herein refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites.

The term "detectably label" as used herein refers to any substance whose detection or measurement, either directly or indirectly, by physical or chemical means, is indicative of the presence of the CTCs in a sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

The term "diagnostics" as used herein refers to determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy). In some embodiments, the diagnostic method of this invention is particularly useful in detecting early stage cancers.

The term "diagnostic agent" as used herein refers to a molecule which can be directly or indirectly detected and is used for diagnostic purposes. The diagnostic agent may be administered to a subject or a sample. The diagnostic agent can be provided per se or may be conjugated to a vehicle such as a conditionally active antibody.

The term "effector functions" as used herein refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "effective amount" of an agent as used herein, e.g., a pharmaceutical formulation, refers to an amount effective, at dosages and for periods of time necessary, to achieve the desired therapeutic or prophylactic result.

The term "Fc region" as used herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The term "framework" or "FR" as used herein refers to variable domain residues other than hypervariable region (HVR or H1-3 in the heavy chain and L1-3 in the light chain) residues. The FR of a variable domain generally consists of four FR domains: FR1, FR2, FR3, and FR4. Accordingly, the HVR and FR sequences generally appear in the following sequence in $V_H$ (or $V_L$): FR1-H1(L1)-FR2-H2(L2)-FR3-H3(L3)-FR4.

The term "full length antibody," "intact antibody," or "whole antibody" refers to an antibody which comprises an antigen-binding variable region ($V_H$ or $V_L$) as well as a light chain constant domain (CL) and heavy chain constant domains, CH1, CH2 and CH3. The constant domains may be native sequence constant domains (e.g. human native sequence constant domains) or amino acid sequence variants thereof. Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

The terms "host cell," "host cell line," and "host cell culture" as used herein are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "human antibody" as used herein is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "human consensus framework" as used herein is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the $V_L$, the subgroup is subgroup kappa I as in Kabat et al., supra. In one embodiment, for the $V_H$, the subgroup is subgroup III as in Kabat et al., supra.

The term "humanized" antibody as used herein refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence and/or form structurally defined loops ("hypervariable loops"). Generally, native four-chain antibodies comprise six HVRs; three in the $V_H$ (H1, H2, H3), and three in the $V_L$ (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol., vol. 196, pp. 901-917 1987) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat et al., Sequences of Proteins of Immunological Interest, 5th Ed. Public Health Service, National Institutes of Health, Bethesda, Md. 1991). With the exception of CDR1 in $V_H$, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary α-CDRs (α-CDR-L1, α-CDR-L2, α-CDR-L3, α-CDR-H1, α-CDR-H2, and α-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci., vol. 13, pp. 1619-1633, 2008). Unless otherwise indicated, HVR residues and other residues in the variable domain (e.g., FR residues) are numbered herein according to Kabat et al., supra.

The term "immunoconjugate" as used herein is an antibody conjugated to one or more heterologous molecule(s), including but not limited to a cytotoxic agent.

The term "individual" or "subject" as used herein refers to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "inhibiting cell growth or proliferation" as used herein means decreasing a cell's growth or proliferation by at least 10%, 20%, 30%, 40%, 50%, 60%, 70%, 80%, 90%, 95%, or 100%, and includes inducing cell death.

The term "isolated" antibody as used herein is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase High Performance Liquid Chromatography (HPLC)). For review of methods for assessment of antibody purity, see, e.g., Flatman et al., J. Chromatogr. B, vol. 848, pp. 79-87, 2007.

The term "isolated" nucleic acid as used herein refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "isolated nucleic acid encoding an anti-Ror2 antibody" as used herein refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "ligand-independent" as used herein, as for example applied to receptor signaling activity, refers to signaling activity that is not dependent on the presence of a ligand. A receptor having ligand-independent kinase activity will not necessarily preclude the binding of ligand to that receptor to produce additional activation of the kinase activity.

The term "metastasis" as used herein refers to all Ror2-involving processes that support cancer cells to disperse from a primary tumor, penetrate into lymphatic and/or blood vessels, circulate through the bloodstream, and grow in a distant focus (metastasis) in normal tissues elsewhere in the body. In particular, it refers to cellular events of tumor cells such as proliferation, migration, anchorage independence, evasion of apoptosis, or secretion of angiogenic factors, that underlie metastasis and are stimulated or mediated by non-catalytic or catalytic activities of Ror2, preferably including Ror2 phosphorylation and/or Ror2-mediated signal transduction.

The term "microenvironment" as used herein means any portion or region of a tissue or body that has constant or temporal, physical or chemical differences from other regions of the tissue or regions of the body. For tumors, the term "tumor microenvironment" as used herein refers to the environment in which a tumor exists, which is the non-cellular area within the tumor and the area directly outside the tumorous tissue but does not pertain to the intracellular compartment of the cancer cell itself. The tumor and the tumor microenvironment are closely related and interact constantly. A tumor can change its microenvironment, and the microenvironment can affect how a tumor grows and spreads. Typically, the tumor microenvironment has a low pH in the range of 5.8 to 7.0, more commonly in the range of 6.0 to 6.8, in the range of 6.2-6.8. On the other hand, a normal physiological pH is in the range of 7.2-7.8. The tumor microenvironment is also known to have lower concentration of glucose and other nutrients, but higher concentration of lactic acid, in comparison with blood plasma. Furthermore, the tumor microenvironment can have a temperature that is 0.3 to 1° C. higher than the normal physiological temperature. The tumor microenvironment has been discussed in Gillies et al., "MRI of the Tumor Microenvironment," *Journal of Magnetic Resonance Imaging*, vol. 16, pp. 430-450, 2002, hereby incorporated by reference herein its entirety. The term "non-tumor microenvironment" refers to a microenvironment at a site other than a tumor.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "naked antibody" as used herein refers to an antibody that is not conjugated to a heterologous moiety (e.g., a cytotoxic moiety) or radiolabel. The naked antibody may be present in a pharmaceutical formulation.

The term "native antibodies" as used herein refers to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region ($V_H$), also called a variable heavy domain or a heavy chain variable domain, followed by three constant domains (CH1, CH2, and CH3). Similarly, from N- to C-terminus, each light chain has a variable region ($V_L$), also called a variable light domain or a light chain variable domain, followed by a constant light ($C_L$) domain. The light chain of an antibody may be assigned to one of two types, called kappa (κ) and lambda (λ), based on the amino acid sequence of its constant domain.

The term "package insert" as used herein is used to refer to instructions customarily included in commercial packages of therapeutic products, that contain information about the indications, usage, dosage, administration, combination therapy, contraindications and/or warnings concerning the use of such therapeutic products.

The term "percent (%) amino acid sequence identity" with respect to a reference polypeptide sequence as used herein is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" as used herein refers to a preparation which is in such form as to permit the biological activity of an active ingredient contained therein to be effective, and which contains no additional components which are unacceptably toxic to a subject to which the formulation would be administered.

The term "pharmaceutically acceptable carrier" as used herein refers to an ingredient in a pharmaceutical formulation, other than an active ingredient, which is nontoxic to a subject., A pharmaceutically acceptable carrier includes, but is not limited to, a buffer, excipient, stabilizer, or preservative.

The terms "purified" and "isolated" used herein refer to an antibody according to the invention or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

The term "recombinant antibody" as used herein refers to an antibody (e.g. a chimeric, humanized, or human antibody or antigen-binding fragment thereof) that is expressed by a recombinant host cell comprising nucleic acid encoding the antibody. Examples of "host cells" for producing recombinant antibodies include: (1) mammalian cells, for example, Chinese Hamster Ovary (CHO), COS, myeloma cells (including Y0 and NS0 cells), baby hamster kidney (BHK), Hela and Vero cells; (2) insect cells, for example, sf9, sf21 and Tn5; (3) plant cells, for example plants belonging to the genus *Nicotiana* (e.g. *Nicotiana tabacum*); (4) yeast cells, for example, those belonging to the genus *Saccharomyces* (e.g. *Saccharomyces cerevisiae*) or the genus *Aspergillus* (e.g. *Aspergillus niger*); (5) bacterial cells, for example *Escherichia coli* cells or *Bacillus subtilis* cells, etc.

The term "Ror2" as used herein, refers to receptor tyrosine kinase-like orphan receptor 2, which is a predicted 943-amino acid protein with in vitro protein kinase activity, shown in Genbank accession number AAI30523. Many lineage-restricted receptor tyrosine kinases were initially identified as 'orphans' homologous to known receptors, and only subsequently used to identify their unknown growth factors. DeChiara et al. (2000) identified one such orphan, encoded by Ror2 as shown in FIG. 1.

The term "therapeutically effective amount" of the antibody of the invention is meant a sufficient amount of the antibody to treat said cancer, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved.

The term "single chain Fv" ("scFv") as used herein is a covalently linked $V_H$::$V_L$ heterodimer which is usually expressed from a gene fusion including $V_H$ and $V_L$ encoding genes linked by a peptide-encoding linker. "dsFv" is a $V_H$::$V_L$ heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "treatment," "treat," or "treating" as used herein refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "tumor" as used herein refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The term "variable region" or "variable domain" as used herein refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., *J. Immunol.*, vol. 150, pp. 880-887, 1993; Clarkson et al., *Nature*, vol. 352, pp. 624-628, 1991.

The term "vector" as used herein refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

DETAILED DESCRIPTION

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in, other systems and methods. Before explaining the disclosed embodiments of the present invention in detail, it is to be understood that the invention is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more", and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent, or parameter disclosed herein is to be interpreted as being disclosed for use alone or in combination with one or more of each and every other component, compound, substituent, or parameter disclosed herein.

It is also to be understood that each amount/value or range of amounts/values for each component, compound, substituent, or parameter disclosed herein is to be interpreted as also being disclosed in combination with each amount/value or range of amounts/values disclosed for any other component(s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent, or parameter disclosed in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

A. Anti-Ror2 Antibodies

In one aspect, the present invention provides an isolated heavy chain variable region polypeptide that specifically binds to human Ror2 protein. The heavy chain variable region polypeptide comprises three complementarity determining regions H1, H2, and H3 sequences, wherein:

the H1 sequence is GYTX$_1$TEX$_2$X$_3$X$_4$H (SEQ ID NO:1) or GYSITTGX$_{29}$YWN (SEQ ID NO:4);

the H2 sequence is X$_5$X$_6$X$_7$X$_8$NNGGTGYNQKFKG (SEQ ID NO:2) or YITYDGSX$_{30}$NYNPSLKN (SEQ ID NO:5); and the H3 sequence is X$_9$X$_{10}$X$_{11}$SX$_{12}$YX$_{13}$YX$_{14}$ X$_{15}$ SYFX$_{16}$X$_{17}$X$_{18}$ (SEQ ID NO:3) or CSX$_{31}$X$_{32}$X$_{33}$X$_{34}$VX$_{35}$X$_{36}$X$_{37}$LDX$_{38}$ (SEQ ID NO:6);

wherein

X$_1$ is F or E,
X$_2$ is Y or D,
X$_3$ is T or C,
X$_4$ is M or D or E or Y,
X$_5$ is G or S,
X$_6$ is I or E,
X$_7$ is N or C or L or V,
X$_8$ is T or D or E,
X$_9$ is A or M or T,
X$_{10}$ is R or H,
X$_{11}$ is G or E,
X$_{12}$ is L or F,
X$_{13}$ is S or G,
X$_{14}$ is G or D,
X$_{15}$ is N or E,
X$_{16}$ is D or L,
X$_{17}$ is Y or C or T,
X$_{18}$ is W or L,
X$_{29}$ is Y or E or R or T,
X$_{30}$ is K or N,
X$_{31}$ is R or G or H or W or Y,
X$_{32}$ is F or C or N or Q,
X$_{33}$ is E or S,
X$_{34}$ is G or E or F or H or M or Q or S,
X$_{35}$ is W or A or I or P or Q or T or V,
X$_{36}$ is Y or G or N or Q,
X$_{37}$ is G or S or T, and
X$_{38}$ is Y or I.

Figure 2A:
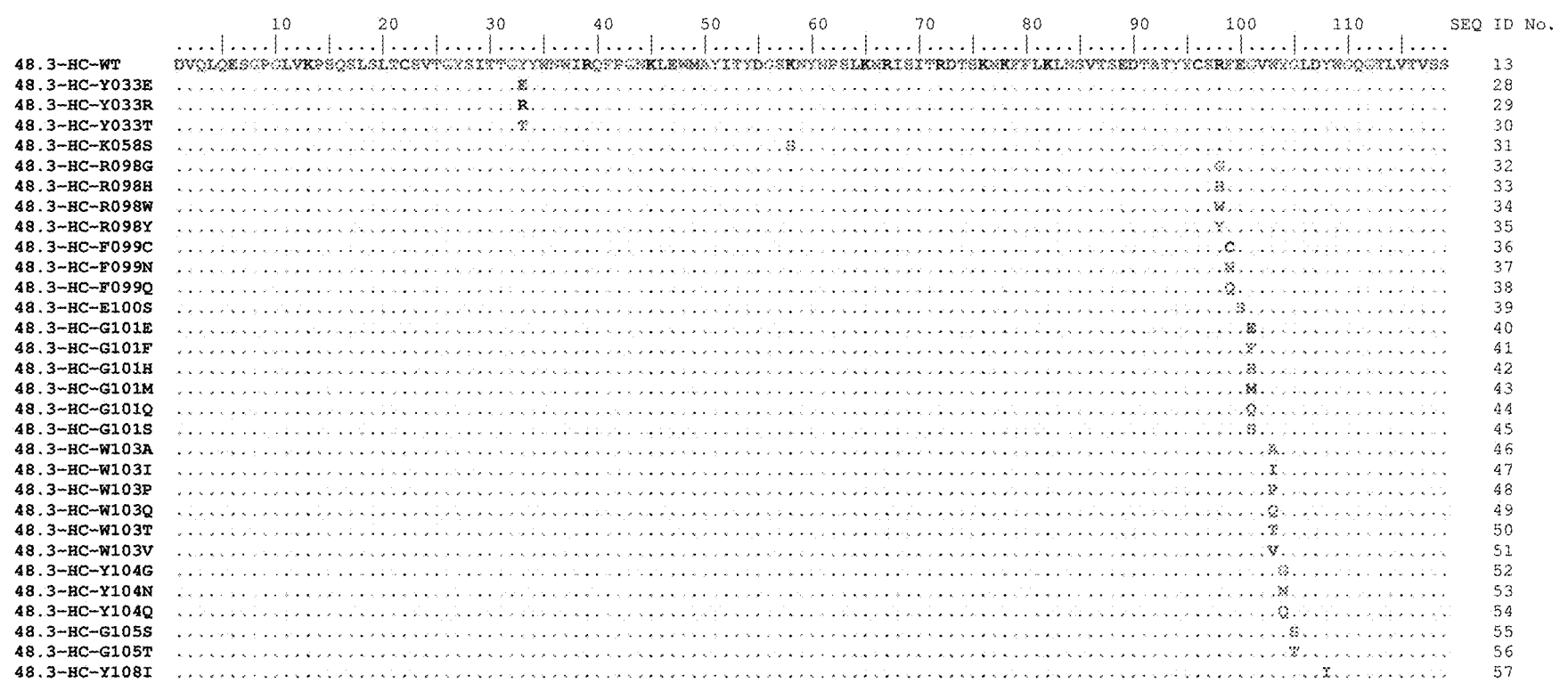
Figure 2B:
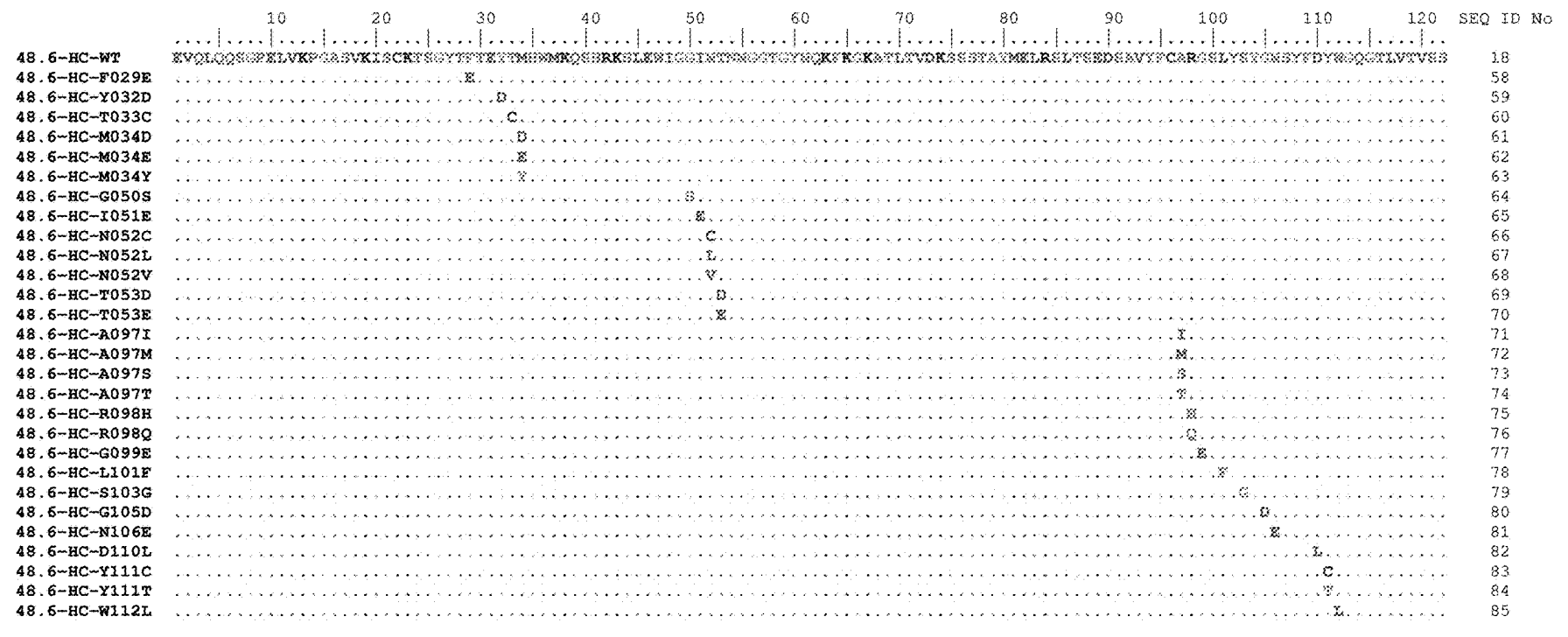

The alignment of the heavy chain variable regions is shown in FIGS. 2A-2B.

In another aspect, the present invention provides an isolated light chain variable region polypeptide that specifically binds to human Ror2 protein. The light chain variable region polypeptide comprises three complementarity determining regions L1, L2, and L3 sequences, wherein:

the L1 sequence is SATSSX$_{19}$X$_{20}$X$_{21}$MX$_{22}$ (SEQ ID NO:7) or RASESVDRYGNSX$_{39}$IH (SEQ ID NO:10);

the L2 sequence is X$_{23}$TSNLAS (SEQ ID NO:8) or X$_{40}$TYX$_{41}$LES (SEQ ID NO:11); and the L3 sequence is QX$_{24}$X$_{25}$SX$_{26}$YPFX$_{27}$X$_{28}$ (SEQ ID NO:9) or QQX$_{42}$NX$_{43}$DPX$_{44}$TX$_{45}$ (SEQ ID NO:12);

wherein

X$_{19}$ is V or E,
X$_{20}$ is S or D,
X$_{21}$ is Y or C or D,
X$_{22}$ is H or G or L,
X$_{23}$ is G or C or H or P,
X$_{24}$ is Q or E,
X$_{25}$ is R or H,
X$_{26}$ is S or D or G or I or Q or V,
X$_{27}$ is T or D,
X$_{28}$ is F or D or E,
X$_{39}$ is F or S or T,
X$_{40}$ is R or C or D or E or W,
X$_{41}$ is N or D,
X$_{42}$ is T or I or P,
X$_{43}$ is E or V,
X$_{44}$ is W or T, and
X$_{45}$ is F or T.

Figure 3A:
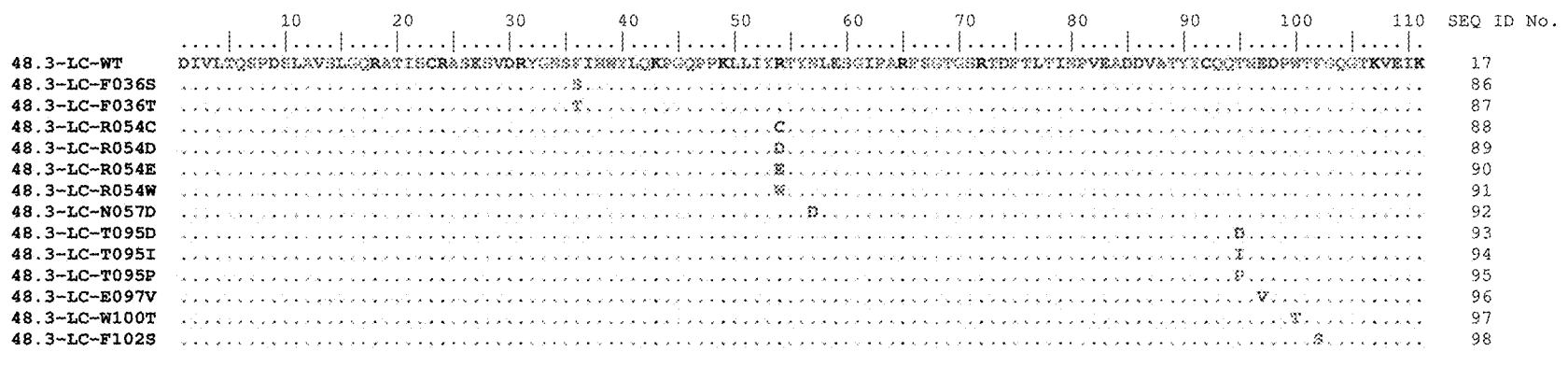
Figure 3B:
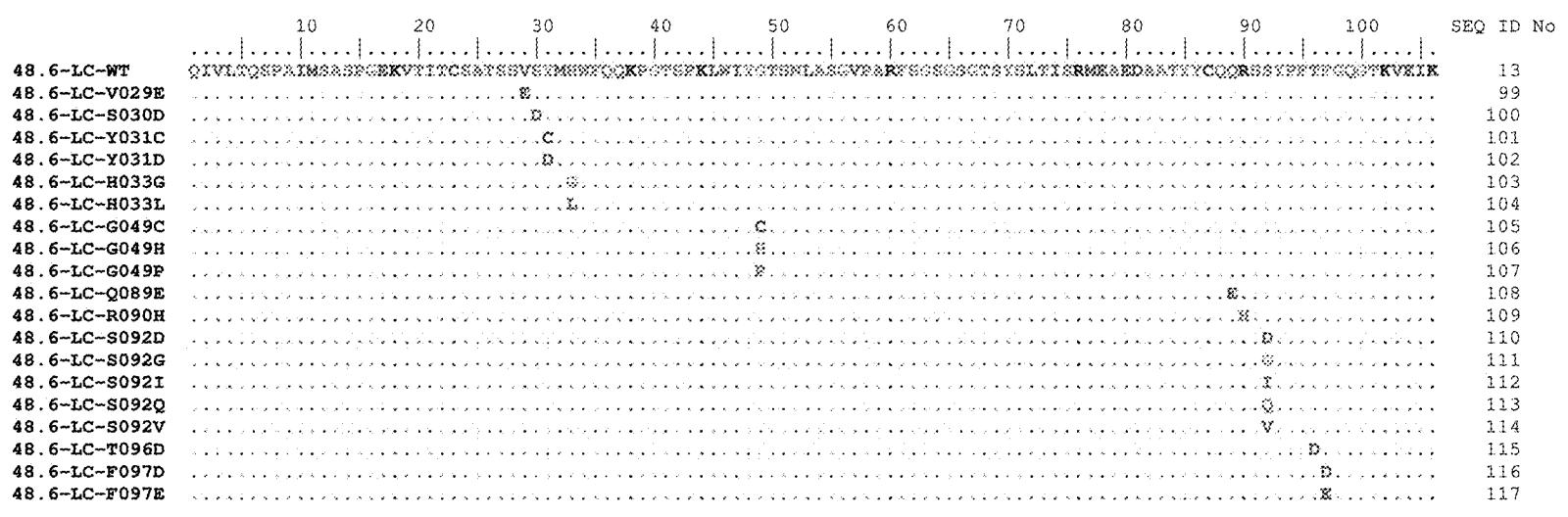

The alignment of the light chain variable regions is shown in FIGS. 3A-3B.

The present invention identified these isolated heavy chain variable regions and isolated light chain variable regions, respectively, from the heavy chain variable region and light chain variable region of a parent antibody through a method disclosed in U.S. Pat. No. 8,709,755. This method of generating a conditionally active antibody is hereby incorporated by reference herein.

The DNAs encoding the heavy chain variable region and light chain variable region the parent antibody were evolved to generate mutant antibody libraries using Comprehensive Positional Evolution (CPE), which each position in the heavy chain variable region and light chain variable region of the parent antibody is randomized one at a time. Each mutant heavy chain/light chain in the libraries has only one single point mutation, in comparison with the heavy chain variable region or light chain variable region of the parent antibody (FIGS. 2A-2B and 3A-3B). The mutants in the libraries were screened for selective binding affinity to human Ror2 at pH 6.0 over pH 7.4 by ELISA. The mutant heavy chain/light chain variable regions that are more active at pH 6.0 than at pH 7.4 were selected as the heavy chain/light chain variable regions of conditionally active antibodies, with the single point mutations indicated in each of the heavy chain and light chain variable region (Tables 1 and 2, FIGS. 2A-2B and 3A-3B).

TABLE 1

Conditionally active anti-Ror2 antibody light chain variable regions

| SEQ ID NO. | Clone | Affinity ELISA Mutants | | ratio, pH 6.0/7.4 |
|---|---|---|---|---|
| | | pH 6.0 | PH 7.4 | |
| 99 | LC-V029E | 0.406 | 0.129 | 3.15 |
| 100 | LC-S030D | 0.733 | 0.252 | 2.91 |
| 101 | LC-Y031C | 1.341 | 0.700 | 1.92 |
| 102 | LC-Y031D | 0.911 | 0.405 | 2.25 |
| 103 | LC-H033G | 1.103 | 0.536 | 2.06 |
| 104 | LC-H033L | 0.690 | 0.332 | 2.08 |
| 105 | LC G049C | 0.468 | 0.133 | 3.52 |
| 106 | LC-G049H | 1.873 | 0.118 | 15.87 |
| 107 | LC-G049P | 0.660 | 0.268 | 2.46 |
| 108 | LC-Q089E | 0.438 | 0.251 | 1.74 |
| 109 | LC-R090H | 0.560 | 0.256 | 2.19 |
| 110 | LC-S092D | 1.127 | 1.122 | 1.00 |
| 114 | LC-S092V | 1.226 | 1.182 | 1.04 |
| 115 | LC-T096D | 0.755 | 0.474 | 1.59 |
| 116 | LC-F097D | 0.190 | 0.107 | 1.77 |
| 117 | LC-F097E | 0.489 | 0.215 | 2.28 |

TABLE 2

Conditionally active anti-Ror2 antibody heavy chain variable regions

| SEQ ID NO. | Clone | Affinity ELISA mutants | | ration, pH 6.0/7.4 |
|---|---|---|---|---|
| | | pH 6.0 | pH 7.4 | |
| 58 | HC-F029E | 1.342 | 0.742 | 1.81 |
| 59 | HC-Y032D | 1.470 | 0.510 | 2.88 |
| 60 | HC-T033C | 0.626 | 0.232 | 2.70 |
| 61 | HC-M034D | 1.244 | 0.211 | 5.90 |
| 62 | HC-M034E | 1.165 | 0.185 | 6.30 |
| 63 | HC-M034Y | 0.903 | 0.391 | 2.31 |
| 64 | HC-G050S | 0.828 | 0.318 | 2.60 |
| 65 | HC-I051E | 1.039 | 0.100 | 10.39 |
| 66 | HC-N052C | 0.995 | 0.431 | 2.31 |
| 67 | HC-N052L | 0.911 | 0.433 | 2.10 |
| 68 | HC-N052V | 0.870 | 0.340 | 2.56 |
| 69 | HC-T053D | 1.108 | 0.222 | 4.99 |
| 70 | HC-T053E | 0.540 | 0.157 | 3.44 |
| 71 | HC-A097I | 1.892 | 1.730 | 1.892 |
| 72 | HC-A097M | 1.977 | 1.701 | 1.977 |
| 73 | HC-A097S | 1.666 | 1.692 | 1.666 |

TABLE 2-continued

Conditionally active anti-Ror2 antibody heavy chain variable regions

| SEQ ID NO. | Clone | Affinity ELISA mutants | | ration, pH 6.0/7.4 |
|---|---|---|---|---|
| | | pH 6.0 | pH 7.4 | |
| 74 | HC-A097T | 1.834 | 1.692 | 1.666 |
| 75 | HC-R098H | 0.928 | 0.353 | 2.63 |
| 76 | HC-R098Q | 0.799 | 0.276 | 2.89 |
| 77 | HC-G099E | 0.616 | 0.421 | 1.46 |
| 78 | HC-L101F | 1.461 | 1.412 | 1.461 |
| 79 | HC-S103G | 0.794 | 0.655 | 1.21 |
| 80 | HC-G105D | 0.509 | 0.379 | 1.34 |
| 81 | HC-N106E | 0.224 | 0.115 | 1.95 |
| 82 | HC-D110L | 1.675 | 1.403 | 1.675 |
| 83 | HC-Y111C | 1.079 | 0.793 | 1.36 |
| 84 | HC-Y111T | 1.862 | 1.403 | 1.675 |
| 85 | HC-W112L | 1.746 | 1.704 | 1.746 |

In another aspect, the present invention includes the heavy chain variable regions as represented in FIGS. 2A-2B and the light chain variable regions as presented in FIGS. 3A-3B. Amino acid sequences of the heavy chain variable regions are SEQ ID NOS: 18-26. The amino acid sequences of the light chain variable regions are SEQ ID NOS: 13-17 and 27. These heavy chain variable regions and light chain variable regions can specifically bind to human Ror2. Antibodies or antibody fragments comprising one of these heavy chain variable regions and light chain variable regions have been found to have higher binding affinity to Ror2 at a pH in the tumor microenvironment than at a pH in a non-tumor microenvironment. For example, the antibodies and antibody fragments have a higher binding affinity to Ror2 at pH 6.0 than at pH 7.4.

The anti-Ror2 antibodies or antibody fragments have a higher binding affinity to Ror2 in a tumor in comparison with their binding affinity to Ror2 in a normal tissue. These anti-Ror2 antibodies or antibody fragments have a longer half-life and reduced side-effects, as well as comparable efficacy, in comparison with monoclonal anti-Ror2 antibodies known in the art. These features permit use of a higher dosage of these anti-Ror2 antibodies or antibody fragments to be delivered to a patient thus being a more effective therapeutic option.

Though the present invention includes the heavy chain variable regions and light chain variable regions presented in FIGS. 2A-2B, 3A-3B and having amino acid sequences with SEQ ID NOS: 13-24, the present invention also provides variants thereof that can specifically bind to human Ror2. In order to derive these variants, the complementarity determining regions (CDRs) of the heavy chain variable regions (H1-H3) and the complementarity determining regions of the light chain variable regions (L1-L3) should remain intact. However, the amino acid sequence of the heavy chain variable regions and light chains variable regions outside of the complementarity determining regions may be mutated in accordance with the principles of substitution, insertion and deletion as discussed in this application.

In deriving these variants, one is guided by the process as described herein. The variants of the heavy chain variable regions and light chain variable regions may be prepared by introducing appropriate modifications into the nucleotide sequence encoding the heavy chain variable regions and light chain variable regions, or by peptide synthesis. Such modifications include, for example, deletions from, and/or insertions into and/or substitutions of residues within the amino acid sequences of the heavy chain variable regions and light chain variable regions. Any combination of deletion, insertion, and substitution can be made to arrive at the antibodies or antibody fragments of the present invention, provided that they possess the desired characteristics, e.g., antigen-binding to human Ror2 and/or conditional activity.

Substitution, Insertion, and Deletion Variants

In certain embodiments, antibody or antibody fragment variants having one or more amino acid substitutions are provided. Sites of interest for substitutional mutagenesis include the CDRs and framework regions (FRs). Conservative substitutions are shown in Table 3 under the heading of "conservative substitutions." More substantial changes are provided in Table 3 under the heading of "exemplary substitutions," and as further described below in reference to amino acid side chain classes. Amino acid substitutions may be introduced into an antibody or antibody fragment of interest and the products screened for a desired activity, e.g., retained/improved antigen binding, or decreased immunogenicity.

TABLE 3

Amino acid substitutions

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, *Methods Mol. Biol.*, vol. 207, pp. 179-196, 2008), and/or SDRs (α-CDRs), with the resulting variant VH or VL being tested for binding affinity. Affinity maturation by constructing and reselecting from secondary libraries has been described, e.g., in Hoogenboom et al. in *Methods in Molecular Biology*, vol. 178, pp. 1-37, 2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody or antibody fragment to bind antigen. For example, conservative alterations (e.g., conservative substitutions as provided herein) that do not substantially reduce binding affinity may be made in CDRs. Such alterations may be outside of CDR "hotspots" or SDRs. In certain embodiments of the variant $V_H$ and $V_L$ sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells, *Science*, vol. 244, pp. 1081-1085, 1989. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody or antibody fragment with antigen is affected. Further substitutions may be introduced at the amino acid locations demonstrating functional sensitivity to the initial substitutions. Alternatively, or additionally, a crystal structure of an antigen-antibody complex to identify contact points between the antibody or antibody fragment and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody include the fusion to the N- or C-terminus of the antibody to an enzyme (e.g. for ADEPT) or a polypeptide which increases the serum half-life of the antibody.

Amino acid sequence modification(s) of the antibodies described herein are contemplated. For example, it may be desirable to improve the binding affinity and/or other biological properties of the antibody. It is known that when a humanized antibody is produced by simply grafting only CDRs in $V_H$ and $V_L$ of an antibody derived from a non-human animal in FRs of the $V_H$ and $V_L$ of a human antibody, the antigen binding activity is reduced in comparison with that of the original antibody derived from a non-human animal. It is considered that several amino acid residues of the $V_H$ and $V_L$ of the non-human antibody, not only in CDRs but also in FRs, are directly or indirectly associated with the antigen binding activity. Hence, substitution of these amino acid residues with different amino acid residues derived from FRs of the $V_H$ and $V_L$ of the human antibody would reduce of the binding activity. In order to resolve the problem, in antibodies grafted with human CDR, attempts have to be made to identify, among amino acid sequences of the FR of the $V_H$ and $V_L$ of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further object of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the sequences of the antibodies or antibody fragments of the invention, or corresponding DNA sequences which encode said antibodies or antibody fragments, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH*, vol. 15, pp. 26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.*, vol. 336, pp. 1239-1249, 2004; Yamane-Ohnuki et al. *Biotech. Bioeng.*, vol. 87, pp. 614-622, 2004. Examples of cell lines capable of producing defucosylated antibodies include Lec13 CHO cells deficient in protein fucosylation (Ripka et al. *Arch. Biochem. Biophys.*, vol. 249, pp. 533-545, 1986; US Pat Appl No US 2003/0157108 A; and WO 2004/056312 A1, especially at Example 11), and knockout cell lines, such as alpha-1,6-fucosyltransferase gene, FUT8, knockout CHO cells (see, e.g., Yamane-Ohnuki et al. *Biotech. Bioeng.*, vol. 87, pp. 614-622, 2004; Kanda, Y. et al., *Biotechnol. Bioeng.*, vol. 94, pp. 680-688, 2006; and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.*, vol. 9, pp. 457-492, 1991. Non-limiting examples of in vitro assays to assess ADCC activity of a molecule of interest is described in U.S. Pat. No. 5,500,362 (see also, e.g. Hellstrom et al. *Proc. Nat'l Acad. Sci. USA*, vol. 83, pp. 7059-7063, 1986) and Hellstrom, I et al., *Proc. Nat'l Acad. Sci. USA*, vol. 82, pp. 1499-1502, 1985; U.S. Pat. No. 5,821,337 (see also Bruggemann et al., *J. Exp. Med.*, vol. 166, pp. 1351-1361, 1987). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA*, vol. 95, pp. 652-656, 1998. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods*, vol. 202, pp. 163-171, 1996; Cragg, M. S. et al., *Blood*, vol. 101, pp. 1045-1052, 2003; and Cragg, M. S, and M. J. Glennie, Blood, vol. 103, pp. 2738-2743, 2004). FcRn binding and in vivo clearance/half life determinations can also be performed using methods known in the art (see, e.g., Petkova, S. B. et al., *Int'l. Immunol.*, vol. 18, pp. 1759-1769, 2006).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.*, vol. 9, pp. 6591-6604, 2001).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.*, vol. 164, pp. 4178-4184, 2000.

Antibodies with increased half lives and improved binding to the neonatal Fc receptor (FcRn), which is responsible for the transfer of maternal IgGs to the fetus (Guyer et al., *J. Immunol.*, vol. 117, pp. 587-593, 1976 and Kim et al., *J. Immunol.*, vol. 24, p. 249, 1994), are described in US2005/0014934. Those antibodies comprise an Fc region with one or more substitutions therein which improve binding of the Fc region to FcRn. Such Fc variants include/e those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, Nature, vol. 322, pp. 738-740, 1988; U.S. Pat. Nos. 5,648,260; 5,624,821; and WO 94/29351 concerning other examples of Fc region variants.

Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Antibody Derivatives

In certain embodiments, an antibody or antibody fragment provided herein may be further modified to contain additional nonproteinaceous moieties that are known in the art and readily available. The moieties suitable for derivatization of the antibody or antibody fragment include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody or antibody fragment may vary, and if more than one polymer are attached, they can be the same or different molecules. In general, the number and/or type of polymers used for derivatization can be determined based on considerations including, but not limited to, the particular properties or functions of the antibody or antibody fragment to be improved, whether the derivative will be used in a therapy under defined conditions, etc.

In another embodiment, conjugates of an antibody or antibody fragment and nonproteinaceous moiety that may be selectively heated by exposure to radiation are provided. In one embodiment, the nonproteinaceous moiety is a carbon nanotube (Kam et al., Proc. Natl. Acad. Sci. USA, vol. 102, pp. 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

In another aspect, the present invention provides an anti-Ror2 antibody or antibody fragment including the isolated heavy chain variable region polypeptides or isolated light chain variable region polypeptides. The isolated heavy chain variable region polypeptides comprise the H1, H2, and H3 regions with SEQ ID NOS: 1-6. The isolated light chain variable region polypeptides comprise the L1, L2, and L3 regions with SEQ ID NOS: 7-12.

The anti-Ror2 antibody or antibody fragment of the invention has a higher binding affinity to Ror2 under a condition in tumor microenvironment than under a condition in a non-tumor microenvironment. In one embodiment, the condition in tumor microenvironment and the condition in a non-tumor microenvironment are both pH. The anti-Ror2 antibodies or antibody fragments of the invention thus can selectively bind to Ror2 at a pH about 5.of-6.8 but will have a lower binding affinity to Ror2 at a pH about 7.2-7.8 encountered in a normal physiological environment. As shown Example 1, the anti-Ror2 antibodies or antibody fragments have higher binding affinity to Ror2 at pH 6.0 that at pH 7.4.

In certain embodiments, the anti-Ror2 antibodies or antibody fragments of the present invention have a dissociation constant (Kd) with Ror2 under a condition in tumor microenvironment of about $\leq 1$ μM, $\leq 100$ nM, $\leq 10$ nM, $\leq 1$ nM, $\leq 0.1$ nM, $\leq 0.01$ nM, or $\leq 0.001$ nM (e.g. $10^{-8}$M or less, or from $10^{-8}$M to $10^{-3}$M, or from $10^{-9}$M to $10^{-13}$ M). In one embodiment, the ratio of the Kd of the antibody or antibody fragment with Ror2 at a value of the condition in tumor microenvironment to the Kd at a different value of the same condition in non-tumor microenvironment is at least about 1.5:1, at least about 2:1, at least about 3:1, at least about 4:1, at least about 5:1, at least about 6:1, at least about 7:1, at least about 8:1, at least about 9:1, at least about 10:1, at least about 20:1, at least about 30:1, at least about 50:1, at least about 70:1, or at least about 100:1.

In one embodiment, Kd is measured by a radiolabeled antigen binding assay (RIA) performed with the Fab version of an antibody of interest and its antigen using the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 μM or 26 μM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at about 10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

The anti-Ror2 antibodies of the invention may be a chimeric, humanized or human antibody. In one embodiment, an anti-Ror2 antibody fragment is employed, e.g., a Fv, Fab, Fab', Fab'-SH, scFv, a diabody, a triabody, a tetrabody or an F(ab')₂ fragment and multispecific antibodies formed from antibody fragments. In another embodiment, the antibody is a full length antibody, e.g., an intact IgG antibody or other antibody class or isotype as defined herein. For a review of certain antibody fragments, see Hudson et al. Nat. Med., vol. 9, pp. 129-134, 2003. For a review of scFv fragments, see, e.g., Plückthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')₂ fragments comprising salvage receptor binding epitope residues and having increased in vivo half-life, see U.S. Pat. No. 5,869,046.

The diabodies of the invention may be bivalent or bispecific. See, for example, EP 404,097; WO 1993/01161; Hudson et al., Nat. Med. 9:129-134 (2003); and Hollinger et al., Proc. Natl. Acad. Sci. USA, vol. 90, pp. 6444-6448, 1993 for examples of diabodies. Examples of triabodies and tetrabodies are also described in Hudson et al., Nat. Med., vol. 9, pp. 129-134, 2003.

In some embodiments, the invention comprises single-domain antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

In some embodiments, the anti-Ror2 antibodies of the invention may be chimeric antibodies. Certain chimeric antibodies are described, e.g., in U.S. Pat. No. 4,816,567; and Morrison et al., Proc. Natl. Acad. Sci. USA, vol. 81, pp. 6851-6855, 1984). In one example, the chimeric antibody comprises a non-human variable region (e.g., a variable region derived from a mouse, rat, hamster, rabbit, or non-human primate, such as a monkey) and a human constant region. In a further example, the chimeric antibody is a "class switched" antibody in which the class or subclass of the antibody has been changed relative to the class or subclass of the parent antibody. Chimeric antibodies include antigen-binding fragments thereof.

In certain embodiments, the chimeric antibody of the invention is a humanized antibody. Typically, such a non-human antibody is humanized to reduce immunogenicity to humans, while retaining the specificity and affinity of the parental non-human antibody. Generally, a humanized antibody comprises one or more variable domains in which CDRs (or portions thereof) are derived from a non-human antibody, and FRs (or portions thereof) are derived from human antibody sequences. A humanized antibody may optionally also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci., vol. 13, pp. 1619-1633, 2008, and are further described, e.g., in Riechmann et al., Nature, vol. 332, pp. 323-329, 1988; Queen et al., Proc. Nat'l Acad. Sci. USA, vol. 86, pp. 10029-10033, 1989; U.S. Pat. Nos. 5,821,337, 7,527,791, 6,982,321, and 7,087,409; Kashmiri et al., Methods, vol. 36, pp. 25-34, 2005 (describing SDR (α-CDR) grafting); Padlan, Mol. Immunol., vol. 28, pp. 489-498, 1991 (describing "resurfacing"); Dall'Acqua et al., Methods, vol. 36, pp. 43-60, 2005 (describing "FR shuffling"); and Osbourn et al., Methods, vol. 36, pp. 61-68, 2005 and Klimka et al., Br. J. Cancer, vol. 83, pp. 252-260, 2000 (describing the "guided selection" approach to FR shuffling).

Human framework regions that may be used for humanization include but are not limited to: framework regions selected using the "best-fit" method (see, e.g., Sims et al. J. Immunol., vol. 151, p. 2296, 1993); framework regions derived from the consensus sequence of human antibodies of a particular subgroup of light or heavy chain variable regions (see, e.g., Carter et al. Proc. Natl. Acad. Sci. USA, vol. 89, p. 4285, 1992; and Presta et al. J. Immunol., vol. 151, p. 2623, 1993); human mature (somatically mutated) framework regions or human germline framework regions (see, e.g., Almagro and Fransson, Front. Biosci., vol. 13, pp. 1619-1633, 2008); and framework regions derived from screening FR libraries (see, e.g., Baca et al., J. Biol. Chem., vol. 272, pp. 10678-10684, 1997 and Rosok et al., J. Biol. Chem., vol. 271, pp. 22611-22618, 1996).

In some embodiments, the anti-Ror2 antibodies of the invention are multispecific, e.g. bispecific antibodies. Multispecific antibodies are monoclonal antibodies that have binding specificities for at least two different sites. In certain embodiments, one of the binding specificities is for Ror2 and the other is for another antigen. In certain embodiments, bispecific antibodies may bind to two different epitopes of Ror2. Bispecific antibodies may also be used to localize cytotoxic agents to cells which express Ror2. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature*, vol. 305, pp. 537-540, 1983), WO 93/08829, and Traunecker et al., *EMBO J.* vol. 10, pp. 3655-3659, 1991), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); crosslinking two or more antibodies or fragments (see, e.g., U.S. Pat. No. 4,676,980, and Brennan et al., *Science*, vol. 229, pp. 81-83, 1985); using leucine zippers to produce bi-specific antibodies (see, e.g., Kostelny et al., *J. Immunol.*, vol. 148, pp. 1547-1553, 1992); using "diabody" technology for making bispecific antibody fragments (see, e.g., Hollinger et al., *Proc. Natl. Acad. Sci. USA*, vol. 90, pp. 6444-6448, 1993); and using single-chain Fv (scFv) dimers (see, e.g. Gruber et al., *J. Immunol.*, vol. 152, pp. 5368-5374, 1994); and preparing trispecific antibodies as described, e.g., in Tutt et al. *J. Immunol.*, vol. 147, pp. 60-69, 1991.

Engineered antibodies with three or more functional antigen binding sites, including "Octopus antibodies," are also included herein (see, e.g. US 2006/0025576A1).

The antibody or antibody fragment may also include a "Dual Acting Fab" or "DAF" comprising an antigen binding site that binds to Ror2 as well as another, different antigen (such as Ror1, see, US 2008/0069820, for example).

The anti-Ror2 antibodies or antibody fragments of the invention may be produced using recombinant methods and compositions, which are described in detail in US 2016/0017040.

The physical/chemical properties and/or biological activities of the anti-Ror2 antibodies or antibody fragments of the invention may be tested and measured by various assays known in the art. Some of these assays are described in U.S. Pat. No. 8,853,369.

B. Immunoconjugates

In another aspect, the invention also provides immunoconjugates comprising an anti-Ror2 antibody or antibody fragment conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, the immunoconjugate is an antibody-drug conjugate (ADC) in which an antibody or antibody fragment is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.*, vol. 53, pp. 3336-3342, 1993; and Lode et al., *Cancer Res.*, vol. 58, pp. 2925-2928, 1998); an anthracycline such as daunomycin or doxorubicin (see Kratz et al., *Current Med. Chem.*, vol. 13, pp. 477-523, 2006; Jeffrey et al., *Bioorganic & Med. Chem. Letters*, vol. 16, pp. 358-362, 2006; Torgov et al., *Bioconj. Chem.*, vol. 16, pp. 717-721, 2005; Nagy et al., *Proc. Natl. Acad. Sci. USA*, vol. 97, pp. 829-834, 2000; Dubowchik et al., *Bioorg. & Med. Chem. Letters*, vol. 12, vol. 1529-1532, 2002; King et al., *J. Med. Chem.*, vol. 45, pp. 4336-4343, 2002; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody or antibody fragment as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody or antibody fragment as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody/antibody fragment and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, vol. 238, pp. 1098-, 1987. Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.*, vol. 52, pp. 127-131, 1992; U.S. Pat. No. 5,208,020) may be used.

The immunuoconjugates herein expressly contemplate, but are not limited to conjugates prepared with cross-linker reagents including, but not limited to, BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

An exemplary embodiment of an ADC comprises an antibody or antibody fragment (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I as $Ab-(L-D)_p$, where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon et al., *Methods in Enzym.*, vol. 502, pp. 123-138, 2012). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a) Exemplary Linkers

A "Linker" (L) is a bifunctional or multifunctional moiety that can be used to link one or more moieties such as drug moieties (D) to an antibody or antibody fragment (Ab) to form an immunoconjugate such as an ADC of the Formula I. In some embodiments, ADCs can be prepared using a Linker having reactive functionalities for covalently attaching to the drug and to the antibody. For example, in some embodiments, a cysteine thiol of an antibody or antibody fragment (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, u-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al, *Bioconjugate Chemistry*, vol. 15, pp. 765-773, 2004.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl)cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., *Cancer Research*, vol. 52, pp. 127-131, 1992; U.S. Pat. No. 5,208,020).

In certain embodiments, a linker has the following Formula II as -$A_a$-$W_w$-$Y_y$-, wherein A is a "stretcher unit", and a is an integer from 0 to 1; W is an "amino acid unit", and w is an integer from 0 to 12; Y is a "spacer unit", and y is 0, 1, or 2. An ADC comprising the linker of Formula II has the Formula I(A): Ab-($A_a$-$W_w$-$Y_y$-D)$_p$, wherein Ab, D, and p are defined as above for Formula I. Exemplary embodiments of such linkers are described in U.S. Pat. No. 7,498,298.

In some embodiments, a linker component comprises a "stretcher unit" (A) that links an antibody to another linker component or to a drug moiety. Nonlimiting exemplary stretcher units are shown below (wherein the wavy line indicates sites of covalent attachment to an antibody, drug, or additional linker components):

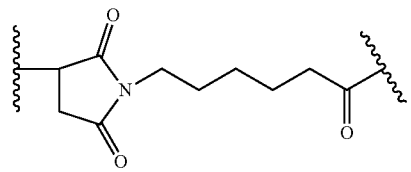

MC

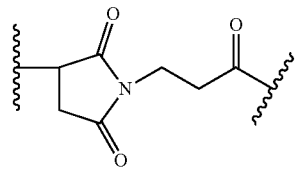

MP

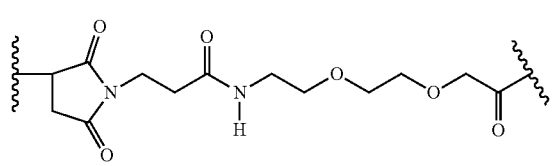

mPEG

In some embodiments, a linker component comprises an "amino acid unit" (W). In some such embodiments, the amino acid unit allows for cleavage of the linker by a protease, thereby facilitating release of the drug from the immunoconjugate upon exposure to intracellular proteases, such as lysosomal enzymes (Doronina et al., *Nat. Biotechnol.*, vol. 21, pp. 778-784, 2003). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

Typically, peptide-type linkers can be prepared by forming a peptide bond between two or more amino acids and/or peptide fragments. Such peptide bonds can be prepared, for example, according to a liquid phase synthesis method (e.g., E. Schroder and K. Lübke (1965) "The Peptides", volume 1, pp 76-136, Academic Press).

In some embodiments, a linker component comprises a "spacer unit" (Y) that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. *Expert Opin. Ther. Patents*, vol. 15, pp. 1087-1103, 2005). In some embodiments, the spacer unit comprises p-aminobenzyloxycarbonyl (PAB). In some embodiments, an ADC comprising a self-immolative linker has the structure:

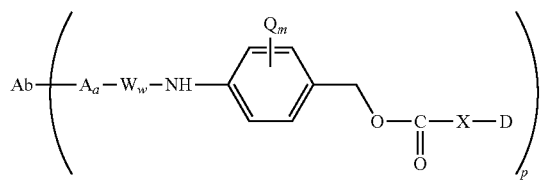

wherein Q is —$C_1$-$C_8$ alkyl, —O—($C_1$-$C_8$ alkyl), -halogen, -nitro, or -cyano; m is an integer ranging from 0 to 4; X may be one or more additional spacer units or may be absent; and p ranges from 1 to about 20. In some embodiments, p ranges from 1 to 10, 1 to 7, 1 to 5, or 1 to 4. Nonlimiting exemplary X spacer units include:

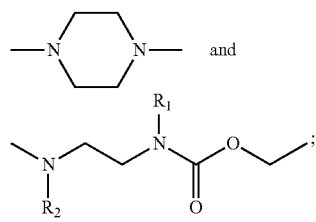

wherein $R_1$ and $R_2$ are independently selected from H and $C_1$-$C_6$ alkyl. In some embodiments, $R_1$ and $R_2$ are each —$CH_3$.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al., *Bioorg. Med. Chem. Lett.*, vol. 9, p. 2237-, 1999) and ortho- or para-aminobenzylacetals. In some embodiments, spacers can be used that undergo cyclization upon amide bond hydrolysis, such as substituted and unsubstituted 4-aminobutyric acid amides (Rodrigues et al., *Chemistry Biology*, vol. 2, pp. 223-, 1995), appropriately substituted bicyclo [2.2.1] and bicyclo[2.2.2] ring systems (Storm et al., *J. Amer. Chem. Soc.*, vol. 94, p. 5815-, 1972) and 2-aminophenyl-propionic acid amides (Amsberry et al, *J. Org. Chem.*, vol. 55, p. 5867, 1990). Linkage of a drug to the a-carbon of a glycine residue is another example of a self-immolative spacer that may be useful in ADCs (Kingsbury et al., *J. Med. Chem.*, vol. 27, p. 1447, 1984).

In some embodiments, linker L may be a dendritic type linker for covalent attachment of more than one drug moiety to an antibody through a branching, multifunctional linker moiety (Sun et al. *Bioorganic & Medicinal Chemistry Letters*, vol. 12, pp. 2213-2215, 2002; Sun et al., *Bioorganic & Medicinal Chemistry*, vol. 11, pp. 1761-1768, 2003). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below in the context of an ADC of Formula I:

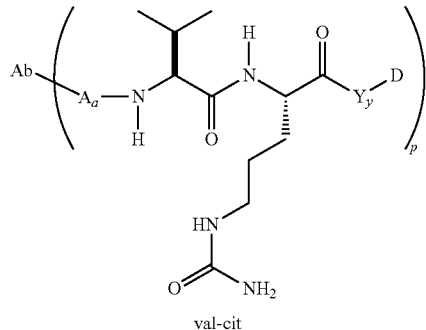
val-cit

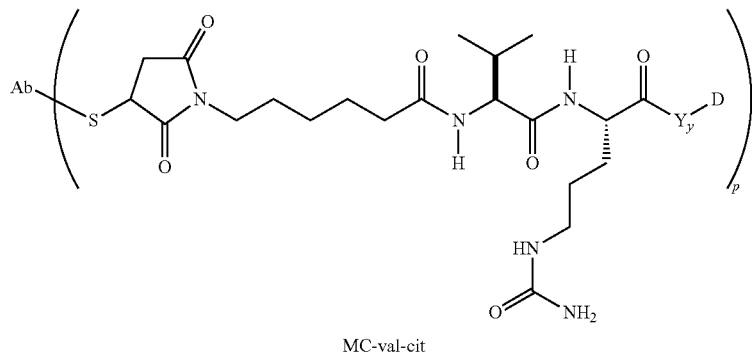
MC-val-cit

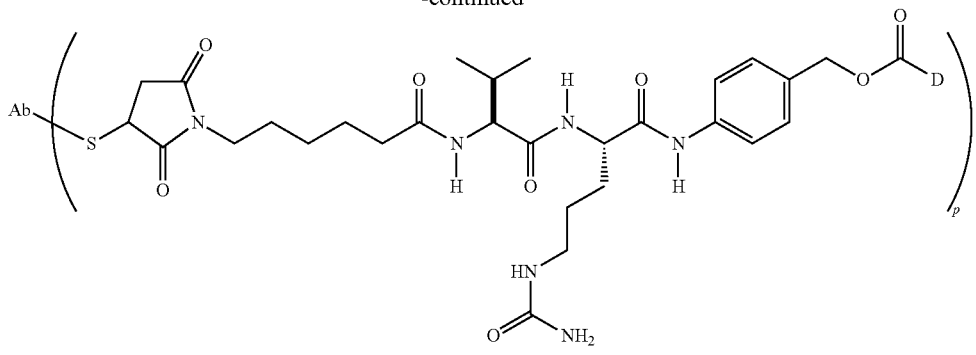
MC-val-cit-PAB
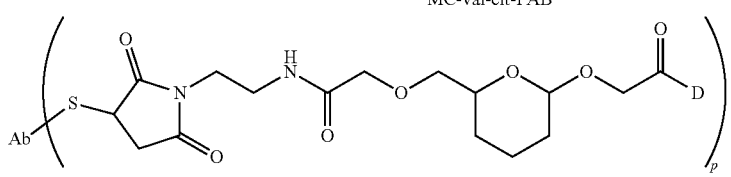
wherein $R_1$ and $R_2$ are independently selected from H and $C_1$-$C_6$ alkyl. In some embodiments, $R_1$ and $R_2$ are each —$CH_3$.
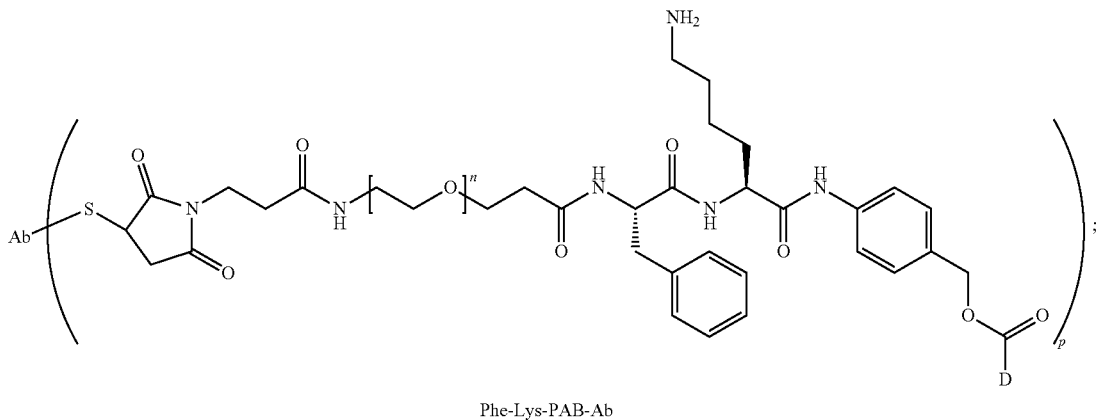
Phe-Lys-PAB-Ab
wherein n is 0 to 12. In some embodiments, n is 2 to 10. In some embodiments, n is 4 to 8.
Further nonlimiting exemplary ADCs include the structures:
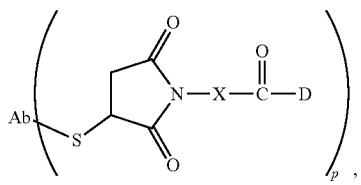
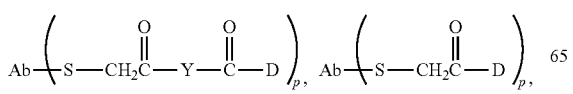
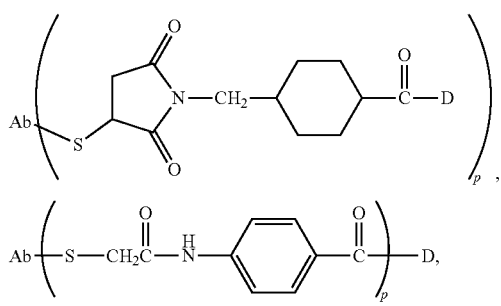
where X is:
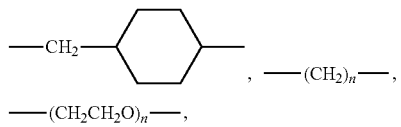

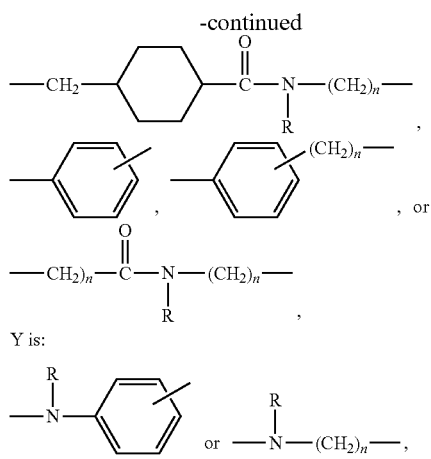

each R is independently H or $C_1$-$C_6$ alkyl; and n is 1 to 12.

In some embodiments, a linker is substituted with groups that modulate solubility and/or reactivity. As a nonlimiting example, a charged substituent such as sulfonate (—$SO_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula I.

The compounds of the invention expressly contemplate, but are not limited to, ADCs prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl) aminobenzoate (SIAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido)hexanoate](SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone)benzoate (SVSB), and including bis-maleimide reagents: dithiobismaleimidoethane (DTME), 1,4-Bismaleimidobutane (BMB), 1,4 Bismaleimidyl-2,3-dihydroxybutane (BMDB), bismaleimidohexane (BMH), bis-maleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

Certain useful linker reagents can be obtained from various commercial sources, such as Pierce Biotechnology, Inc. (Rockford, Ill.), Molecular Biosciences Inc. (Boulder, Colo.), or synthesized in accordance with procedures described in the art; for example, in Toki et al., *J. Org. Chem.*, vol. 67, pp. 1866-1872, 2002; Dubowchik, et al., *Tetrahedron Letters*, vol. 38, pp. 5257-60, 1997; Walker, *J. Org. Chem.*, vol. 60, pp. 5352-5355, 1995; Frisch et al., *Bioconjugate Chem.*, vol. 7, pp. 180-186, 1995; U.S. Pat. No. 6,214,345; WO 02/088172; US2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

b) Exemplary Drug Moieties

1) Maytansine and Maytansinoids

In some embodiments, an immunoconjugate comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al., *PNAS*, vol. 99, pp. 7968-7973, 2002). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424,219) (prepared, for example, by the reaction of maytansinol with H$_2$S or P$_2$S$_5$); C-14-alkoxymethyl(demethoxy/CH$_2$OR) (U.S. Pat. No. 4,331,598); C-14-hydroxymethyl or acyloxymethyl (CH$_2$OH or CH$_2$OAc) (U.S. Pat. No. 4,450,254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudlflora*); C-18-N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

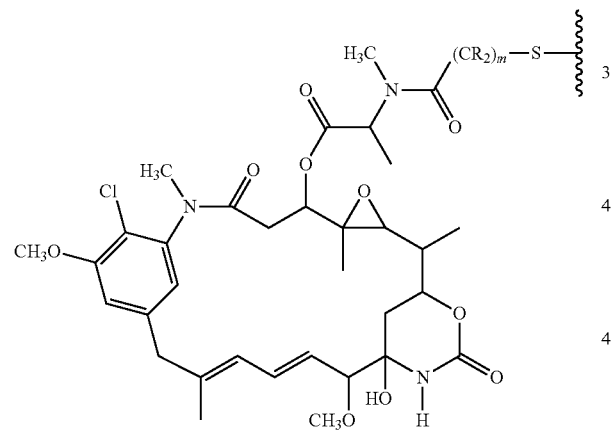

where the wavy line indicates the covalent attachment of the sulfur atom of the maytansinoid drug moiety to a linker of an ADC. Each R may independently be H or a C$_1$-C$_6$ alkyl. The alkylene chain attaching the amide group to the sulfur atom may be methanyl, ethanyl, or propyl, i.e., m is 1, 2, or 3 (U.S. Pat. No. 633,410; U.S. Pat. No. 5,208,020; Chari et al., *Cancer Res.*, vol. 52, pp. 127-131, 1992; Liu et al., *Proc. Natl. Acad. Sci. USA*, vol. 93, pp. 8618-8623, 1996).

All stereoisomers of the maytansinoid drug moiety are contemplated for the ADC of the invention, i.e. any combination of R and S configurations at the chiral carbons (U.S. Pat. Nos. 7,276,497; 6,913,748; 6,441,163; U.S. Pat. No. 633,410 (RE39151); U.S. Pat. No. 5,208,020; Widdison et al (2006) *J. Med. Chem.* 49:4392-4408. In some embodiments, the maytansinoid drug moiety has the following stereochemistry:

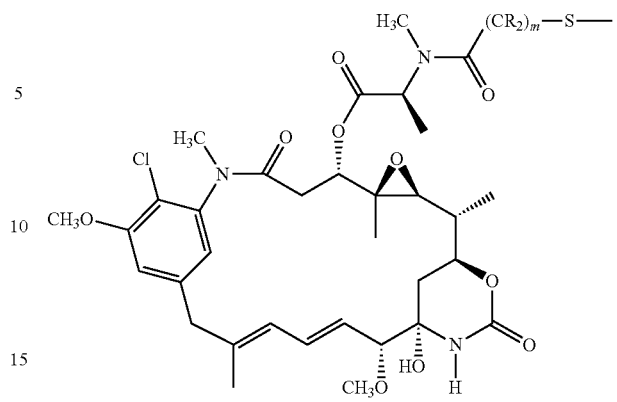

Exemplary embodiments of maytansinoid drug moieties include, but are not limited to, DM1; DM3; and DM4, having the structures:

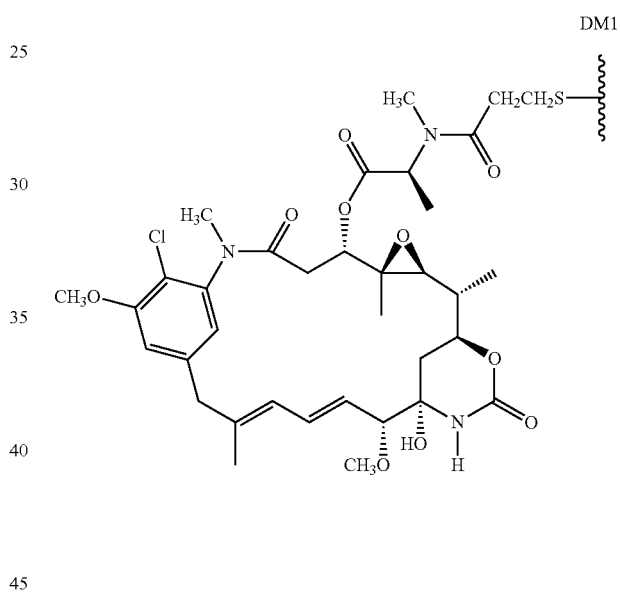

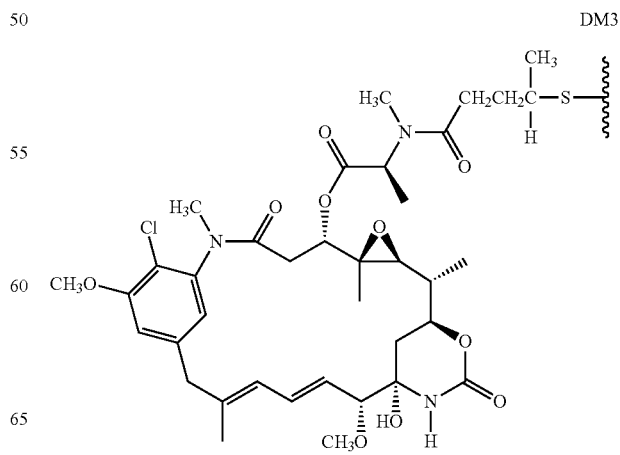

-continued

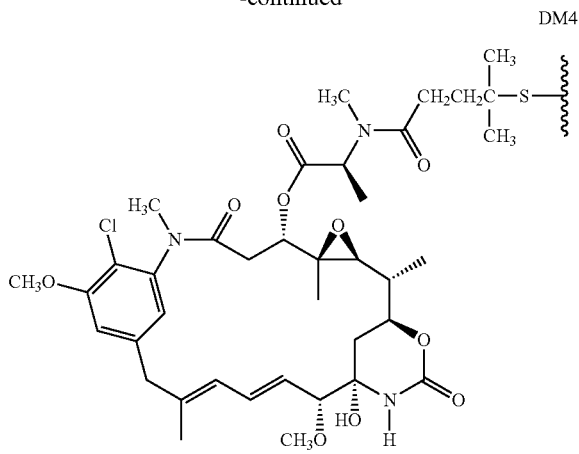

DM4 wherein the wavy line indicates the covalent attachment of the sulfur atom of the drug to a linker (L) of an antibody-drug conjugate.

Exemplary antibody-drug conjugates where DM1 is linked through a BMPEO linker to a thiol group of the antibody have the structure and abbreviation:

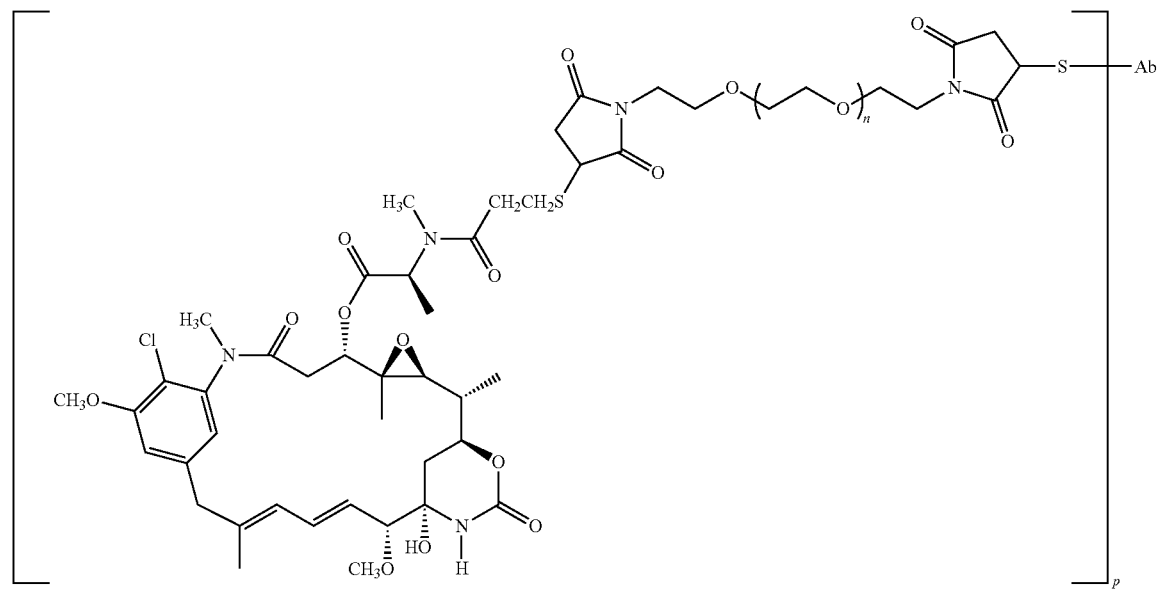

where Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1. See also Liu et al., *Proc. Natl. Acad. Sci. USA*, vol. 93, pp. 8618-8623, 1996; and Chari et al., *Cancer Research*, vol. 52, pp. 127-131, 1992.

In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020. In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al., *Cancer Research*, vol. 52, pp. 127-131, 1992; US 2005/0276812 A1; and US 2005/016993 A1.

2) Auristatins and Dolastatins

Drug moieties include dolastatins, auristatins, and analogs and derivatives thereof (U.S. Pat. Nos. 5,635,483; 5,780,588; 5,767,237; 6,124,431). Auristatins are derivatives of the marine mollusk compound dolastatin-10. While not intending to be bound by any particular theory, dolastatins and auristatins have been shown to interfere with microtubule dynamics, GTP hydrolysis, and nuclear and cellular division (Woyke et al., *Antimicrob. Agents and Chemother.*, vol. 45, pp. 3580-3584, 2001) and have anticancer (U.S. Pat. No. 5,663,149) and antifungal activity (Pettit et al., *Antimicrob. Agents Chemother.*, vol. 42, pp. 2961-2965, 1998).

The dolastatin/auristatin drug moiety may be attached to the antibody through the N (amino) terminus or the C (carboxyl) terminus of the peptidic drug moiety (WO 02/088172; Doronina et al., *Nature Biotechnology*, vol. 21, pp. 778-784, 2003; Francisco et al., *Blood*, vol. 102, pp. 1458-1465, 2003).

Exemplary auristatin embodiments include the N-terminus linked monomethylauristatin drug moieties $D_E$ and $D_F$, disclosed in U.S. Pat. Nos. 7,498,298 and 7,659,241:

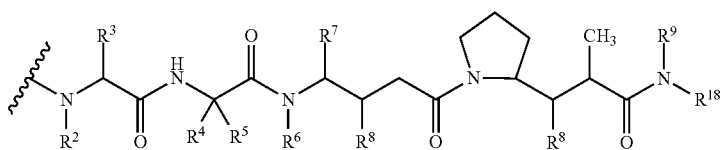

$D_E$

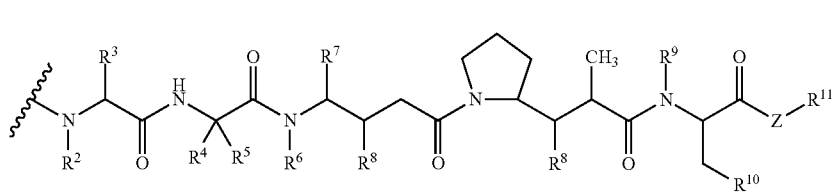

$D_F$ wherein the wavy line of $D_E$ and $D_F$ indicates the covalent attachment site to an antibody or antibody-linker component, and independently at each location:

$R^2$ is selected from H and $C_1$-$C_8$ alkyl;
$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);
$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);
$R^5$ is selected from H and methyl;
or $R^4$ and $R^5$ jointly form a carbocyclic ring and have the formula —$(CR^aR^b)_n$—
wherein $R^a$ and $R^b$ are independently selected from H, $C_1$-$C_8$ alkyl and $C_3$-$C_8$ carbocycle and n is selected from 2, 3, 4, 5 and 6;
$R^6$ is selected from H and $C_1$-$C_8$ alkyl;
$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);
each $R^8$ is independently selected from H, OH, $C_1$-$C_8$ alkyl, $C_3$-$C_8$ carbocycle and O—($C_1$-$C_8$ alkyl);
$R^9$ is selected from H and $C_1$-$C_8$ alkyl;
$R^{10}$ is selected from aryl or $C_3$-$C_8$ heterocycle;
Z is O, S, NH, or $NR^{12}$, wherein $R^{12}$ is $C_1$-$C_8$ alkyl;
$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;
m is an integer ranging from 1-1000;
$R^{13}$ is $C_2$-$C_8$ alkyl;
$R^{14}$ is H or $C_1$-$C_8$ alkyl;
each occurrence of e is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;
each occurrence of e is independently H, $C_1$-$C_8$ alkyl, or —$(CH_2)_n$—COOH;
$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and
n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.
In one embodiment, $R^{10}$ is aryl.
In an exemplary embodiment, $R^{10}$ is -phenyl.
In an exemplary embodiment, when Z is —O—, $R^{11}$ is —H, methyl or t-butyl.
In one embodiment, when Z is —NH, $R^{11}$ is —$CH(R^{15})_2$, wherein $R^{15}$ is —$(CH_2)_n$—$N(R^{16})_2$, and $R^{16}$ is —$C_1$-$C_8$ alkyl or —$(CH_2)_n$—COOH.
In another embodiment, when Z is —NH, $R^{11}$ is —$CH(R^{15})_2$, wherein $R^{15}$ is —$(CH_2)_n$—$SO_3H$.

An exemplary auristatin embodiment of formula DE is MMAE, wherein the wavy line indicates the covalent attachment to a linker (L) of an antibody-drug conjugate:

MMAE

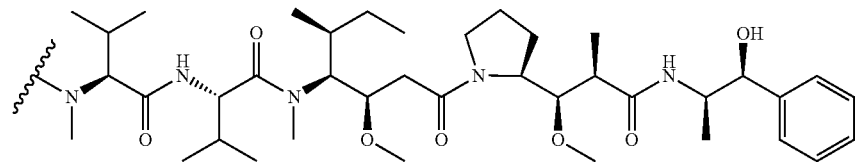

An exemplary auristatin embodiment of formula $D_E$ is MMAF, wherein the wavy line indicates the covalent attachment to a linker (L) of an antibody-drug conjugate:

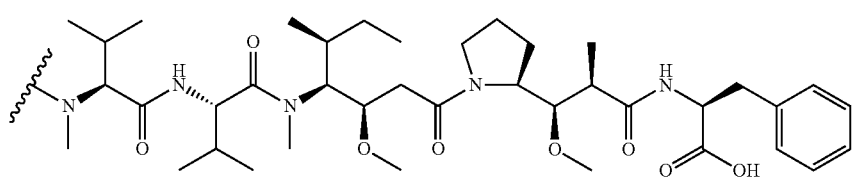

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Nonlimiting exemplary embodiments of ADCs of Formula I comprising MMAF and various linker components further include Ab-MC-PAB-MMAF and Ab-PAB-MMAF. Immunoconjugates comprising MMAF attached to an antibody by a linker that is not proteolytically cleavable have been shown to possess activity comparable to immunoconjugates comprising MMAF attached to an antibody by a proteolytically cleavable linker (Doronina et al., Bioconjugate Chem., vol. 17, pp. 114-124, 2006). In some such embodiments, drug release is believed to be effected by antibody degradation in the cell.

Typically, peptide-based drug moieties can be prepared by forming a peptide bond between two or more amino acids and/or peptide fragments. Such peptide bonds can be prepared, for example, according to a liquid phase synthesis method (see, e.g., E. Schröder and K. Lübke, "The Peptides", volume 1, pp 76-136, 1965, Academic Press). Auristatin/dolastatin drug moieties may, in some embodiments, be prepared according to the methods of: U.S. Pat. Nos. 7,498,298; 5,635,483; 5,780,588; Pettit et al., J. Am. Chem. Soc., vol. 111, pp. 5463-5465, 1998; Pettit et al., Anti-Cancer Drug Design, vol. 13, pp. 243-277, 1998; Pettit et al., Synthesis, vol. 6, pp. 719-725, 1996; Pettit et al., J. Chem. Soc. Perkin Trans. vol. 15, pp. 859-863, 1996; and Doronina, Nat. Biotechnol., vol. 21, pp. 778-784, 2003.

In some embodiments, auristatin/dolastatin drug moieties of formulas $D_E$ such as MMAE, and DE, such as MMAF, and drug-linker intermediates and derivatives thereof, such as MC-MMAF, MC-MMAE, MC-vc-PAB-MMAF, and MC-vc-PAB-MMAE, may be prepared using methods described in U.S. Pat. No. 7,498,298; Doronina et al., Bioconjugate Chem., vol. 17, pp. 114-124, 2006; and Doronina et al., Nat. Biotech., vol. 21, pp. 778-784, 2003 and then conjugated to an antibody of interest.

3) Calicheamicin

In some embodiments, the immunoconjugate comprises an antibody or antibody fragment conjugated to one or more calicheamicin molecules. The calicheamicin family of antibiotics, and analogues thereof, are capable of producing double-stranded DNA breaks at sub-picomolar concentrations (Hinman et al., Cancer Research, vol. 53, pp. 3336-3342, 1993; Lode et al., Cancer Research, vol. 58, pp. 2925-2928, 1998). Calicheamicin has intracellular sites of action but, in certain instances, does not readily cross the plasma membrane. Therefore, cellular uptake of these agents through antibody-mediated internalization may, in some embodiments, greatly enhance their cytotoxic effects. Nonlimiting exemplary methods of preparing antibody-drug conjugates with a calicheamicin drug moiety are described, for example, in U.S. Pat. Nos. 5,712,374; 5,714,586; 5,739,116; and 5,767,285.

4) Pyrrolobenzodiazepines

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber et al., J. Am. Chem. Soc., vol. 87, pp. 5793-5795, 1965; Leimgruber et al., J. Am. Chem. Soc., vol. 87, pp. 5791-5793, 1965). Since then, a number of PBDs, both naturally-occurring and analogues, have been reported (Thurston et al., Chem. Rev. vol. 1994, pp. 433-465 1994, including dimers of the tricyclic PBD scaffold (U.S. Pat. Nos. 6,884,799; 7,049,311; 7,067,511; 7,265,105; 7,511,032; 7,528,126; 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, Acc. Chem. Res., vol. 19, pp. 230-237, 1986). Dimeric PBD compounds bearing C2 aryl substituents have been shown to be useful as cytotoxic agents (Hartley et al Cancer Res., vol. 70, pp. 6849-6858, 2010; Antonow, J. Med. Chem.vol. 53, pp. 2927-2941, 2010; Howard et al., Bioorganic and Med. Chem. Letters, vol. 19, pp. 6463-6466, 2009).

PBD dimers have been conjugated to antibodies and the resulting ADC shown to have anti-cancer properties. Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of:

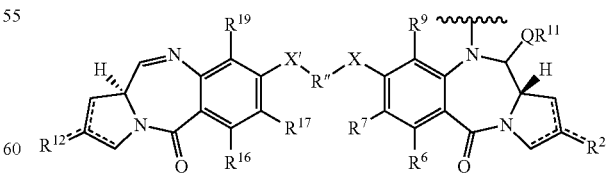

and salts and solvates thereof, wherein:
the wavy line indicates the covalent attachment site to the linker;
the dotted lines indicate the optional presence of a double bond between C1 and C2 or C2 and C3;

$R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo, wherein R$^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

Q is independently selected from 0, S and NH;

$R^{11}$ is either H, or R or, where Q is O, SO$_3$M, where M is a metal cation;

R and R' are each independently selected from optionally substituted C$_{1-8}$ alkyl, C$_{1-12}$ alkyl, C$_{3-8}$ heterocyclyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring;

$R^{12}, R^{16}, R^{19}$ and $R^{17}$ are as defined for $R^2, R^6, R^9$ and $R^7$ respectively;

R" is a C$_{3-12}$ alkylene group, which chain may be interrupted by one or more heteroatoms, e.g. O, S, N(H), NMe and/or aromatic rings, e.g. benzene or pyridine, which rings are optionally substituted; and X and X' are independently selected from O, S and N(H).

In some embodiments, R and R' are each independently selected from optionally substituted C$_{1-12}$ alkyl, C$_{3-20}$heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring. In some embodiments, $R^9$ and $R^{19}$ are H. In some embodiments, $R^6$ and $R^{16}$ are H.

In some embodiments, $R^7$ are $R^{17}$ are both OR$^{7A}$, where $R^{7A}$ is optionally substituted C$_{1-4}$ alkyl. In some embodiments, $R^{7A}$ is Me. In some embodiments, $R^{7A}$ is Ch$_2$Ph, where Ph is a phenyl group. In some embodiments, X is O. In some embodiments, $R^{11}$ is H. In some embodiments, there is a double bond between C2 and C3 in each monomer unit.

In some embodiments, $R^2$ and $R^{12}$ are independently selected from H and R. In some embodiments, $R^2$ and $R^{12}$ are independently R. In some embodiments, $R^2$ and $R^{12}$ are independently optionally substituted C$_{5-20}$ aryl or C$_{5-7}$aryl or C$_{8-10}$ aryl. In some embodiments, $R^2$ and $R^{12}$ are independently optionally substituted phenyl, thienyl, napthyl, pyridyl, quinolinyl, or isoquinolinyl. In some embodiments, $R^2$ and $R^{12}$ are independently selected from =O, =CH$_2$, =CH—R$^D$, and =C(R$^D$)$_2$. In some embodiments, $R^2$ and $R^{12}$ each =CH$_2$. In some embodiments, $R^2$ and $R^{12}$ are each H. In some embodiments, $R^2$ and $R^{12}$ are each =O. In some embodiments, $R^2$ and $R^{12}$ are each =CF$_2$. In some embodiments, $R^2$ and/or $R^{12}$ are independently =C(R$^D$)$_2$. In some embodiments, $R^2$ and/or $R^{12}$are independently =CH—R$^D$.

In some embodiments, when $R^2$ and/or $R^{12}$ is =CH—R$^D$, each group may independently have either configuration shown below:

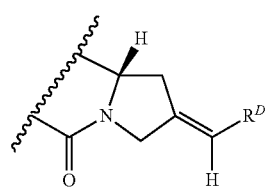

(I)

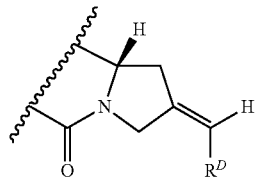

(II)

In some embodiments, a =CH—R$^D$ is in configuration (I). In some embodiments, R" is a C$_3$ alkylene group or a C$_8$ alkylene group.

The linkers of PBD dimer-val-cit-PAB-Ab and the PBD dimer-Phe-Lys-PAB-Ab are protease cleavable, while the linker of PBD dimer-maleimide-acetal is acid-labile.

PBD dimers and ADCs comprising PBD dimers may be prepared according to methods known in the art. See, e.g., WO 2009/016516; US 2009/304710; US 2010/047257; US 2009/036431; US 2011/0256157; WO 2011/130598.

5) Anthracyclines

In some embodiments, an ADC may comprise anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in *Anthracycline: Current Status And New Developments*, p. 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al., *Current Med. Chem.*, vol. 13, pp. 477-523, 2006; Jeffrey et al., *Bioorganic & Med. Chem. Letters*, vol. 16, pp. 358-362. 1996; Torgov et al., *Bioconj. Chem.*, vol. 16, pp. 717-721, 2005; Nagy et al., *Proc. Natl. Acad. Sci. USA*, vol. 97, pp. 829-834, 2000; Dubowchik et al., *Bioorg. & Med. Chem. Letters*, vol. 12, pp. 1529-1532, 2002; King et al., *J. Med. Chem.*, vol. 45, pp. 4336-4343, 2002; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al., *J. Clin. Oncology*, vol. 18, pp. 2282-2292, 2000; Ajani et al., *Cancer Jour.*, vol. 6, pp. 78-81, 2000; Tolcher et al., *J. Clin. Oncology*, vol. 17, pp. 478-484, 1999).

PNU-159682 is a potent metabolite (or derivative) of nemorubicin (Quintieri et al., *Clinical Cancer Research*, vol. 11, pp. 1608-1617, 2005). Nemorubicin is a semisynthetic analog of doxorubicin with a 2-methoxymorpholino group on the glycoside amino of doxorubicin and has been under clinical evaluation (Grandi et al. *Cancer Treat. Rev.* vol. 17, pp. 133-138, 1990; Ripamonti et al. *Brit. J. Cancer*, vol. 65, pp. 703-707, 1992), including phase II/III trials for hepatocellular carcinoma (Sun et al., *Proceedings of the American Society for Clinical Oncology*, vol. 22, Abs1448, 2003; Quintieri, *Proceedings of the American Association of Cancer Research*, vol. 44:1st Ed, Abs 4649, 2003; Pacciarini et al., *Jour. Clin. Oncology*, vol. 24, p. 14116, 2006).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

The linker of PNU-159682 maleimide acetal-Ab is acid-labile, while the linkers of PNU-159682-val-cit-PAB-Ab, PNU-159682-val-cit-PAB-spacer-Ab, and PNU-159682-val-cit-PAB-spacer($R^1R^2$)-Ab are protease cleavable.

6) Other Drug Moieties

Drug moieties also include geldanamycin (Mandler et al., *J. Nat. Cancer Inst.*, vol. 92, pp. 1573-1581, 2000; Mandler et al., *Bioorganic & Med. Chem. Letters*, vol. 10, pp. 1025-1028, 2000; Mandler et al., *Bioconjugate Chem.*, vol. 13, pp. 786-791, 2002); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

In certain embodiments, an immunoconjugate may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. In some embodiments, when an immunoconjugate is used for detection, it may comprise a radioactive atom for scintigraphic studies, for example $Tc^{99}$ or $I^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al., *Biochem. Biophys. Res. Commun.*, vol. 80, pp. 49-57, 1978) can be used to incorporate iodine-123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as *Serratia* protease, thermolysis, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature*, vol. 312, pp. 604-608, 1984.

c) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody use in the preparation of ADCs from conjugation reactions may be characterized by conventional means such as mass spectroscopy, ELISA assay, and HPLC. The quantitative distribution of ADCs in terms of p may also be determined. In some instances, separation, purification, and characterization of homogeneous ADCs where p is a certain value from ADCs with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADCs with a distribution of one or more drug moieties attached to an antibody. The average number of drugs per antibody may be calculated from the mixture by a dual ELISA antibody assay, which is specific for antibody and specific for the drug. Individual ADCs may be identified in the mixture by mass spectroscopy and separated by HPLC, e.g. hydrophobic interaction chromatography (see, e.g., McDonagh et al., *Prot. Engr. Design & Selection*, vol. 19, pp. 299-307, 2006; Hamblett et al., *Clin. Cancer Res.*, vol. 10, pp. 7063-7070, 2004). In certain embodiments, a homogeneous ADC with a single loading value may be isolated from the conjugation mixture by electrophoresis or chromatography.

d) Certain Methods of Preparing Immunoconjugates

An immunoconjugate that is an ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody or antibody fragment, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, *Bioconjugate Chem.*, vol. 3, pp. 138-146, 1992; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADCs are described herein in the section titled "Exemplary Linkers." Methods of using such cross-linker reagents to link two moieties, including a proteinaceous moiety and a chemical moiety, are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody or antibody fragment may be conjugated to a "receptor" (such as streptavidin) for utilization in tumor pre-targeting wherein the antibody/antibody fragment-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

C. Methods and Compositions for Diagnostics and Detection

In certain embodiments, any of the anti-Ror2 antibodies or antibody fragments provided herein may be used for detecting the presence of Ror2 in a biological sample. The term "detecting" as used herein encompasses quantitative or qualitative detection. In certain embodiments, a biological sample comprises a cell or tissue, such as breast, pancreas, esophagus, lung and/or brain cells or tissue.

A further aspect of the invention relates to an anti-Ror2 antibody or antibody fragment of the invention for diagnosing and/or monitoring a cancer or another disease in which Ror2 expression levels are increased or decreased from a normal physiological level at at least one location in the body.

In a preferred embodiment, antibodies or antibody fragments of the invention may be labelled with a detectable molecule or substance, such as a fluorescent molecule, a radioactive molecule or any other label known in the art as above described. For example, an antibody or antibody fragment of the invention may be labelled with a radioactive molecule. For example, suitable radioactive molecules include but are not limited to radioactive atoms used for scintigraphic studies such as $^{123}$I, $^{124}$I, $^{111}$In, $^{186}$Re, and $^{188}$Re. Antibodies or antibody fragments of the invention may also be labelled with a spin label for nuclear magnetic resonance (NMR) imaging, such as iodine-123, iodine-131, indium-Ill, fluorine-19, carbon-13, nitrogen-15, oxygen-17, gadolinium, manganese or iron. Following administration of the antibody, the distribution of the radiolabeled antibody within the patient is detected. Any suitable known method can be used. Some non-limiting examples include, computed tomography (CT), position emission tomography (PET), magnetic resonance imaging (MRI), fluorescence, chemiluminescence and sonography.

Antibodies or antibody fragments of the invention may be useful for diagnosing and staging of cancer and diseases associated with Ror2 overexpression. Cancers associated with Ror2 overexpression may include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma, sarcomas, hematological cancers (leukemias), astrocytomas, and various types of head and neck cancer or other Ror2 expressing or overexpressing hyperproliferative diseases.

Antibodies or antibody fragments of the invention may be useful for diagnosing diseases other than cancers for which Ror2 expression is increased or decreased. Both the (soluble or cellular Ror2 forms can be used for such diagnoses. Typically, such diagnostic methods involve use of a biological sample obtained from the patient. As used herein the term "biological sample" encompasses a variety of sample types obtained from a subject that can be used in a diagnostic or monitoring assay. Biological samples include but are not limited to blood and other liquid samples of biological origin, solid tissue samples such as a biopsy specimen or a tissue culture or cells derived therefrom, and the progeny thereof. For example, biological samples include cells obtained from a tissue sample collected from an individual suspected of having a cancer associated with Ror2 overexpression, and in preferred embodiments from glioma, gastric, lung, pancreatic, breast, prostate, renal, hepatic and endometrial. Biological samples encompass clinical samples, cells in culture, cell supernatants, cell lysates, serum, plasma, biological fluid, and tissue samples.

In a particular embodiment, the invention is a method of diagnosing a cancer associated with Ror2 overexpression in a subject by detecting Ror2 on cells from the subject using the antibody of the invention. In particular, said method may include steps of:

(a) contacting a biological sample of a subject with an antibody or antibody fragment according to the invention under conditions suitable for the antibody or antibody fragment to form complexes with cells in the biological sample that express Ror2; and (b) detecting and/or quantifying said complexes, whereby detection of said complexes is indicative of a cancer associated with Ror2 overexpression.

In order to monitor the progress of a cancer, the method according to the invention may be repeated at different times, in order to determine if antibody binding to the samples increases or decreases, wherefrom it can be determined if the cancer has progressed, regressed or stabilized.

In a particular embodiment, the invention is a method of diagnosing a disease associated with the expression or overexpression of Ror2 or a decrease or increase of the soluble form of Ror2. Examples of such diseases may include human immune disorders, thrombotic diseases (thrombosis and atherothrombosis), and cardiovascular diseases In one embodiment, an anti-Ror2 antibody or antibody fragment for use in a method of diagnosis or detection is provided. In a further aspect, a method of detecting the presence of Ror2 in a biological sample is provided. In a further aspect, a method of quantifying the amount of Ror2 in a biological sample is provided. In certain embodiments, the method comprises contacting the biological sample with an anti-Ror2 antibody or antibody fragment as described herein under conditions permissive for binding of the anti-Ror2 antibody or antibody fragment to Ror2, and detecting whether a complex is formed between the anti-Ror2 antibody or antibody fragment and Ror2. Such a method may be carried out in vitro or in vivo. In one embodiment, an anti-Ror2 antibody or antibody fragment is used to select subjects eligible for therapy. In some embodiments, the therapy will include administration of an anti-Ror2 antibody or antibody fragment to the subject.

In certain embodiments, labeled anti-Ror2antibodies or antibody fragments are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

D. Pharmaceutical Formulations

The anti-Ror2 antibodies or antibody fragments have cell killing activity. This cell killing activity extends to multiple different types of cell lines. Further, these antibodies or antibody fragments, once conjugated to a cytotoxic agent, can reduce tumor size and may exhibit reduced toxicity. See Example 2 of this application. Thus, the anti-Ror2 antibodies, fragments or immunoconjugates thereof may be useful for treating proliferative diseases associated with Ror2 expression. The antibodies, fragments or immunoconjugates may be used alone or in combination with any suitable agent or other conventional treatments.

The anti-Ror2 antibody or antibody fragment may be used to treat diseases associated with Ror2 expression, overexpression or activation. There are no particular limitations on the types of cancer or tissue that can be treated other than the requirement for Ror2 expression. Examples include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma, sarcomas, hematological cancers (leukemias), astrocytomas, and various types of head and neck cancer. More preferable cancers are glioma, gastric, lung, pancreatic, breast, prostate, renal, hepatic and endometrial cancer.

Anti-Ror2 antibodies or antibody fragments are potential activators of the innate immune response and thus may be used in the treatment of human immune disorders, such as sepsis. The anti-Ror2 antibody or antibody fragment of the invention may also be used as adjuvants for immunization such as for vaccines and as anti-infection agents against, for example, bacteria, viruses and parasites.

Anti-Ror2 antibody or antibody fragment may be used to protect against, prevent or treat thrombotic diseases such as venous and arterial thrombosis and atherothrombosis. Anti-Ror2 antibody or antibody fragment may also be used to protect against, prevent or treat cardiovascular diseases as well as to prevent or inhibit the entry of viruses such as Lassa and Ebola viruses and to treat viral infections.

In each of the embodiments of the treatment methods described herein, the anti-Ror2 antibody, antibody fragment or anti-Ror2 antibody or antibody fragment immunoconjugate may be delivered in a manner consistent with conventional methodologies associated with management of the disease or disorder for which treatment is sought. In accordance with the disclosure herein, an effective amount of the antibody, antibody fragment or immunoconjugate is administered to a subject in need of such treatment for a time and under conditions sufficient to prevent or treat the disease or disorder. Thus, an aspect of the invention relates to a method for treating a disease associated with the expression of Ror2 comprising administering to a subject in need thereof with a therapeutically effective amount of an antibody, antibody fragment or immunoconjugate of the invention.

For administration, the anti-Ror2 antibody, antibody fragment or immunoconjugate may be formulated as a pharmaceutical composition. The pharmaceutical composition including anti-Ror2 antibody, antibody fragment or immunoconjugate can be formulated according to known methods for preparing pharmaceutical compositions. In such methods, the therapeutic molecule is typically combined with a mixture, solution or composition containing a pharmaceutically acceptable carrier.

A pharmaceutically acceptable carrier is a material that can be tolerated by a recipient patient. Sterile phosphate-buffered saline is one example of a pharmaceutically acceptable carrier. Other suitable pharmaceutically acceptable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc. These considerations can be taken into account by a skilled person to formulate suitable pharmaceutical compositions. The pharmaceutical compositions of the invention can be formulated for topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition of, for example, sterilized water or physiological saline, permit the constitution of injectable solutions.

In some embodiments, tonicity agents, sometimes known as "stabilizers" are present to adjust or maintain the tonicity of a liquid in a composition. When used with large, charged biomolecules such as proteins and antibodies, they are often termed "stabilizers" because they can interact with the charged groups of the amino acid side chains, thereby lessening the potential for inter- and intra-molecular interactions. Tonicity agents can be present in any amount of from 0.1% to 25% by weight, preferably 1 to 5% of the pharmaceutical composition. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients may include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, u-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") may be employed to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants may be present in a concentration range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride The doses used for the administration can be adapted as a function of various parameters, and in particular as a function of the mode of administration used, of the relevant pathology, or alternatively of the desired duration of treatment. To prepare pharmaceutical compositions, an effective amount of the antibody or antibody fragment may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in a water suitably mixed with a surfactant. Dispersions can also be prepared in glycerol, liquid polyethylene glycols, and mixtures thereof and in oils. Under ordinary conditions of storage and use, these preparations contain a preservative to prevent the growth of microorganisms.

The anti-Ror2 antibody or antibody fragment can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with one or more of the other ingredients enumerated above, as may be required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of dimethyl sulfoxide (DMSO) as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies or antibody fragments may be formulated within a therapeutic mixture to deliver about 0.0001 to 10.0 milligrams, or about 0.001 to 5 milligrams, or about 0.001 to 1 milligrams, or about 0.001 to 0.1 milligrams, or about 0.1 to 1.0 or even about 10 milligrams per dose. Multiple doses can also be administered at selected time intervals.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies or antibody fragments into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to degrade in vivo. Biodegradable polyalkyl-cyanoacrylate nanoparticles that meet these requirements are contemplated for use in the present invention, and such particles may be easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations Pharmaceutical formulations containing an anti-Ror2 antibody or antibody fragment as described herein are prepared by mixing such antibody or antibody fragment having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredient as necessary for the particular indication being treated. Preferably, ingredients with complementary activities that do not adversely affect each other may be combined into a single formulation. For example, it may be desirable to provide an EGFR antagonist (such as erlotinib), an anti-angiogenic agent (such as a VEGF antagonist which may be an anti-VEGF antibody) or a chemotherapeutic agent (such as a taxoid or a platinum agent) in addition to the anti-Ror2 antibody, antibody fragment or immunoconjugate of the present invention. Such active ingredients are suitably present in combination in amounts that are effective for the purpose intended.

Active ingredients may be encapsulated in microcapsules prepared, for example, by coacervation techniques or by interfacial polymerization. For example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions may be employed. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody or antibody fragment, which matrices may be in the form of shaped articles, e.g. films, or microcapsules.

The formulations to be used for in vivo administration are generally sterile. Sterility may be readily accomplished, e.g., by filtration through sterile filtration membranes.

E. Therapeutic Methods and Compositions

Any of the anti-Ror2 antibodies or antibody fragments provided herein may be used in therapeutic methods. In one aspect, an anti-Ror2 antibody or antibody fragment for use as a medicament is provided. In further aspects, an anti-Ror2 antibody or antibody fragment for use in treating cancer (e.g., breast cancer, non-small cell lung cancer, pancreatic cancer, brain cancer, cancer of pancreas, brain, kidney, ovary, stomach, leukemia, uterine endometrium, colon, prostate, thyroid, liver, osteosarcoma, and/or melanoma) is provided. In certain embodiments, an anti-Ror2 antibody or antibody fragment for use in a method of treatment is provided. In certain embodiments, the invention provides an anti-Ror2 antibody or antibody fragment for use in a method of treating an individual having cancer comprising administering to the individual an effective amount of the anti-Ror2 antibody or antibody fragment. In certain embodiments, the invention provides an anti-Ror2 antibody or antibody fragment for use in a method of treating an individual having an immune disorder (e.g., an autoimmune disorder), a cardiovascular disorder (e.g., atherosclerosis, hypertension, thrombosis), an infectious disease (e.g., Ebola virus, Marburg virus) or diabetes, comprising administering to the individual an effective amount of the anti-Ror2 antibody or antibody fragment. In one such embodiment, the method further comprises administering to the individual an effective amount of at least one additional therapeutic agent, e.g., as described below. In further embodiments, the invention provides an anti-Ror2 antibody or antibody fragment for use in inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function.

In certain embodiments, the invention provides an anti-Ror2 antibody or antibody fragment for use in a method of inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function in an individual comprising administering to the individual an effective of the anti-Ror2 antibody or antibody fragment to inhibit angiogenesis, inhibit cell proliferation, inhibit immune function, inhibit inflammatory cytokine secretion (e.g., from tumor-associated macrophages), inhibit tumor vasculature development (e.g., intratumoral vasculature or tumor-associated vasculature), and/or inhibit tumor stromal function. An "individual" according to any of the above embodiments is preferably a human.

In a further aspect, the invention provides for the use of an anti-Ror2 antibody or antibody fragment in the manufacture or preparation of a medicament. In one embodiment, the medicament is for treatment of cancer (in some embodiments, breast cancer, non-small cell lung cancer, pancreatic cancer, brain cancer, cancer of the pancreas, brain, kidney, ovary, stomach, leukemia, uterine endometrium, colon, prostate, thyroid, liver, osteosarcoma, and/or melanoma). In a further embodiment, the medicament is for use in a method of treating cancer comprising administering to an individual having cancer an effective amount of the medicament. In a further embodiment, the medicament is for use in a method of treating an immune disorder (e.g., an autoimmune disorder), a cardiovascular disorder (e.g., atherosclerosis, hypertension, thrombosis), an infectious disease (e.g., Ebola virus, Marburg virus) or diabetes, comprising administering to the individual an effective amount of the anti-Ror2 antibody or antibody fragment. In one such embodiment, the method further comprises administering to the individual an effective amount of at least one additional therapeutic agent, e.g., as described below. In a further embodiment, the medicament is for inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function. In a further embodiment, the medicament is for use in a method of inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function in an individual comprising administering to the individual an amount effective of the medicament to inhibit angiogenesis, inhibit cell proliferation, promote immune function, induce inflammatory cytokine section (e.g., from tumor-associated macrophages), inhibit tumor vasculature development (e.g., intratumoral vasculature or tumor-associated vasculature), and/or inhibit tumor stromal function. An "individual" according to any of the above embodiments may be a human.

In a further aspect, the invention provides a method for treating a cancer. In one embodiment, the method comprises administering to an individual having such cancer an effective amount of an anti-Ror2 antibody or antibody fragment. In one such embodiment, the method further comprises administering to the individual an effective amount of at least one additional therapeutic agent, as described below. An "individual" according to any of the above embodiments may be a human.

In a further aspect, the invention provides a method for treating an immune disorder (e.g., an autoimmune disorder), a cardiovascular disorder (e.g., atherosclerosis, hypertension, thrombosis), an infectious disease (e.g., Ebola virus, Marburg virus) or diabetes. In one such embodiment, the method further comprises administering to the individual an effective amount of at least one additional therapeutic agent, as described below. An "individual" according to any of the above embodiments may be a human.

In a further aspect, the invention provides a method for inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function in an individual. In one embodiment, the method comprises administering to the individual an effective amount of an anti-Ror2 antibody or antibody fragment to inhibit angiogenesis, inhibit cell proliferation, promote immune function, induce inflammatory cytokine section (e.g., from tumor-associated macrophages), inhibit tumor vasculature development (e.g., intratumoral vasculature or tumor-associated vasculature), and/or inhibit tumor stromal function. In one embodiment, an "individual" is a human.

In a further aspect, the invention provides pharmaceutical formulations comprising any of the anti-Ror2 antibodies or antibody fragments provided herein, e.g., for use in any of the above therapeutic methods. In one embodiment, a pharmaceutical formulation comprises any of the anti-Ror2 antibodies or antibody fragments provided herein and a pharmaceutically acceptable carrier. In another embodiment, a pharmaceutical formulation comprises any of the anti-Ror2 antibodies or antibody fragments provided herein and at least one additional therapeutic agent, e.g., as described below.

In each and every treatment described above, the antibodies or antibody fragments of the invention can be used alone, as immunoconjugates or in combination with other agents in a therapy. For instance, an antibody of the invention may be co-administered with at least one additional therapeutic agent. In certain embodiments, an additional therapeutic agent is an anti-angiogenic agent. In certain embodiments, an additional therapeutic agent is a VEGF antagonist (in some embodiments, an anti-VEGF antibody, for example bevacizumab). In certain embodiments, an additional therapeutic agent is an EGFR antagonist (in some embodiment, erlotinib). In certain embodiments, an additional therapeutic agent is a chemotherapeutic agent and/or a cytostatic agent. In certain embodiments, an additional therapeutic agent is a taxoid (e.g., paclitaxel) and/or a platinum agent (e.g., carboplatinum). In certain embodiments the additional therapeutic agent is an agents that enhances the patient's immunity or immune system.

Such combination therapies noted above encompass combined administration (where two or more therapeutic agents are included in the same or separate formulations), and separate administration, in which case, administration of the antibody or antibody fragment can occur prior to, simultaneously, and/or following, administration of the additional therapeutic agent and/or adjuvant. Antibodies or antibody fragments can also be used in combination with radiation therapy.

Antibodies or antibody fragments may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or antibody fragment need not be, but is optionally formulated with one or more agents currently used to prevent or treat the disorder in question. The effective amount of such other agents depends on the amount of antibody or antibody fragment present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or antibody fragment (when used alone or in combination with one or more other additional therapeutic agents) will depend on the type of disease to be treated, the type of antibody or antibody fragment, the severity and course of the disease, whether the antibody or antibody fragment is administered for preventive or therapeutic purposes, previous therapy, the patient's clinical history and response to the antibody or antibody fragment, and the discretion of the attending physician. The antibody or antibody fragment is suitably administered to the patient at one time or over a series of treatments. Depending on the type and severity of the disease, about 1 µg/kg to 40 mg/kg of antibody or antibody fragment can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g. every week or every three weeks (e.g. such that the patient receives from about two to about twenty, or e.g. about six doses of the antibody or antibody fragment). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an antibody fragment or an immunoconjugate of the invention in place of or in addition to an anti-Ror2 antibody.

Enhancing the host's immune function to combat tumors is the subject of increasing interest. Conventional methods include (i) APC enhancement, such as (a) injection into the tumor of DNA encoding foreign MHC alloantigens, or (b) transfecting biopsied tumor cells with genes that increase the probability of immune antigen recognition (e.g., immune stimulatory cytokines, GM-CSF, co-stimulatory molecules B7.1, B7.2) of the tumor, (iii) adoptive cellular immunotherapy, or treatment with activated tumor-specific T-cells. Adoptive cellular immunotherapy includes isolating tumor-infiltrating host T-lymphocytes, expanding the population in vitro, such as through stimulation by IL-2 or tumor or both. Additionally, isolated T-cells that are dysfunctional may be also be activated by in vitro application of the anti-PD-L1 antibodies of the invention. T-cells that are so-activated may then be readministered to the host. One or more of these methods may be used in combination with administration of the antibody, antibody fragment or immunoconjugate of the present invention.

Traditional therapies for cancer include the following: (i) radiation therapy (e.g., radiotherapy, X-ray therapy, irradiation) or the use of ionizing radiation to kill cancer cells and shrink tumors. Radiation therapy can be administered either externally via external beam radiotherapy (EBRT) or internally via brachytherapy; (ii) chemotherapy, or the application of cytotoxic drug which generally affect rapidly dividing cells; (iii) targeted therapies, or agents which specifically affect the deregulated proteins of cancer cells (e.g., tyrosine kinase inhibitors imatinib, gefitinib; monoclonal antibodies, photodynamic therapy); (iv) immunotherapy, or enhancement of the host's immune response (e.g., vaccine); (v) hormonal therapy, or blockade of hormone (e.g., when tumor is hormone sensitive), (vi) angiogenesis inhibitor, or blockade of blood vessel formation and growth, and (vii) palliative care, or treatment directed to improving the quality of care to reduce pain, nausea, vomiting, diarrhea and hemorrhage. Pain medication such as morphine and oxycodone, anti-emetics such as ondansetron and aprepitant, can permit more aggressive treatment regimens.

In the treatment of cancer, any of the previously described conventional treatments for the treatment of cancer immunity may be conducted, prior, subsequent or simultaneous with the administration of the anti-Ror2 antibodies or antibody fragments. Additionally, the anti-Ror2 antibodies or antibody fragments may be administered prior, subsequent or simultaneous with conventional cancer treatments, such as the administration of tumor-binding antibodies (e.g., monoclonal antibodies, toxin-conjugated monoclonal antibodies) and/or the administration of chemotherapeutic agents.

F. Articles of Manufacture and Kits

In another aspect of the invention, an article of manufacture containing an anti-Ror2 antibody or antibody fragment and other materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody or antibody fragment of the invention. The label or package insert indicates that the composition is used for treating the condition of choice. Moreover, the article of manufacture may comprise (a) a first container with a composition contained therein, wherein the composition comprises an antibody or antibody fragment; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-Ror2 antibody or antibody fragment.

Finally, the invention also provides kits comprising at least one antibody or antibody fragment of the invention. Kits containing polypeptide, antibodies or antibody fragments, or antibody drug conjugate of the invention find use in detecting Ror2 expression (increase or decrease), or in therapeutic or diagnostic assays. Kits of the invention can contain an antibody coupled to a solid support, e.g., a tissue culture plate or beads (e.g., sepharose beads). Kits can be provided which contain antibodies for detection and quantification of Ror2 in vitro, e.g. in an ELISA or a Western blot. Such antibody useful for detection may be provided with a label such as a fluorescent or radiolabel.

The kits further contain instructions on the use thereof. In some embodiments, the instructions comprise instructions required by the U.S. Food and Drug Administration for in vitro diagnostic kits. In some embodiments, the kits further comprise instructions for diagnosing the presence or absence of cerebrospinal fluid in a sample based on the presence or absence of Ror2 in said sample. In some embodiments, the kits comprise one or more antibodies or antibody fragments. In other embodiments, the kits further comprise one or more enzymes, enzyme inhibitors or enzyme activators. In still other embodiments, the kits further comprise one or more chromatographic compounds. In yet other embodiments, the kits further comprise one or more compounds used to prepare the sample for spectroscopic assay. In further embodiments, the kits further comprise comparative reference material to interpret the presence or absence of Ror2 according to intensity, color spectrum, or other physical attribute of an indicator.

The following examples are illustrative, but not limiting, of the soft gelatin capsules of the present disclosure. Other suitable modifications and adaptations of the variety of conditions and parameters normally encountered in the field, and which are obvious to those skilled in the art, are within the scope of the disclosure.

EXAMPLES

Example 1: Conditionally Active Biological (CAB) Antibodies Against Ror2

Antibodies against human Ror2 were produced in this Example. A humanized antibody against Ror2 was used as the wild-type antibody to generate the CAB antibodies against Ror2. The DNAs encoding the wild-type antibody (heavy chain and light chain variable regions) were evolved to generate mutant antibody heavy chain and light chain variable region libraries. The mutant heavy chain and light chain variable regions in the libraries were screened for selective binding affinity to human Ror2 at pH 6.0 over pH 7.4 by ELISA (FIGS. 2A-2B and 3A-3B). Simultaneously, the expression level of the mutant antibodies was also optimized for the purpose of providing higher yields in a subsequent manufacturing process. The screening was done in serum using a FLAG tag because there were human antibodies in the serum which might cause false positives for the screening. The generated conditionally active antibodies were found to have a higher binding affinity to Ror2 at pH 6.0 than their binding affinity to the Ror2 at pH 7.4 (Tables 1 and 2).

Figure 4:
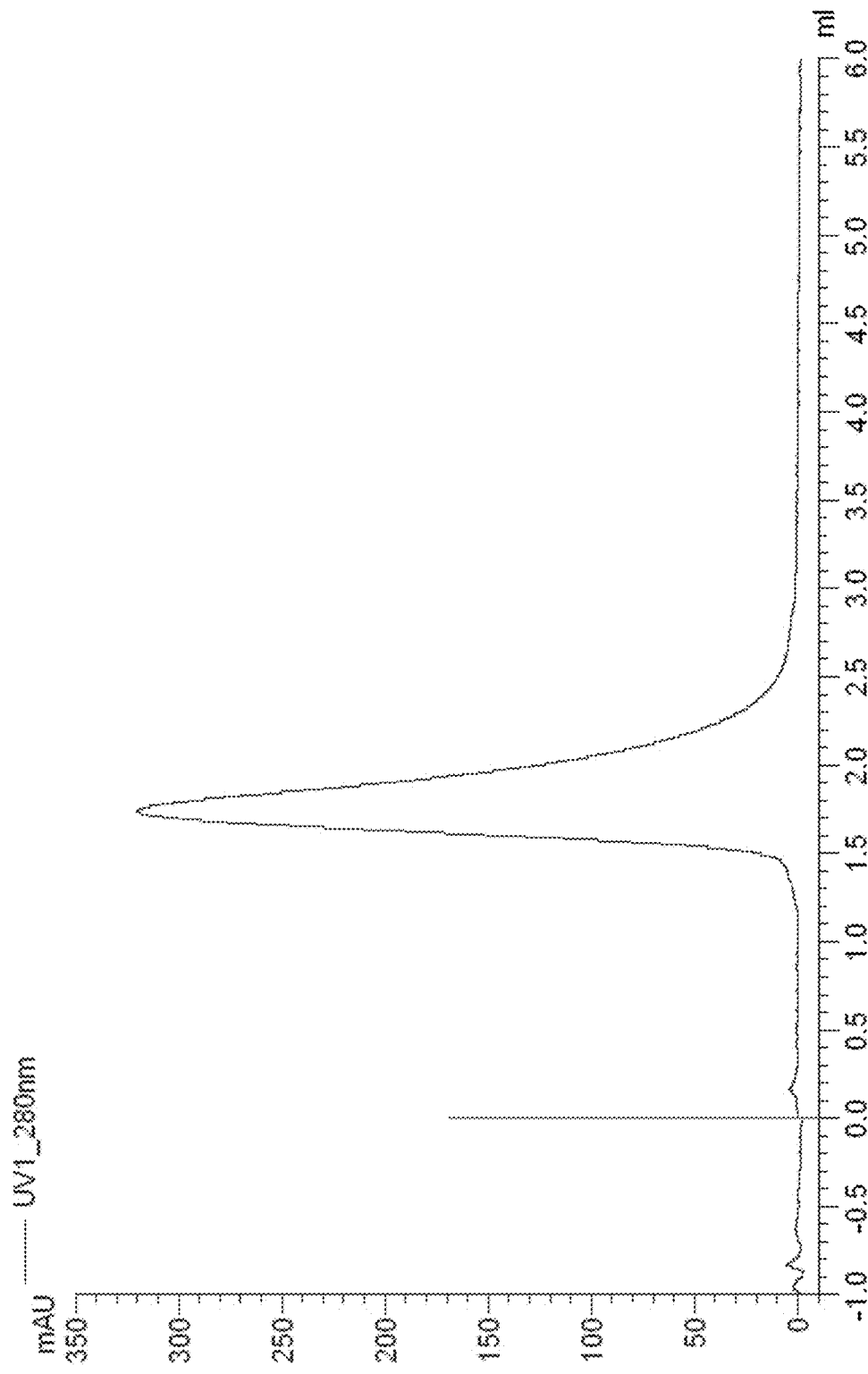
FIG. 4 shows a size exclusion chromatograph indicating that the anti-Ror2 antibodies of the invention do not aggregate, as described in Example 1.
Figure 5:
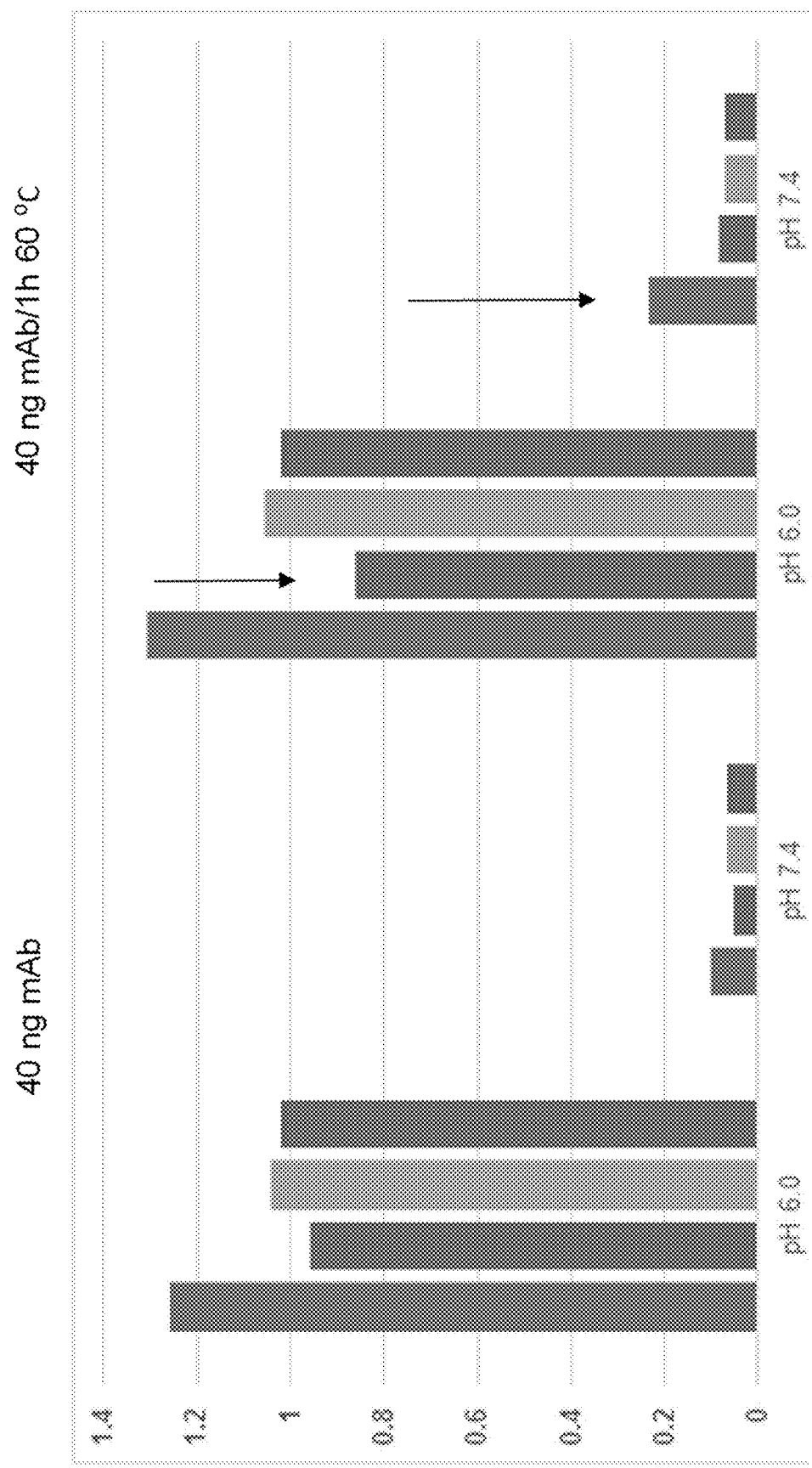
FIG. 5 shows pH-dependent binding profiles of anti-Ror2 antibodies of the present invention for binding to Ror2, as described in Example 1.

The CAB antibodies did not show aggregation in a buffer as demonstrated in FIG. 4. A CAB antibody was analyzed by size exclusion chromatography. As shown in FIG. 4, only one peak was detected, demonstrating little or no aggregation of the antibody. FIG. 5 shows that some of the selected mutant antibodies (scFv) demonstrated a higher binding affinity to Ror2 at pH 6.0 than the binding affinity to Ror2 at pH 7.4. In addition, FIG. 5 also shows that raising the temperature from room temperature to 60° C. did not significantly alter the selectivity of the antibodies.

The conditionally active antibodies all exhibited high expression levels as shown in Table 4 below, with the column "Clone" indicating the antibodies and the expression level being shown in the second column in mg/ml.

The clones of these antibodies were sent to a service provider with a requested expression level representing an expected expression level ("amount ordered"). However, the actual expression levels of several of these antibodies ("amount delivered") were very high and exceeded the expected expression levels. At least three clones had expression levels that exceeded the expected expression level (BAP048.7.067-HC-FLAG, BAP048.7-C02D09-FLAG, and BAP048.7-A03F01-FLAG).

TABLE 4

| Antibodies with high expression levels | | | |
|---|---|---|---|
| Clone | [mg/mL] | estimated yield | actual yield |
| BAP048.1-06-07 | 4.9 | 100 | 137 |
| BAP048.7-06-07 | 3.7 | 100 | 94 |
| BAP048.7-C02D09 | 3.8 | 30 | 57 |
| BAP048.7-A03F01 | 4.4 | 30 | 65 |
| BAP048.7-A03C05 | 4.2 | 30 | 36 |

The conditionally active antibodies were also assayed using surface plasmon resonance (SPR) to measure their on and off rates for binding to Ror2. The SPR assay can be used to measure on and off rates for protein binding. The in vivo on and off rate (in animals and humans) of the conditionally active antibodies is an important feature.

Figure 6A:
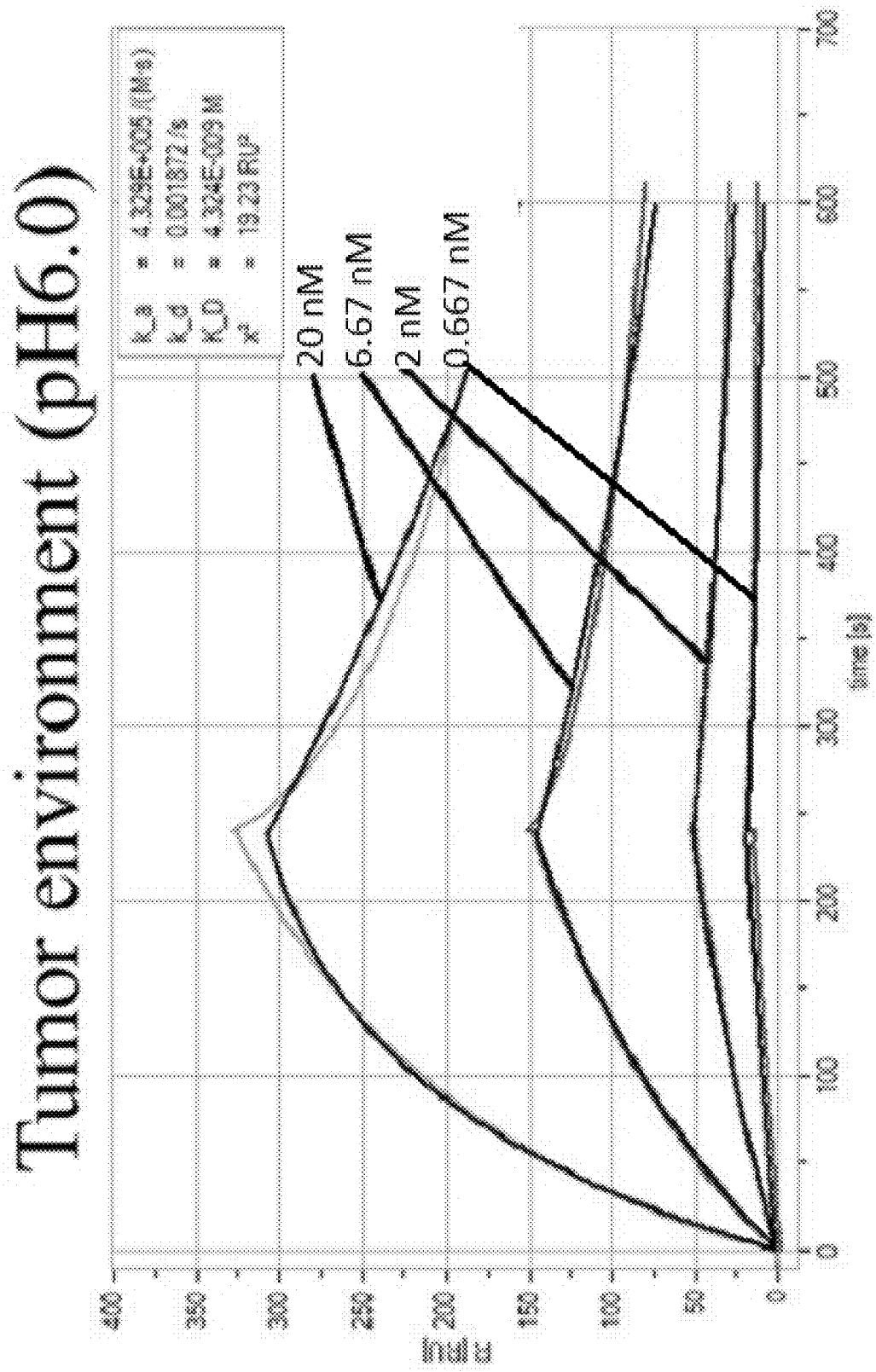
FIGS. 6A-6B show on and off rates of conditionally active antibodies of the invention as measured by surface plasmon resonance (SPR) assay, as described in Example 1.
Figure 6B:
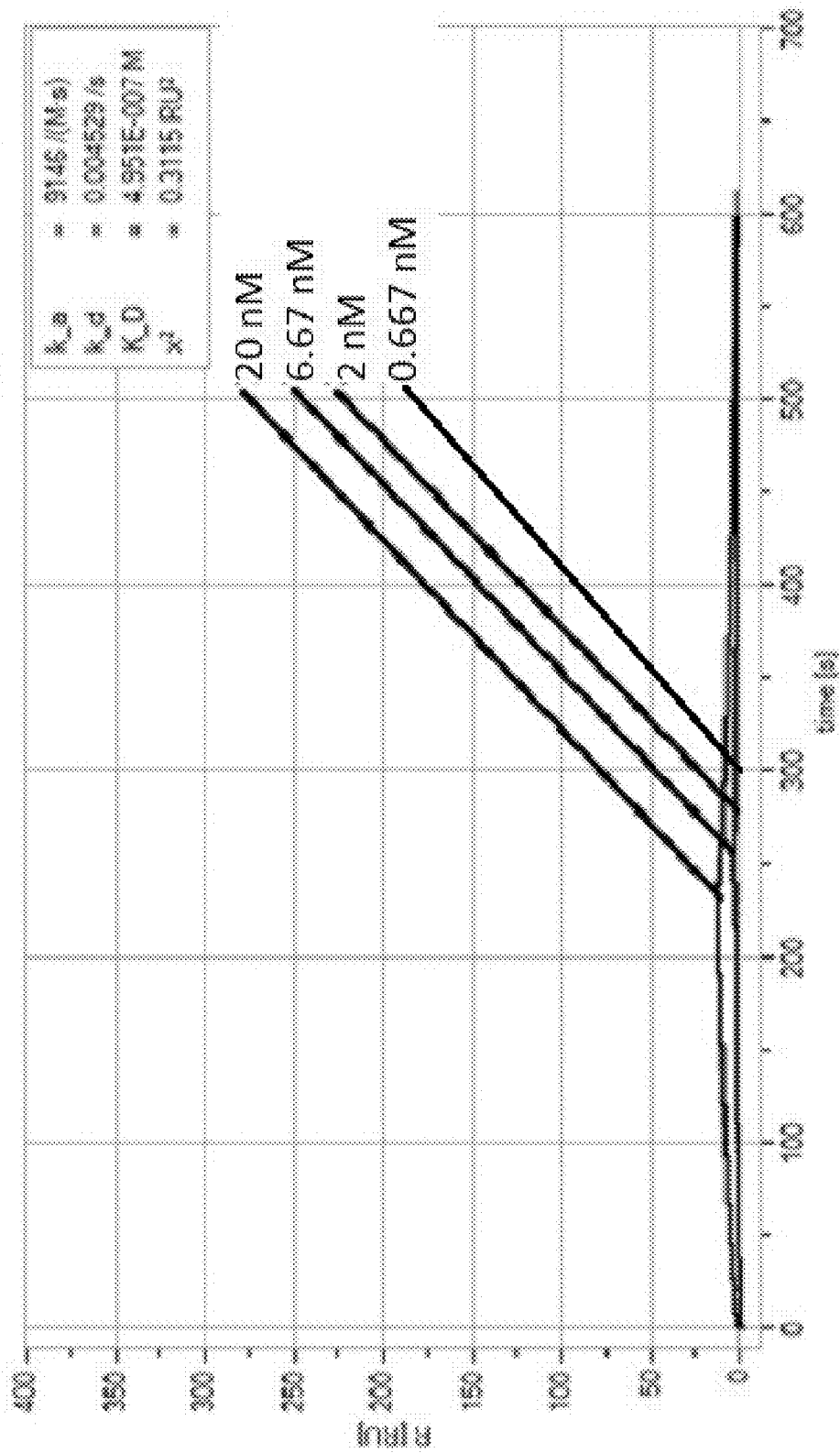

It was observed that the conditionally active antibodies have a good binding activity at pH 6.0 and little or no binding activity at pH 7.4 (FIGS. 6A-6B). The SPR assay showed that these same conditionally active antibodies were highly selective at pH 6.0 as compared to pH 7.4 (FIGS. 6A-6B).

Example 2: Anti-Ror2 Antibodies Conjugated to a Model Toxin

The anti-Ror2 antibody of the present invention was conjugated to a model toxin (e.g., paclitaxel) to produce a conditionally active antibody-drug conjugate (Ror2-CAB-ADC).

Figure 7A:
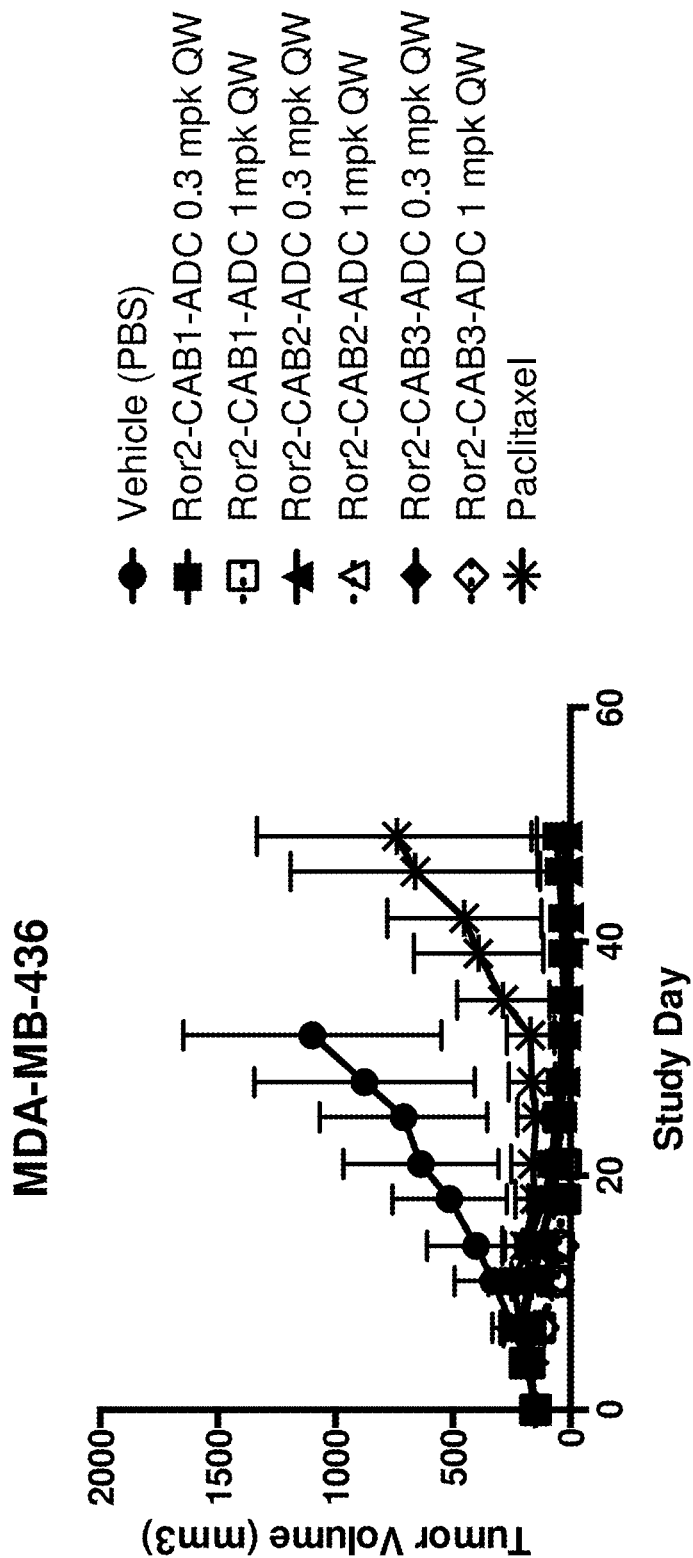
FIGS. 7A, 7B, and 7C show effects on tumor volume of treatment of xenografted mice with a paclitaxel-conjugated anti-Ror2 antibody of the present invention, as described in Example 2.
Figure 7B:
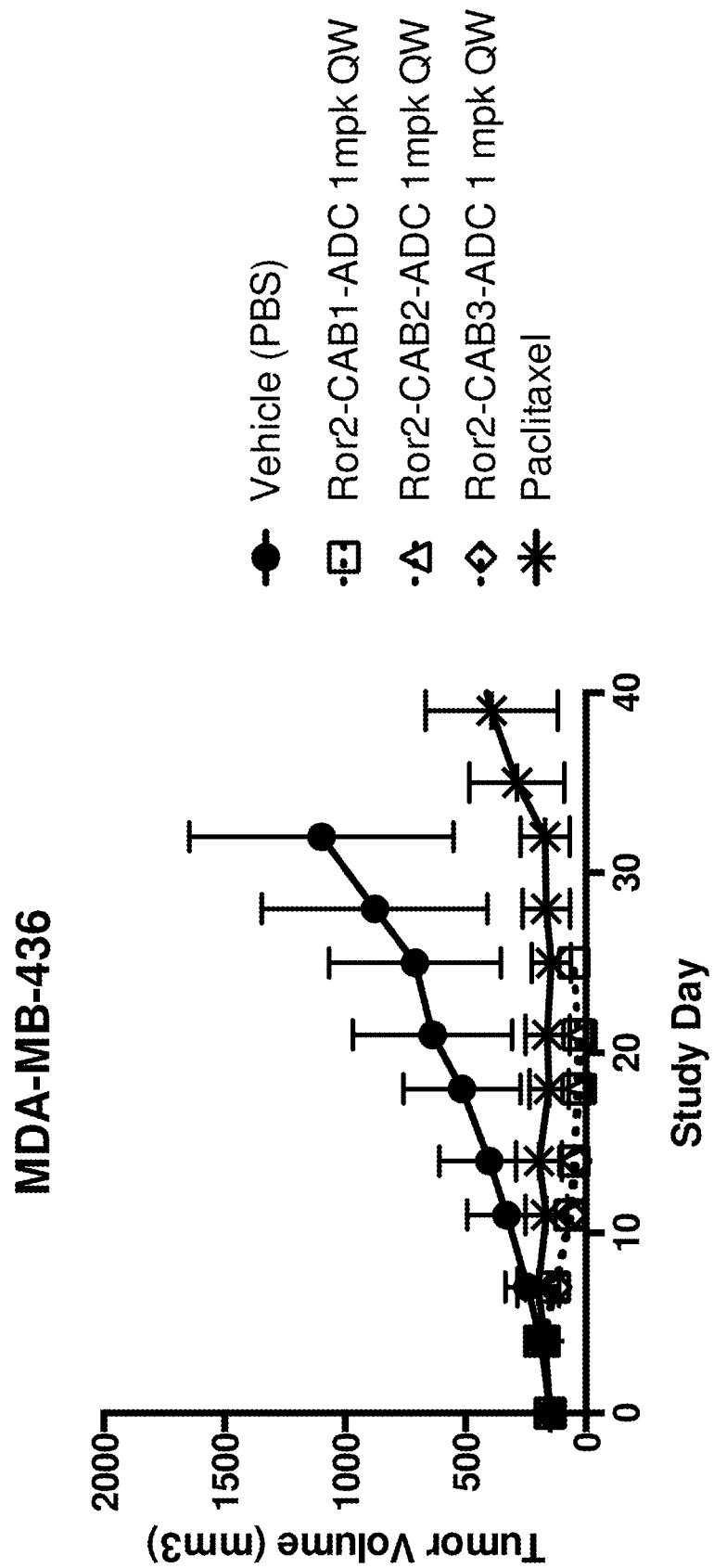
Figure 7C:
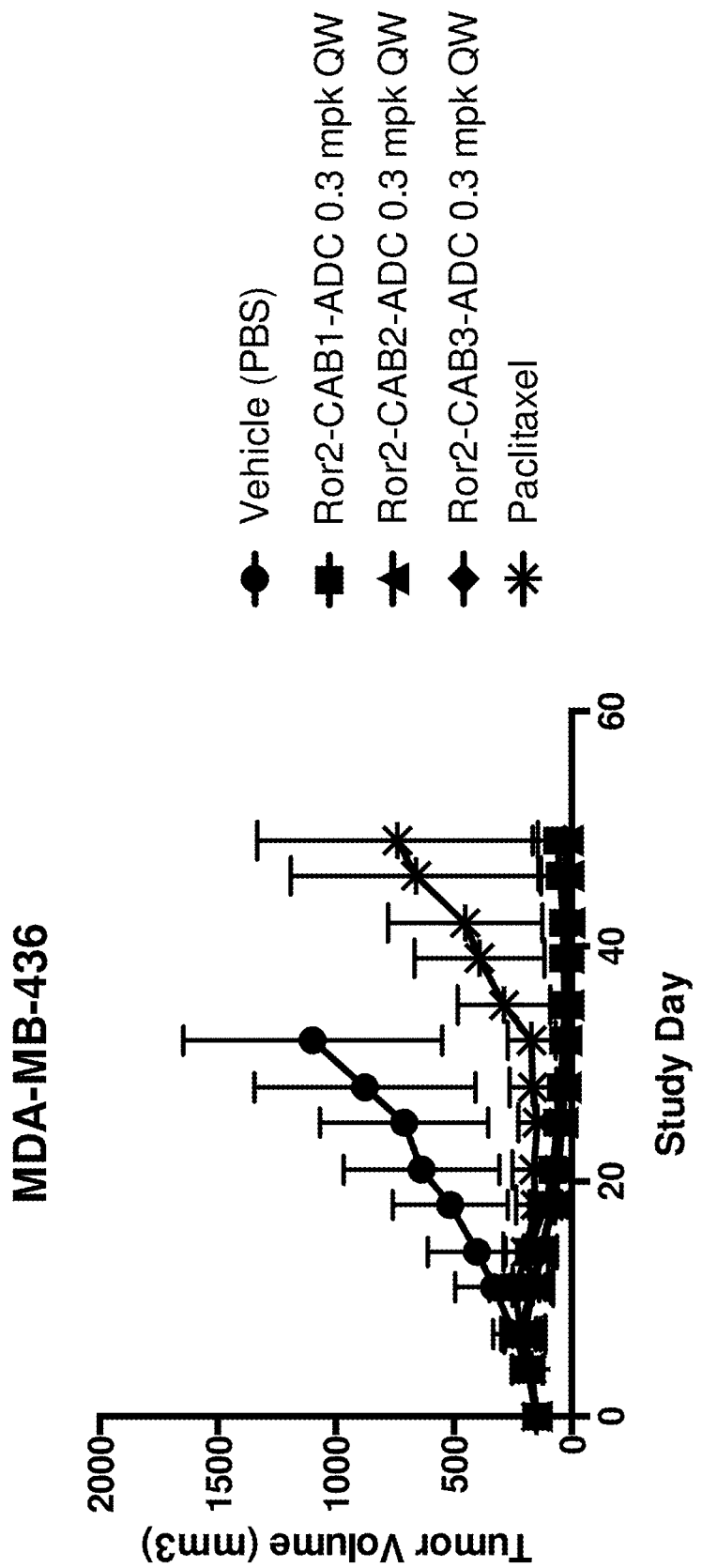

Tumors were induced in mice by injection of MDA-MB-436 tumor cells to produce xenografted mice. The Ror2-CAB-ADC was then injected into the xenografted mice at a dose of 0.3 or 1 mg/kg once a week for 2 weeks. The controls used in this study included PBS buffer as vehicle and the toxin alone (paclitaxel). The study showed that the Ror2-CAB-ADC provided a significantly greater reduction in the size of the tumor, in comparison with the controls (FIGS. 7A-7C). The results for the 0.3 mg/kg dosage group are presented in FIG. 7B and the results for the 1 mg/kg dosage group are presented in FIG. 7C. This study showed that the anti-Ror2 antibody conjugated with toxin is effective in reducing tumor size.

Example 3. pH Dependent Binding Affinity of Conditionally Active Antibody BAP048

Figure 8:
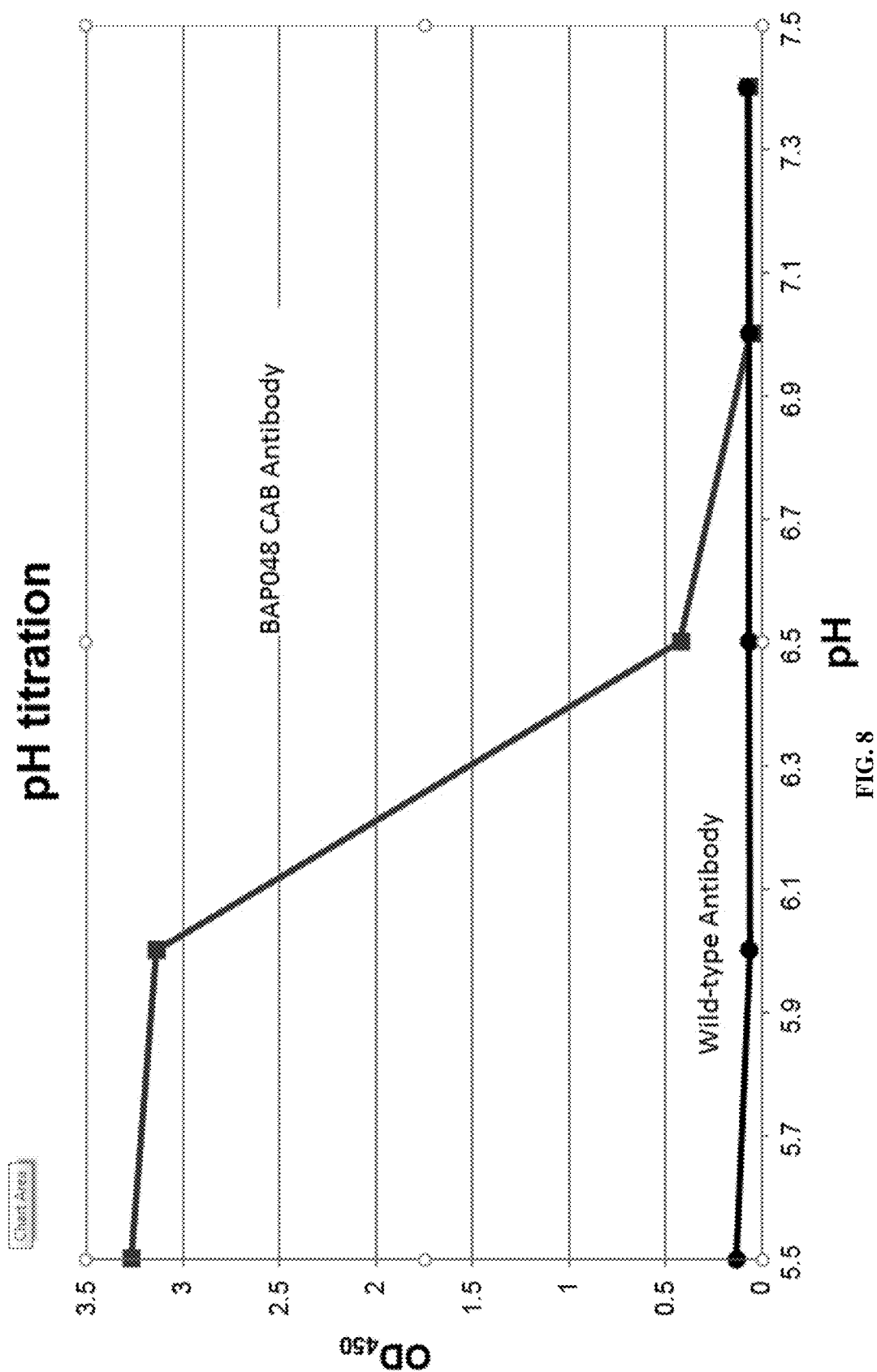
FIG. 8 shows the pH dependent binding affinity of an exemplary conditionally active antibody BAP048 measured by pH titration.

The binding affinity of one of the conditionally active antibodies identified by the present invention, BAP048 (or BAP048.7 as shown in some of the figures), was tested by pH titration. The wild-type antibody was used as control. As shown in FIG. 8, the conditionally active antibody BAP048 is more active at pH lower than pH 6.5, but less active at pH 7.0. The wild-type antibody does not show pH dependency for its binding affinity.

Example 4. Cross-Species Binding Affinity of Conditionally Active Antibody BAP048

Figure 9:
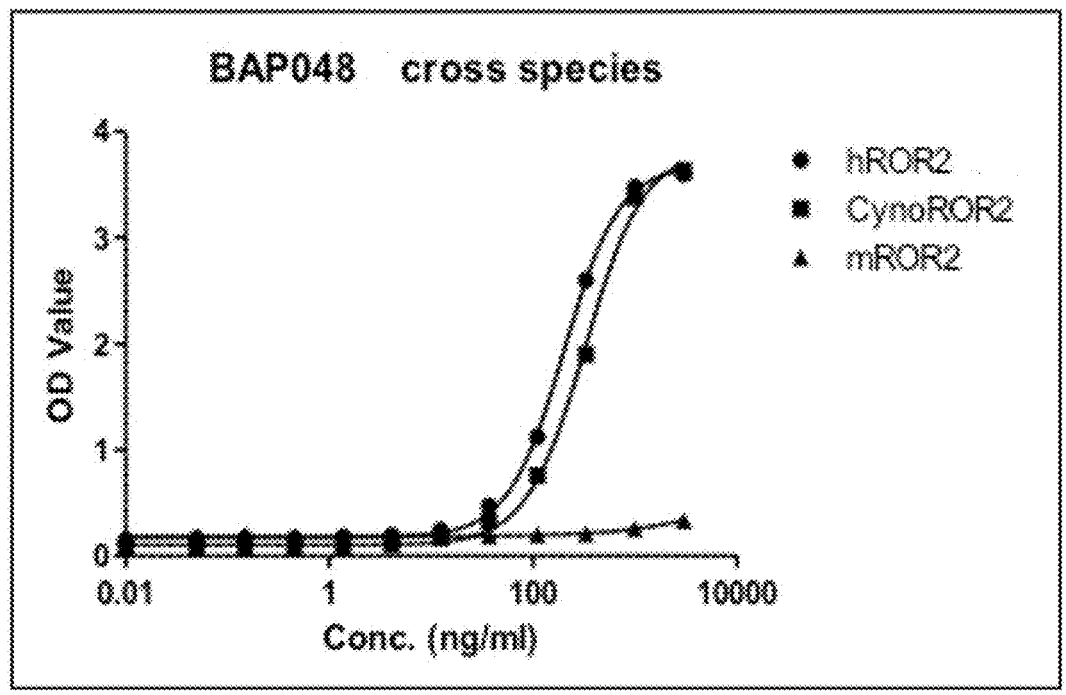
FIG. 9 shows the binding affinity of the conditionally active antibody BAP048 to Ror2 proteins of human, cynomolgus, and mouse.

The conditionally active antibody BAP048 was selected for conditional binding affinity of the human Ror2. This conditionally active antibody was tested for its binding affinity to three targets: human Ror2 (hROR2), cynomolgus Ror2 (cynoROR2), and mouse Ror2 (mROR2) using ELISA (FIG. 9). The conditionally active antibody BAP048 shown almost identical binding affinity to the human and cynomolgus Ror2, but significantly lower binding affinity to mouse Ror2. The EC50 of the conditionally active antibody BAP048 for the three targets were calculated to be 201.4 ng/ml for human Ror2, 327.1 ng/ml for ocynomolgus Ror2, and 7653 ng/ml for the mouse Ror2.

Example 5. Cell Killing by Conditionally Active Antibody BAP048-MMAE Conjugates

The conditionally active antibody BAP048 was conjugated to chemotherapy drug Monomethyl auristatin E (MMAE) to produce an antibody drug conjugate (ADC). The ADC was tested on HEK293 cells that express human Ror2 on the cell surface. Negative control used for this test was an affinity matching antibody but not specific for human Ror2. The negative control was also conjugated to MMAE.

Figure 10:
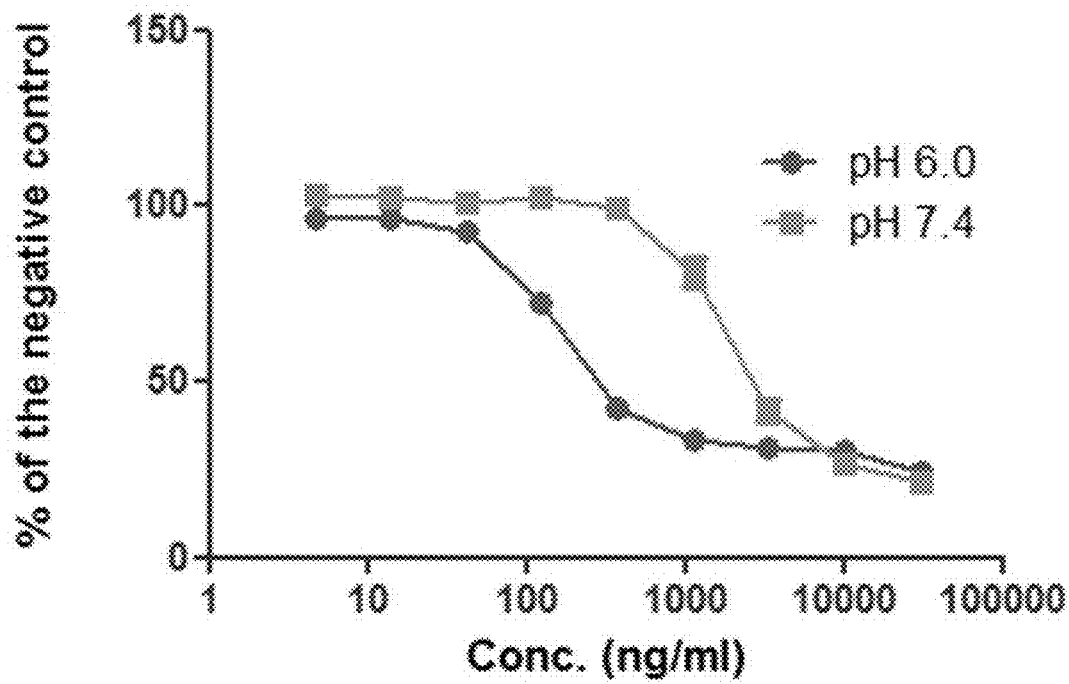
FIG. 10 shows cell killing of the conditionally active antibody BAP048 conjugated to Monomethyl auristatin E (MMAE) on HEK293 cells expressing human Ror2.

The BAP048 ADC was tested under two pH: 6.0 and 7. The percentage of cells remained alive after the treatment, relative to the cells treated by the negative control was presented in FIG. 10. It was observed that the BAP048 ADC displayed cell killing activity at pH 6.0 at a concentration below 100 ng/ml, while at pH 7.4, the BAP048 ADC showed cell killing at about 1000 ng/ml, a difference of effective concentration about 10 fold.

Figure 11A:
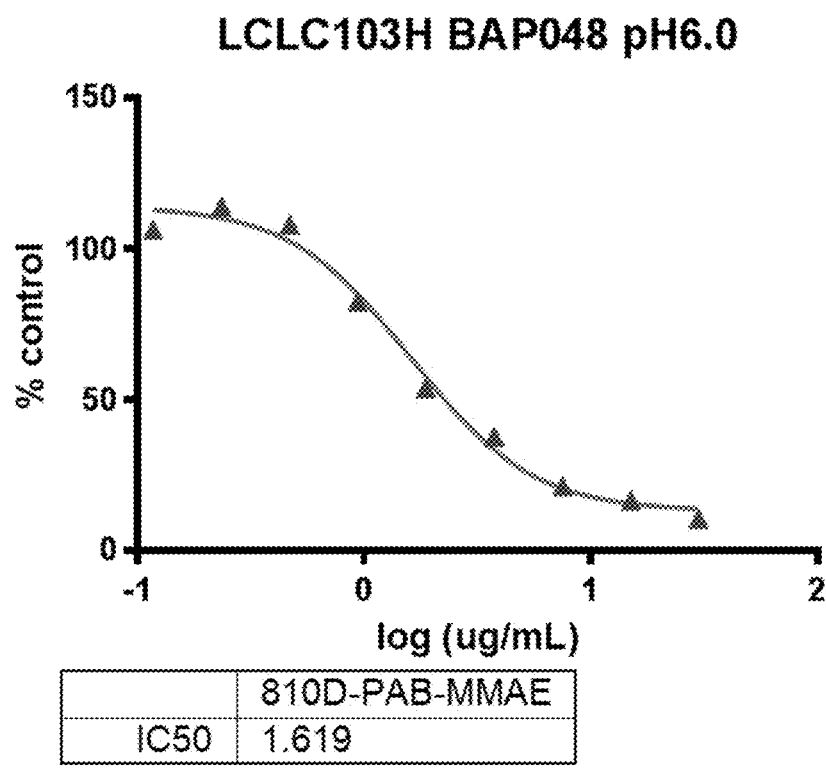
FIGS. 11A, 11B, and 11C show cell killing of the conditionally active antibody BAP048 conjugated to MMAE on LCLC103H cells.
Figure 11B:
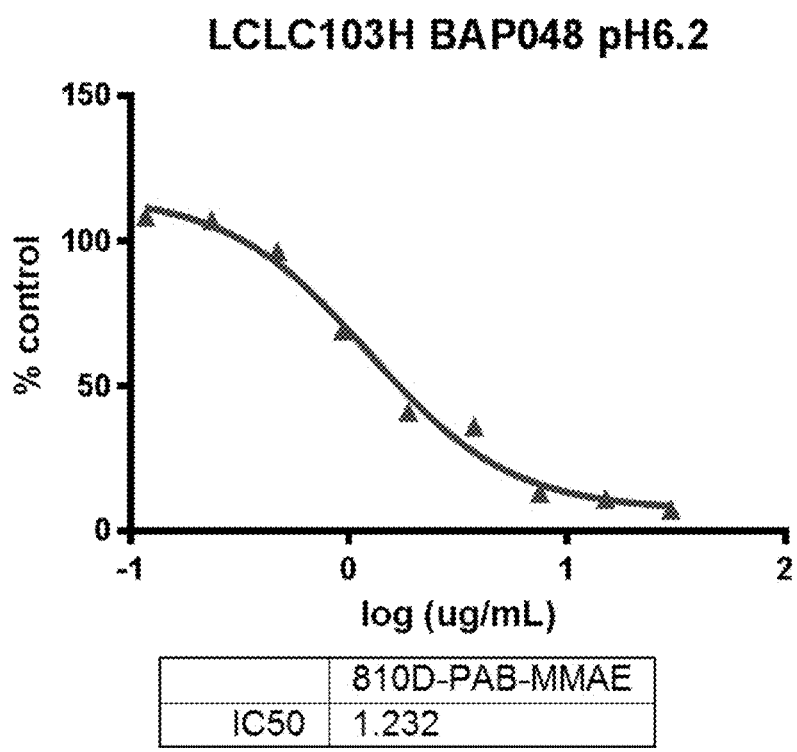
Figure 11C:
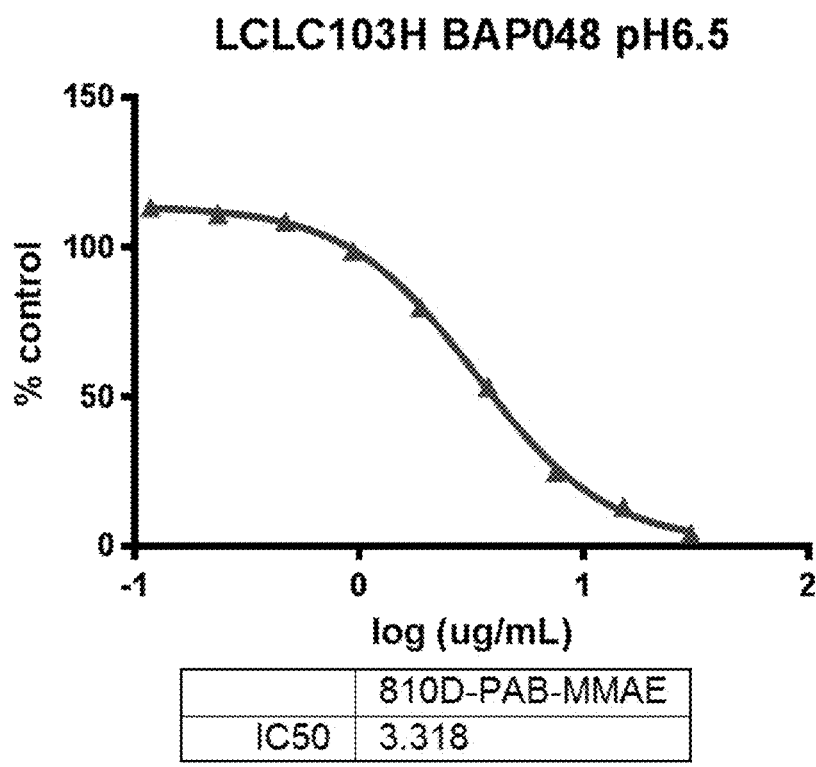

The cell killing activity of the BAP048 ADC was also tested on LCLC103H cells and HT1080 cells. For LCLC103H cells, which are a human lung cancer line, the cell killing activity of the BAP048 ADC was tested at pH 6.0, 6.2, and 6.4 (FIGS. 11A-11C). The difference of the cell killing activity of the BAP048 ADC was not significantly different among the three tested pH values, with the IC50 at 1.819 ng/ml (pH 6.0), 1.232 ng/ml (pH 6.2), and 3.318 ng/ml (pH 6.5).

Figure 12A:
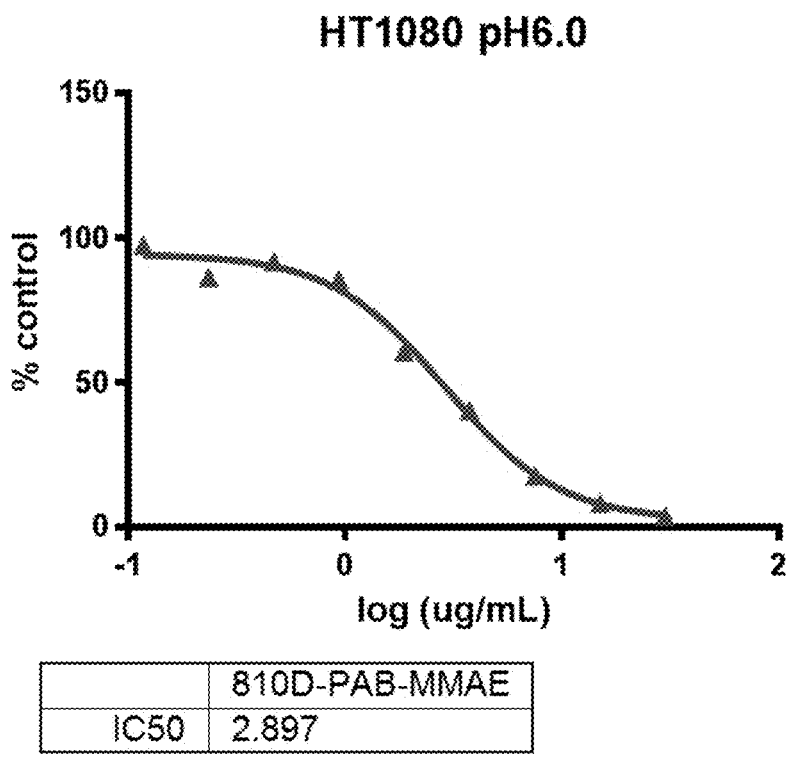
FIGS. 12A, 12B, and 12C show cell killing of the conditionally active antibody BAP048 conjugated to MMAE on HT1080 cells.
Figure 12B:
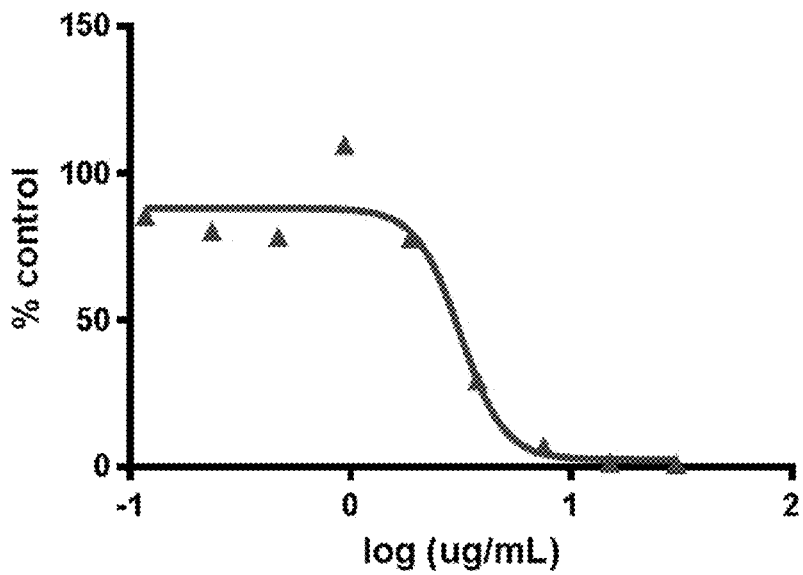
Figure 12C:
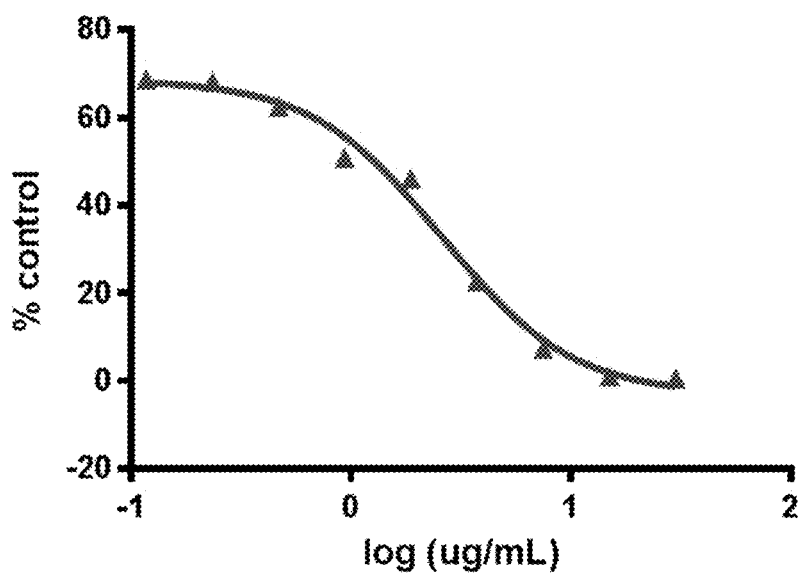

For HT1080 cells, which are a fibrosarcoma cell line, the cell killing activity of the BAP048 ADC was also tested at pH 6.0, 6.2, and 6.4 (FIGS. 12A-12C). The difference of the cell killing activity of the BAP048 ADC was not significantly different among the three tested pH values, with the IC50 at 2.897 ng/ml (pH 6.0), 3.138 ng/ml (pH 6.2), and 2.601 ng/ml (pH 6.5).

Example 6. Treatment of Tumor in Mice by Conditionally Active Antibody BAP048-MMAE Conjugates The lung cancer cells LCLC103H were injected into mice to generate mouse zenografts (tumors in mice). The conditionally active antibody BAP048 was conjugated to MMAE through a linker thiobridge to generate an ADC for injection to the mice at two concentrations 1 mg/kg and 6 mg/kg. The negative control was the buffer (vehicle) without the ADC. One dose group was injected at 1 mg/kg dose weekly for three doses, and the other dose group was injected at 6 mg/kg dose every 4 days for 4 doses.

Figure 13:
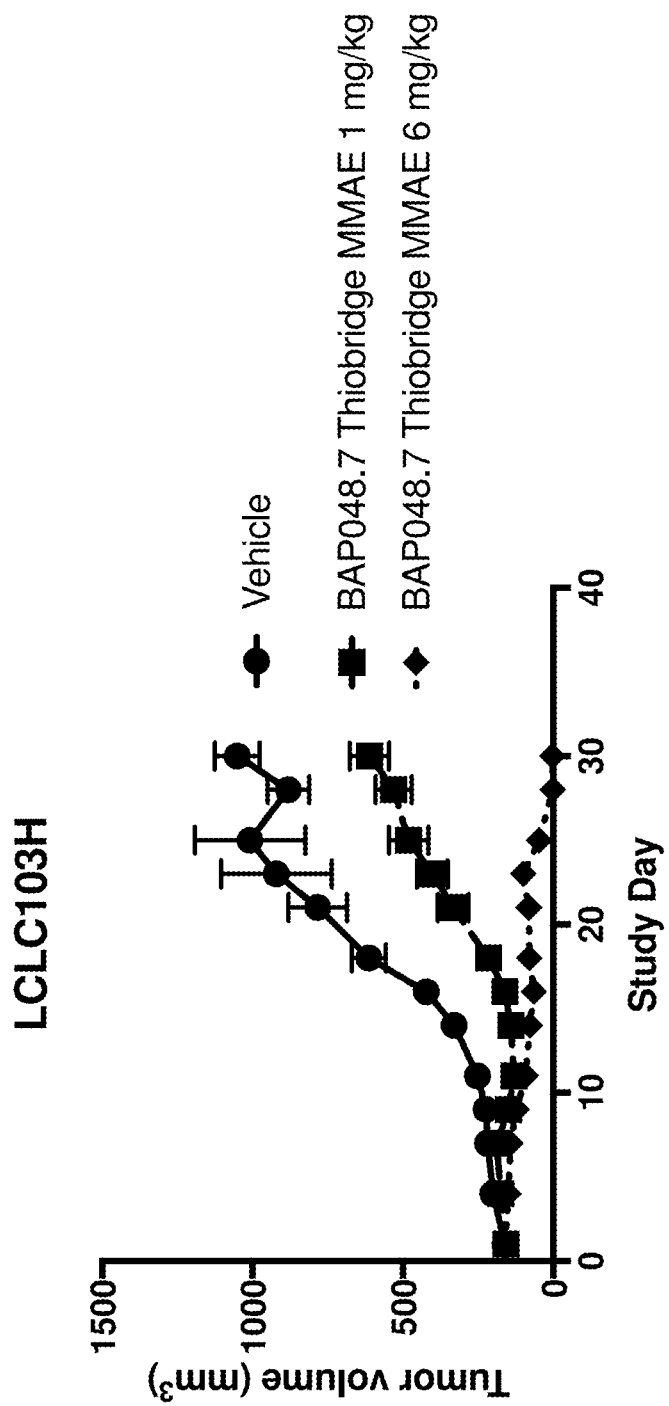
FIG. 13 shows treatment of mouse tumors induced by LCLC103H using the conditionally active antibody BAP048 conjugated to MMAE.

The volumes of the tumors were measured during the study. It was observed that at 6 mg/kg dose group, the tumor size shrank significantly by day 30 by the BAP048-MMAE ADC. At the 1 mg/kg dose group, the tumor growth was slowed by the BAP048-MMAE ADC, in comparison with the vehicle control (FIG. 13).

Figure 14:
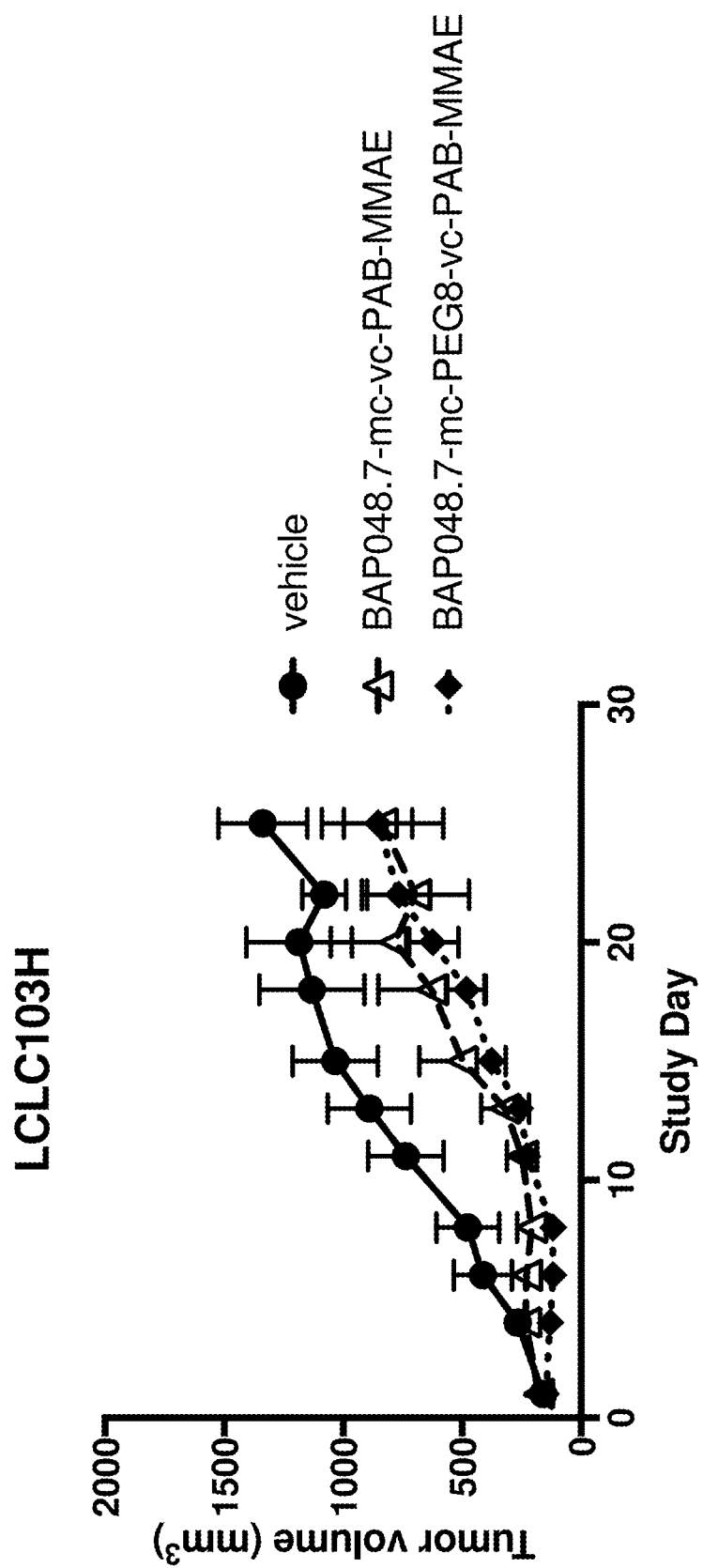
FIG. 14 shows treatment of mouse tumors induced by LCLC103H using the conditionally active antibody BAP048 conjugated to MMAE through different linkers.

Example 7. Effect of Linker in Conditionally Active Antibody BAP048-MMAE Conjugates The effect of the linkers of the conditionally active antibody BAP048 MMAE conjugation was tested using two different linkers: me-vc-PAB and mc-PEG8-vc (FIG. 14). The same negative control (vehicle) was used. These two BAP048-MMAE conjugates were injected into the mouse xenografts at a single dose of 1 mg/ml. The size of the tumors was measured during the study. It was observed that though both BAP048-MMAE conjugates significantly slowed the growth of the tumors in comparison with the negative control, the difference between the two BAP048-MMAE conjugates was not significant (FIG. 14). Thus, it appears the affect of the linkers on the BAP048-MMAE conjugates is not significant.

Example 8. Treatment of Tumor in Mice by Conditionally Active Antibody BAP048

This example is similar to Example 6, except the cells used to induce the tumors in the mice are different. The two cell lines used in this example are HT1080 cells (a fibrosarcoma cell line) and MDA-MB-436 cells (a breast cancer cell line).

Figure 15A:
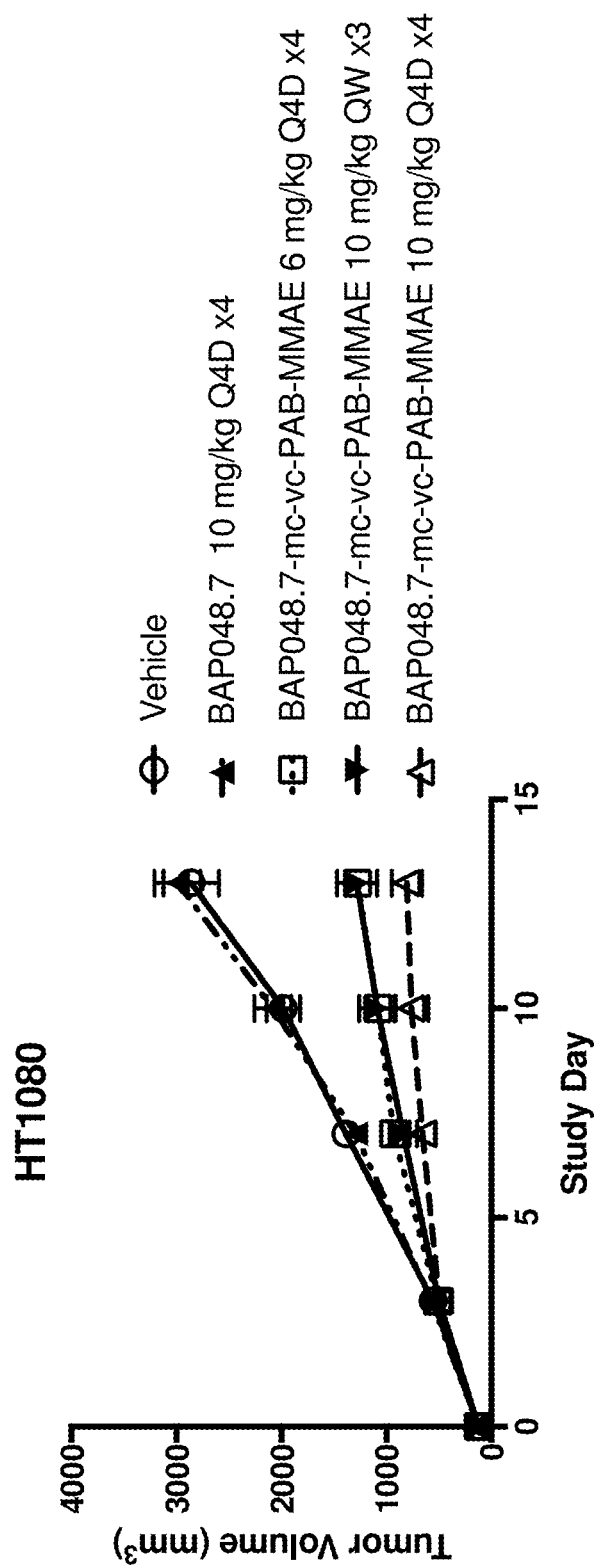
FIGS. 15A-15B show treatment of mouse tumors induced by HT1080 or MDA-MB-436 respectively, using the conditionally active antibody BAP048 conjugated to MMAE.

For the mouse xenograft induced by HT1080, the conditionally active antibody BAP048 was conjugated to MMAE with the linker of me-vc-PAB. Three dose groups were used: 6 mg/kg every 4 days for 4 doses, 10 mg/kg every week for 3 doses, and 10 mg/kg every 4 days for 4 doses (FIG. 15A). Tow controls were used: one is the vehicle without antibody or MMAE, the other is the BAP048 antibody without conjugated MMAE.

It was observed that the tumor grew steadily with the two control groups. The growth of the tumor volume was slowed significantly by the conditionally active antibody BAP048-MMAE conjugates. The inhibition of the tumor growth was dose dependent, with the highest dose group, 10 mg/kg every 4 days for 4 doses, showed the largest reduction in tumor growth (FIG. 15A).

Figure 15B:
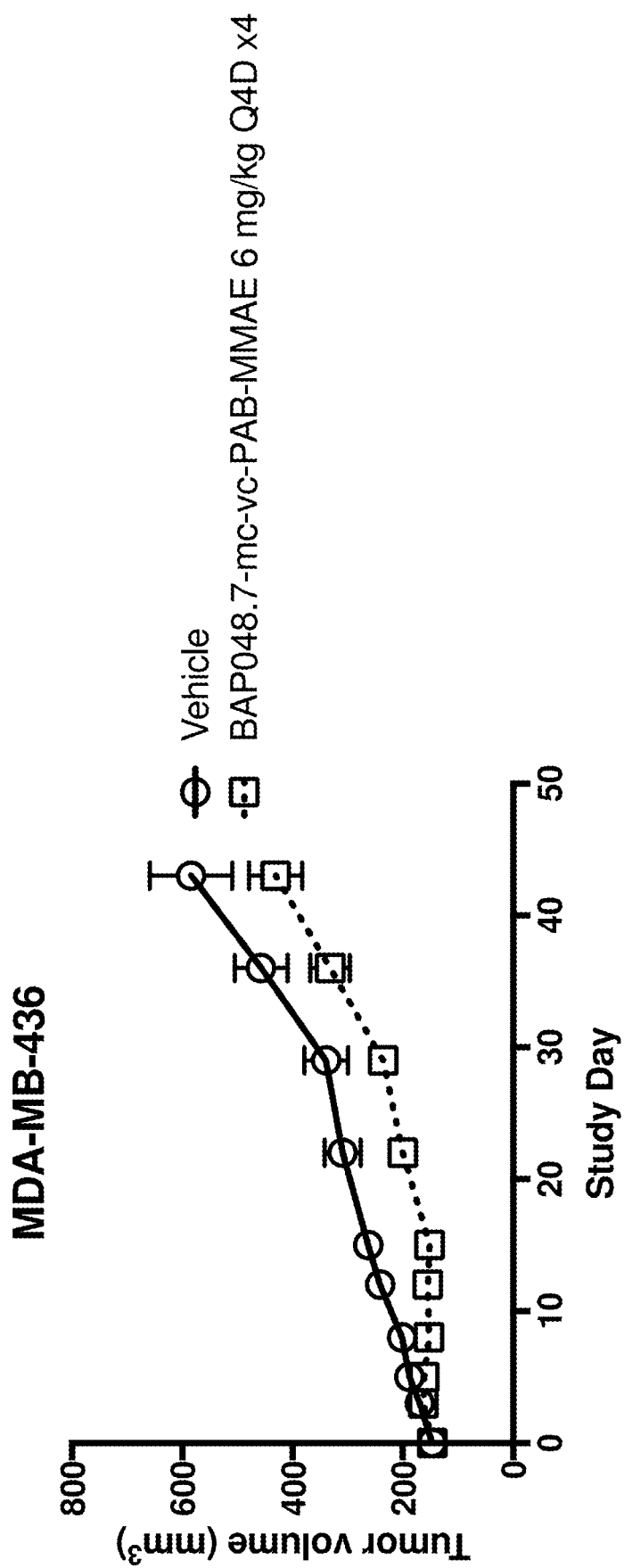

For the mouse xenograft induced by MDA-MB-436, the conditionally active antibody BAP048 was also conjugated to MMAE with the linker of mc-vc-PAB. There was only one dose group: 6 mg/kg every 4 days for 4 doses, with the vehicle (no antibody or MMAE) as the control (FIG. 15B). It was observed that the tumor grew steadily with the control group. The growth of the tumor volume was reduced significantly by the conditionally active antibody BAP048-MMAE conjugates (FIG. 15B).

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

All documents mentioned herein are hereby incorporated by reference in their entirety or alternatively to provide the disclosure for which they were specifically relied upon. The applicant(s) do not intend to dedicate any disclosed embodiments to the public, and to the extent any disclosed modifications or alterations may not literally fall within the scope of the claims, they are considered to be part hereof under the doctrine of equivalents.

What is claimed is:

1. A method of treating cancer comprising administering to a subject in need of such treatment,
   (i) an antibody or antigen-binding fragment thereof that specifically binds to ROR2 protein, said antibody or antigen-binding fragment thereof comprising:
   a heavy chain variable region including three complementarity determining regions, said regions having H1, H2, and H3 sequences, wherein:
   the H1 sequence is $GYTX_1TEX_2X_3X_4H$ (SEQ ID NO: 1);
   the H2 sequence is $X_5X_6X_7X_8NNGGTGYNQKFKG$ (SEQ ID NO: 2); and
   the H3 sequence is $X_9X_{10}X_{11}SX_{12}YX_{13}YX_{14}X_{15}SYFX_{16}X_{17}X_{18}$ (SEQ ID NO: 3);
   wherein
   $X_1$ is F or E,
   $X_2$ is Y or D,
   $X_3$ is T or C,
   $X_4$ is M or D or E or Y,
   $X_5$ is G or S,
   $X_6$ is I or E,
   $X_7$ is N or C or L or V,
   $X_8$ is T or D or E,
   $X_9$ is A or M or T,
   $X_{10}$ is R or H,
   $X_{11}$ is G,
   $X_{12}$ is L or F,
   $X_{13}$ is S,
   $X_{14}$ is G,
   $X_{15}$ is N or E,
   $X_{16}$ is D or L,
   $X_{17}$ is Y or T, and
   $X_{18}$ is W or L; and
   a light chain variable region including three complementarity determining regions, said regions having L1, L2, and L3 sequences, wherein:

the L1 sequence is SATSSX$_{19}$X$_{20}$X$_{21}$MX$_{22}$ (SEQ ID NO: 7);

the L2 sequence is X$_{23}$TSNLAS (SEQ ID NO: 8); and the L3 sequence is QX$_{24}$X$_{25}$SX$_{26}$YPFX$_{27}$X$_{28}$ (SEQ ID NO: 9);

wherein

X$_{19}$ is V or E,

X$_{20}$ is S or D,

X$_{21}$ is Y or C or D,

X$_{22}$ is H or G or L,

X$_{23}$ is G or C or H or P,

X$_{24}$ is Q or E,

X$_{25}$ is R or H,

X$_{26}$ is S or G or I or Q,

X$_{27}$ is T or D, and

X$_{28}$ is F or D or E, wherein the antibody or antigen-binding fragment thereof has a total of one or two mutations in the heavy chain and light chain complementarity determining regions H1, H2, H3, L1, L2, and L3, and the one or two mutations are determined in comparison with the complementarity determining regions H1, H2, H3, L1, L2, and L3 of the parental antibody or antigen-binding fragment thereof in which X$_1$ to X$_{28}$ are F, Y, T, M, G, I, N, T, A, R, G, L, S, G, N, D, Y, W, V, S, Y, H, G, Q, R, S, T, and F, respectively; and wherein the antibody or antigen-binding fragment thereof has a ratio of binding affinity to the ROR2 protein at pH 6.0 to binding affinity to the ROR2 protein at pH 7.4 of at least 1.5; and (ii) at least one of external beam radiotherapy and brachytherapy.

2. The method of claim 1, wherein the heavy chain variable region has an amino acid sequence selected from SEQ ID NOs: 18 and 20-22.

3. The method of claim 1, wherein the light chain variable region has an amino acid sequence selected from SEQ ID NOs: 13, 15 and 16.

4. The method of claim 1, wherein the antibody or antigen-binding fragment thereof has a ratio of binding affinity to the ROR2 protein at pH 6.0 to binding affinity to the ROR2 protein at pH 7.4 of at least 2 to 1.

5. The method of claim 1, wherein the antibody or antigen-binding fragment thereof has a ratio of binding affinity to the ROR2 protein at pH 6.0 to binding affinity to the ROR2 protein at pH 7.4 of at least 3 to 1.

6. The method of claim 1, wherein the antibody or antigen-binding fragment thereof has a ratio of binding affinity to the ROR2 protein at pH 6.0 to binding affinity to the ROR2 protein at pH 7.4 of at least 4 to 1.

7. The method of claim 1, wherein the antibody or antigen-binding fragment thereof has a ratio of binding affinity to the ROR2 protein at pH 6.0 to binding affinity to the ROR2 protein at pH 7.4 of at least 7 to 1.

8. The method of claim 1, wherein the antibody or antigen-binding fragment thereof has a ratio of binding affinity to the ROR2 protein at pH 6.0 to binding affinity to the ROR2 protein at pH 7.4 of at least 10 to 1.

9. A method of treating cancer comprising administering to a subject in need of such treatment,
(i) an immunoconjugate comprising an antibody or antigen-binding fragment thereof of claim 1 conjugated to at least one auristatin; and
(ii) af least one of external beam radiotherapy and brachytherapy.

10. A method of treating cancer comprising administering to a subject in need of such treatment,
(i) an immunoconjugate comprising an anti-ROR2 antibody or antigen-binding fragment thereof having:
(a) a heavy chain variable region of SEQ ID NO: 20 and a light chain variable region of SEQ ID NO: 15;
(b) a heavy chain variable region of SEQ ID NO: 21 and a light chain variable region of SEQ ID NO: 16; or
(c) a heavy chain variable region of SEQ ID NO: 22 and a light chain variable region of SEQ ID NO: 16,
conjugated to at least one agent selected from maytansinoids, auristatins, dolastatins, calicheamicin, pyrrolobenzodiazepines and anthracyclines; and
(ii) at least one of external beam radiotherapy and brachytherapy.

11. The method of claim 10, wherein the heavy chain variable region is SEQ ID NO: 20 and the light chain variable region is SEQ ID NO: 15.

12. The method of claim 10, wherein the heavy chain variable region is SEQ ID NO: 21 and the light chain variable region is SEQ ID NO: 16.

13. The method of claim 10, wherein the heavy chain variable region is SEQ ID NO: 22 and the light chain variable region is SEQ ID NO: 16.

14. The method of claim 10, wherein the at least one agent is an auristatin.

15. The method of claim 14, wherein the auristatin comprise monomethyl auristatin E (MMAE).

16. A method of treating cancer comprising administering to a subject in need of such treatment,
(i) an immunoconjugate that specifically binds to ROR2 protein, said immunoconjugate comprising an anti-ROR2 antibody or antigen-binding fragment thereof comprising:
a heavy chain variable region including three complementarity determining regions, said regions having H1, H2, and H3 sequences, wherein:
the H1 sequence is GYTX$_1$TEX$_2$X$_3$X$_4$H (SEQ ID NO: 1);
the H2 sequence is X$_5$X$_6$X$_7$X$_8$NNGGTGYNQKFKG (SEQ ID NO: 2); and
the H3 sequence is X$_9$X$_{10}$X$_{11}$SX$_{12}$YX$_{13}$YX$_{14}$ X$_{15}$SYFX$_{16}$X$_{17}$X$_{18}$ (SEQ ID NO: 3);
wherein
X$_1$ is F or E,
X$_2$ is Y or D,
X$_3$ is T or C,
X$_4$ is M or D or E or Y,
X$_5$ is G or S,
X$_6$ is I or E,
X$_7$ is N or C or L or V,
X$_8$ is T or D or E,
X$_9$ is A or M or T,
X$_{10}$ is R or H,
X$_{11}$ is G,
X$_{12}$ is L or F,
X$_{13}$ is S,
X$_{14}$ is G,
X$_{15}$ is N or E,
X$_{16}$ is D or L,
X$_{17}$ is Y or T, and
X$_{18}$ is W or L; and
a light chain variable region including three complementarity determining regions, said regions having L1, L2, and L3 sequences, wherein:
the L1 sequence is SATSSX$_{19}$X$_{20}$X$_{21}$MX$_{22}$ (SEQ ID NO: 7);

the L2 sequence is $X_{23}$TSNLAS (SEQ ID NO: 8); and
the L3 sequence is $QX_{24}X_{25}SX_{26}YPFX_{27}X_{28}$ (SEQ ID NO: 9);
wherein
$X_{19}$ is V or E,
$X_{20}$ is S or D,
$X_{21}$ is Y or C or D,
$X_{22}$ is H or G or L,
$X_{23}$ is G or C or H or P,
$X_{24}$ is Q or E,
$X_{25}$ is R or H,
$X_{26}$ is S or G or I or Q,
$X_{27}$ is T or D, and
$X_{28}$ is F or D or E, and
wherein the antibody or antigen-binding fragment thereof has a total of one or two mutations in the heavy chain and light chain complementarity determining regions H1, H2, H3, L1, L2, and L3, and the one or two mutations are determined in comparison with the complementarity determining regions H1, H2, H3, L1, L2, and L3 of the parental antibody or antigen-binding fragment thereof in which $X_1$ to $X_{28}$ are F, Y, T, M, G, I, N, T, A, R, G, L, S, G, N, D, Y, W, V, S, Y, H, G, Q, R, S, T, and F, respectively; and
wherein the immunoconjugate has a ratio of binding affinity to the ROR2 protein at pH 6.0 to binding affinity to the ROR2 protein at pH 7.4 of at least 1.5; and
(ii) at least one of external beam radiotherapy and brachytherapy.

17. The method of claim 16, wherein the immunoconjugate has a ratio of binding affinity to the ROR2 protein at pH 6.0 to binding affinity to the ROR2 protein at pH 7.4 of at least 2 to 1.

18. The method of claim 16, wherein the immunoconjugate has a ratio of binding affinity to the ROR2 protein at pH 6.0 to binding affinity to the ROR2 protein at pH 7.4 of at least 3 to 1.

19. The method of claim 16, wherein the immunoconjugate has a ratio of binding affinity to the ROR2 protein at pH 6.0 to binding affinity to the ROR2 protein at pH 7.4 of at least 4 to 1.

20. The method of claim 16, wherein the immunoconjugate has a ratio of binding affinity to the ROR2 protein at pH 6.0 to binding affinity to the ROR2 protein at pH 7.4 of at least 7 to 1.

21. The method of claim 16, wherein the immunoconjugate has a ratio of binding affinity to the ROR2 protein at pH 6.0 to binding affinity to the ROR2 protein at pH 7.4 of at least 10 to 1.

22. The method of claim 16, wherein the immunoconjugate comprises at least one agent selected from a chemotherapeutic agent, a cytostatic agent, and a cytotoxic agent.

23. The method of claim 22, wherein the at least one agent is selected from maytansinoids, auristatins, dolastatins, calicheamicin, pyrrolobenzodiazepines, and anthracyclines.

24. The method of claim 23, wherein the auristatins comprise monomethyl auristatin E (MMAE).

* * * * *